(12) United States Patent
Jiang et al.

(10) Patent No.: US 11,787,766 B2
(45) Date of Patent: Oct. 17, 2023

(54) COMPOUND HAVING PD-L1 INHIBITORY ACTIVITY, PREPARATION METHOD THEREFOR AND USE THEREOF

(71) Applicant: SHANGHAI ENNOVABIO PHARMACEUTICALS CO., LTD., Shanghai (CN)

(72) Inventors: Lei Jiang, Shanghai (CN); Jianwen Deng, Shanghai (CN); Xiaoli Lu, Shanghai (CN); Ke Shang, Shanghai (CN); Jianyong Shou, Shanghai (CN); Bing Wang, Shanghai (CN); Danyi Wu, Shanghai (CN); Xueli Xu, Shanghai (CN); Yuan Xu, Shanghai (CN); Yi Zhang, Shanghai (CN); Mingwei Zheng, Shanghai (CN)

(73) Assignee: SHANGHAI ENNOVABIO PHARMACEUTICALS CO., LTD., Shanghai (CN)

( * ) Notice: Subject to any disclaimer, the term of this patent is extended or adjusted under 35 U.S.C. 154(b) by 401 days.

(21) Appl. No.: 16/639,949

(22) PCT Filed: Aug. 17, 2018

(86) PCT No.: PCT/CN2018/101191
§ 371 (c)(1),
(2) Date: Jun. 29, 2020

(87) PCT Pub. No.: WO2019/034172
PCT Pub. Date: Feb. 21, 2019

(65) Prior Publication Data
US 2020/0392083 A1 Dec. 17, 2020

(30) Foreign Application Priority Data

Aug. 18, 2017 (CN) .......................... 201710712191.8

(51) Int. Cl.
| | | |
|---|---|---|
| *C07D 213/69* | (2006.01) | |
| *C07D 213/73* | (2006.01) | |
| *C07D 213/84* | (2006.01) | |
| *C07D 401/14* | (2006.01) | |
| *C07D 405/14* | (2006.01) | |
| *C07D 409/14* | (2006.01) | |
| *C07D 519/00* | (2006.01) | |
| *A61K 31/137* | (2006.01) | |
| *A61K 31/165* | (2006.01) | |

(Continued)

(52) U.S. Cl.
CPC .......... *C07D 213/69* (2013.01); *A61K 31/137* (2013.01); *A61K 31/165* (2013.01); *A61K 31/4155* (2013.01); *A61K 31/437* (2013.01); *A61K 31/44* (2013.01); *A61K 31/444* (2013.01); *A61K 31/4545* (2013.01); *A61K 39/12* (2013.01); *A61K 39/245* (2013.01); *A61K 39/29* (2013.01); *A61K 45/06* (2013.01); *C07C 211/03* (2013.01); *C07C 223/02* (2013.01); *C07D 213/73* (2013.01); *C07D 213/84* (2013.01); *C07D 231/40* (2013.01); *C07D 401/14* (2013.01); *C07D 405/14* (2013.01); *C07D 409/14* (2013.01); *C07D 519/00* (2013.01)

(58) Field of Classification Search
CPC .. C07D 213/69; C07D 213/73; C07D 213/84; C07D 401/14; C07D 405/14; C07D 409/14; C07D 519/00; A61K 31/137; A61K 31/165; A61K 31/4155; A61K 31/437; A61K 31/44; A61K 31/444; A61K 31/4545; A61K 39/12; A61K 39/245; A61K 39/29; A61K 45/06
See application file for complete search history.

(56) References Cited

U.S. PATENT DOCUMENTS

| | | | |
|---|---|---|---|
| 9,850,225 B2 | 12/2017 | Chupak et al. | |
| 9,872,852 B2 | 1/2018 | Chupak et al. | |
| 2018/0305315 A1* | 10/2018 | Aktoudianakis | ..... C07D 405/14 |

FOREIGN PATENT DOCUMENTS

| | | |
|---|---|---|
| CN | 105705489 A | 6/2016 |
| CN | 106536515 A | 3/2017 |

(Continued)

OTHER PUBLICATIONS

English Translation of the International Search Report corresponding to PCT/CN2018/101191 dated Nov. 28, 2018; 3 pages.
Dai, Yanpeng et al., "A quinolone-based $Cu^{2+}$ ion complex fluorescence probe for selective detection of inorganic phosphate anion in aqueous solution and its application to living cells," *Spectrochmica Acta Part A: Molecular and Biomolecular Spectroscopy* (Apr. 18, 2017) 183:30-36.

(Continued)

*Primary Examiner* — Timothy R Rozof
(74) *Attorney, Agent, or Firm* — Mintz Levin Cohn Ferris Glovsky and Popeo, P.C.

(57) ABSTRACT

Provided are a compound for the prevention and treatment of diseases associated with PD-L1, a preparation method therefor and use thereof. Specifically, provided are the compound of formula I, the stereoisomer and the racemate thereof, or pharmaceutically acceptable salts thereof, and also provided is an application thereof in the preparation of a drug for the prevention and treatment of diseases associated with PD-L1.

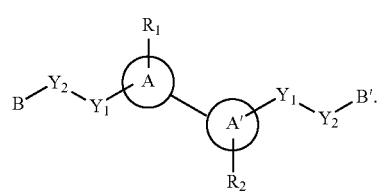

3 Claims, No Drawings

(51) Int. Cl.

| | | |
|---|---|---|
| A61K 31/4155 | (2006.01) | |
| A61K 31/437 | (2006.01) | |
| A61K 31/44 | (2006.01) | |
| A61K 31/444 | (2006.01) | |
| A61K 31/4545 | (2006.01) | |
| A61K 39/12 | (2006.01) | |
| A61K 39/245 | (2006.01) | |
| A61K 39/29 | (2006.01) | |
| A61K 45/06 | (2006.01) | |
| C07C 211/03 | (2006.01) | |
| C07C 223/02 | (2006.01) | |
| C07D 231/40 | (2006.01) | |

(56) References Cited

FOREIGN PATENT DOCUMENTS

| TW | 201225956 A | 7/2012 |
|---|---|---|
| WO | 98/05644 A1 | 2/1998 |
| WO | 2013/117645 A1 | 8/2013 |
| WO | 2018/026971 A1 | 2/2018 |
| WO | WO2018/026971 A1 * | 2/2018 |

OTHER PUBLICATIONS

Dong, Zhi-Bing et al., "A facile synthesis and the asymmetric catalytic activity of BINOL-based thiazole (thiadiazole) thioether ligands," *Journal of Organometallic Chemistry* (2008; available online Oct. 10, 2007); 693:17-22.

Liu, Guo-Cheng et al., "Spacers-induced structural diversity of cobalt coordination polymers based on "Vi"-type dipyridylamide and dicarboxylic ligands: Fluorescent, magnetic and photocatalytic properties," *Polyhedron* (Jan. 25, 2017) 126:205-213.

Nagasawa, Junichi et al., Photoreaction of Heteroaromatic N-Imines with Poly(Vinyl Alcohol) (Dec. 31, 1996) 9(1):93-94.

Sorrell, Thomas N. et al., "3,3'-Disubstituted 2,2'-Biphenols: Synthesis of Nonplanar, Tetradentate Chelating Ligands," *J. Org. Chem.* (Dec. 31, 1985) 59(26):5765-5769.

Tavacoli, Sara et eal., "Synthesis and coordination chemistry of tetradentate ligands containing two bidentate thioquinoline units: mononuclear complexes with Cu(I) and (Cu(II), and a coordination polymer with Cu(I)," *Polyhedron* (Dec. 31, 2003) 22:507-514.

Tran, Phong Lan Thao et al., "Fluorescence intercalator displacement assay for screening G4 ligands towards a variety of G-quadruplex structures," *Biochimie* (May 27, 2011) 93:1288-1296.

* cited by examiner

COMPOUND HAVING PD-L1 INHIBITORY ACTIVITY, PREPARATION METHOD THEREFOR AND USE THEREOF

FIELD OF THE INVENTION

The invention belongs to the field of chemical synthesis, and in particular, the invention relates to a compound having PD-L1 inhibitory activity, preparation method therefor and use thereof.

BACKGROUND OF THE INVENTION

Programmed death-ligand 1 (PD-L1), is also known as cluster of differentiation 274 (CD274) or B7 homolog1 (B7-H1), belongs to tumor necrosis factor superfamily and is a type I transmembrane glycoprotein consisting of 290 amino acid residues. It contains an IgV-like domain, an IgC-like domain, a hydrophobic transmembrane domain, and an intracellular tail containing 30 amino acids. The molecular weight of PD-L1 is 40 kDa. PD-L1 mRNA is present in almost all of tissues, while PD-L1 protein is only continuously expressed in a few tissues, including liver, lungs, tonsils, and immune amnesty tissues, such as eyes, placenta, etc. PD-L1 is also expressed on activated T cells, B cells, monocytes, dendritic cells, macrophages, etc.

The receptor of PD-L1 is PD-1, which is mainly expressed on the surface of activated immune cells, such as $CD4^+$ T cells, $CD8^+$ T cells, NK cells, B cells, monocytes, etc. The binding of PD-L1 to PD-1 can initiate the phosphorylation of tyrosine residues in ITIM (immunoreceptor tyrosine inhibitory motif) in PD-1 cytoplasmic region, promote the binding of tyrosine phospholipase to SHP2, activate SHP2, and dephosphorylate downstream Syk and PI3K, thereby transmitting a termination signal and inhibiting the interaction between antigen-presenting cells or dendritic cells with T cells. Such binding can further inhibit the metabolism of T cells, inhibit the secretion of anti-apoptotic protein Bcl-2, reduce the secretion of effector cytokines IL-2, IFN-γ, and induce T cell depletion and apoptosis, thereby reducing immune responses in which immune T cells are involved, and exerting negative regulation.

After T cells recognize the antigen and are activated, IFN-γ will be secreted. T cell-derived IFN-γ will expand T cells and maintain functions of T cells, such as up-regulating MHC molecules, enhancing antigen processing and presentation of target cells, and promoting T cell differentiation. IFN-γ will also induce the expression of PD-L1 at the site of immune inflammation in a tissue, thereby preventing the tissue from being damaged by excessive immunity. IFN-γ can induce the expression of PD-L1 on the surface of normal epithelial cells, vascular endothelial cells, myeloid cells, naive T cells, and the like. IFN-γ-regulatory factor 1 (IRF-1) induced by interferon can also bind to interferon regulatory factor binding sites at 200 bp and 320 bp upstream to the transcription start site of PD-L1, thereby regulating PD-L1 at the transcription level. PD-L1 can bind PD-1 on the surface of T cells to exert negative regulation, thereby protecting inflammatory sites.

The negative regulation of PD-L1 plays an important role in tumor immunology. In 2004, Konishi et al. first found that PD-L1 was expressed in tissue samples from patients with non-small cell lung cancer, and then PD-L1 was found to be expressed in the tissues of patients with various tumor, including gastric cancer, lung cancer, liver cancer, and intrahepatic cholangiocarcinoma, colon cancer, pancreatic cancer, ovarian cancer, breast cancer, cervical cancer, head and neck squamous cell carcinoma, nasopharyngeal carcinoma, esophageal cancer, bladder cancer, renal cell carcinoma, skin cancer, oral squamous cell carcinoma, etc. During the malignant transformation of cells, new protein molecules will be generated due to gene mutations, exogenous gene (viral) expression or static gene activation, and the like. After these new proteins are degraded in a cell, certain degraded peptide fragments can be expressed on the cell surface and become tumor antigens. The immune system can recognize tumor antigens and eliminate tumor cells through immune monitoring, while tumor cells can escape immune attacks by means of PD-L1.

The expression of PD-L1 at the tumor site can protect tumor cells through various ways. Tumor infiltrating lymphocytes (TIL) secretes IFN-γ, which can induce tumor cells and surrounding stromal cells to express PD-L1. PD-L1 of tumor cells can bind to PD-1 on TIL, inhibit the activation of TIL cells, and further cause apoptosis thereof. In vitro experiments have shown that tumor cell-associated PD-L1 can increase the apoptosis of tumor-specific T cells, while PD-L1 monoclonal antibodies can reduce such effect. Tumor-associated PD-L1 can promote the expression of IL-10 by T cells, and further inhibit the immune response. PD-L1 is not only a ligand of PD-1, but also can act as a receptor to transmit reverse signals to protect tumor cells from apoptosis induced by other anti-tumor pathways, such as FAS-FASL.

Several marketed monoclonal antibody drugs targeting PD-1 or PD-L1 have proven that blockers for PD-1/PD-L1 can be clinically useful in the treatment of various tumors. However, antibody drugs exhibit their own characteristics, such as high production cost, poor stability, necessity to be administered by injection, and proneness to produce immunogenicity, etc. Small molecule drugs have advantages, such as good tissue permeability, convenient storage and transportation, low production cost, non-immunogenicity, and availability of oral administration, etc. Therefore, it is of use and social significance to research and develop small molecule blockers for PD-1/PD-L1.

SUMMARY OF THE INVENTION

The object of the present invention is to provide a compound of formula I or a pharmaceutically acceptable salt thereof, a pharmaceutical composition containing the compound or a pharmaceutically acceptable salt thereof, and the use of compound or composition in the prevention and treatment of diseases related to PD-L1.

In the first aspect of the present invention, a compound of formula I, or a stereoisomer, a racemate or a pharmaceutically acceptable salt thereof is provided,

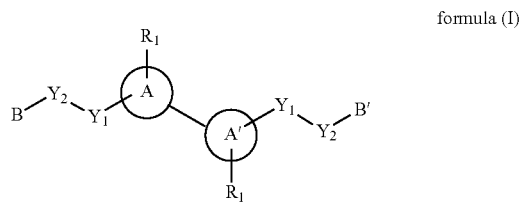

formula (I)

wherein,

The A ring and A' ring are each independently selected from the group consisting of none, substituted or unsubstituted 5-6 membered aryl ring, substituted or unsubstituted 5-7 membered saturated or unsaturated heterocyclic ring, substituted or unsubstituted 7-10 membered heterospiro ring, substituted or unsubstituted 6-10 membered heterocyclic fused ring, substituted or unsubstituted 5-10 membered heteroaromatic ring; and the heterocyclic ring has 1-3 heteroatoms selected from S, O or N; and A ring and A' ring cannot be absent simultaneously;

$R_1$ is selected from the group consisting of H, —CN, —OH, halogen, substituted or unsubstituted C1-C4 alkyl, substituted or unsubstituted C1-C4 alkoxy; and the "substituted" means having the one or more (such as 1, 2, or 3) substituents selected from halogen, and substituted or unsubstituted phenoxy;

$Y_1$ is selected from carbonyl, O, S, amino, substituted or unsubstituted C1-C4 alkyl, substituted or unsubstituted 5-10 membered heteroaryl; and the heteroaryl has 1-4 heteroatoms selected from N or O;

$Y_2$ is selected from O, S, N, substituted or unsubstituted amido, sulfonamido, substituted or unsubstituted C1-C4 alkyl, substituted or unsubstituted 5-10 membered aromatic group, substituted or unsubstituted 5-10 membered heteroaryl and the heteroaryl has 1-3 heteroatoms selected from S, O or N; and $Y_1$ and $Y_2$ cannot be heteroatoms simultaneously;

B and B' are each independently selected from the group consisting of none, H, substituted or unsubstituted amino, substituted or unsubstituted C1-C4 alkylamino, substituted or unsubstituted 5-10 membered aryl, substituted or unsubstituted 5-10 membered heteroaryl and the heteroaryl has 1-3 heteroatoms selected from S, O, N, substituted or unsubstituted —NH—C(=O)—, substituted or unsubstituted C1-C4 alkyl; and the B ring and B' ring cannot be absent at the same time; and the "substituted" means having one or more (such as 1, 2, 3 or 4) substituents selected from the group Z:

group Z substituents are selected from the group consisting of H, substituted or unsubstituted C1-C4 alkylamino, substituted or unsubstituted C1-C4 alkyl, substituted or unsubstituted C1-C4 alkoxy; and the "substituted" means having one or more (such as 1, 2, 3, or 4) substituents selected from the Z' group; wherein the Z' substituent is selected from: substituted or unsubstituted 5-7 membered aryl, C1-C4 alkylamino, substituted or unsubstituted C1-C4 alkyl, methylcarbonyl, substituted or unsubstituted 5-6 membered saturated carbocyclic ring, substituted or unsubstituted 5-7 membered saturated heterocyclic group, substituted or unsubstituted 5-7 membered heteroaryl, and the heteroaryl or heterocyclic group has 1-3 heteroatoms selected from S, O and N;

and, in the A ring, A' ring, $Y_1$-$Y_2$ and Z' substituents, the "substituted" means substituted by groups selected from the group consisting of —OH, —CN, —COOH, —O-aminocarbonyl, C1-C4 alkyl, hydroxy C1-C4 alkyl,

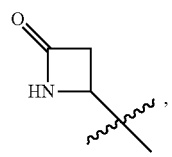 [SMILES: *C1CC(=O)N1]

C1-C4 alkylcarbonyl;

and the compound of formula I is other than compounds selected from the group consisting of:

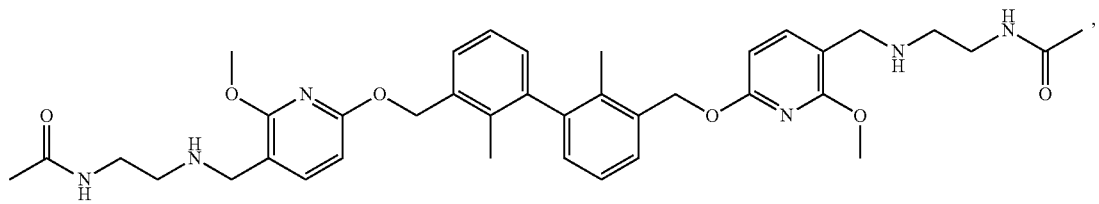

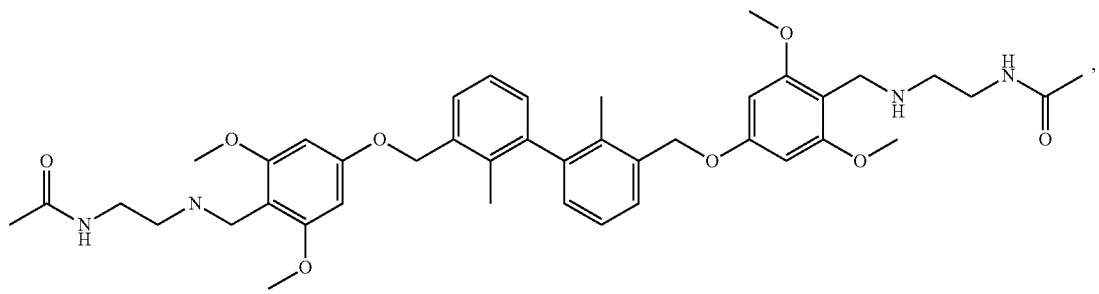

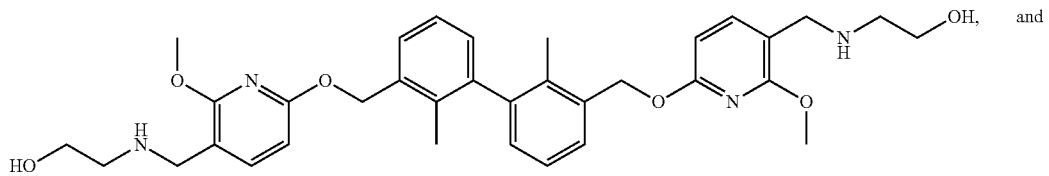

-continued

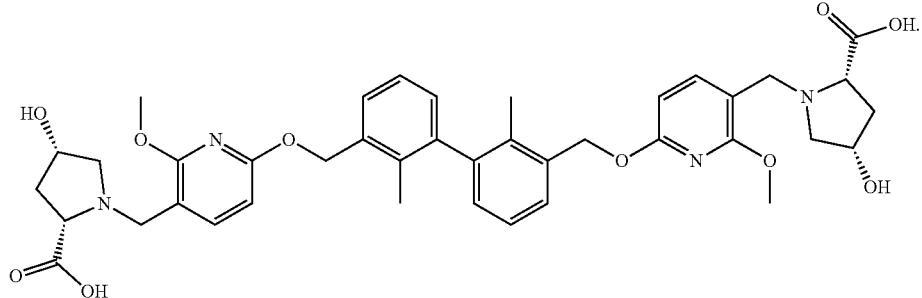

In another preferred embodiment, the A ring and A' ring are selected from:

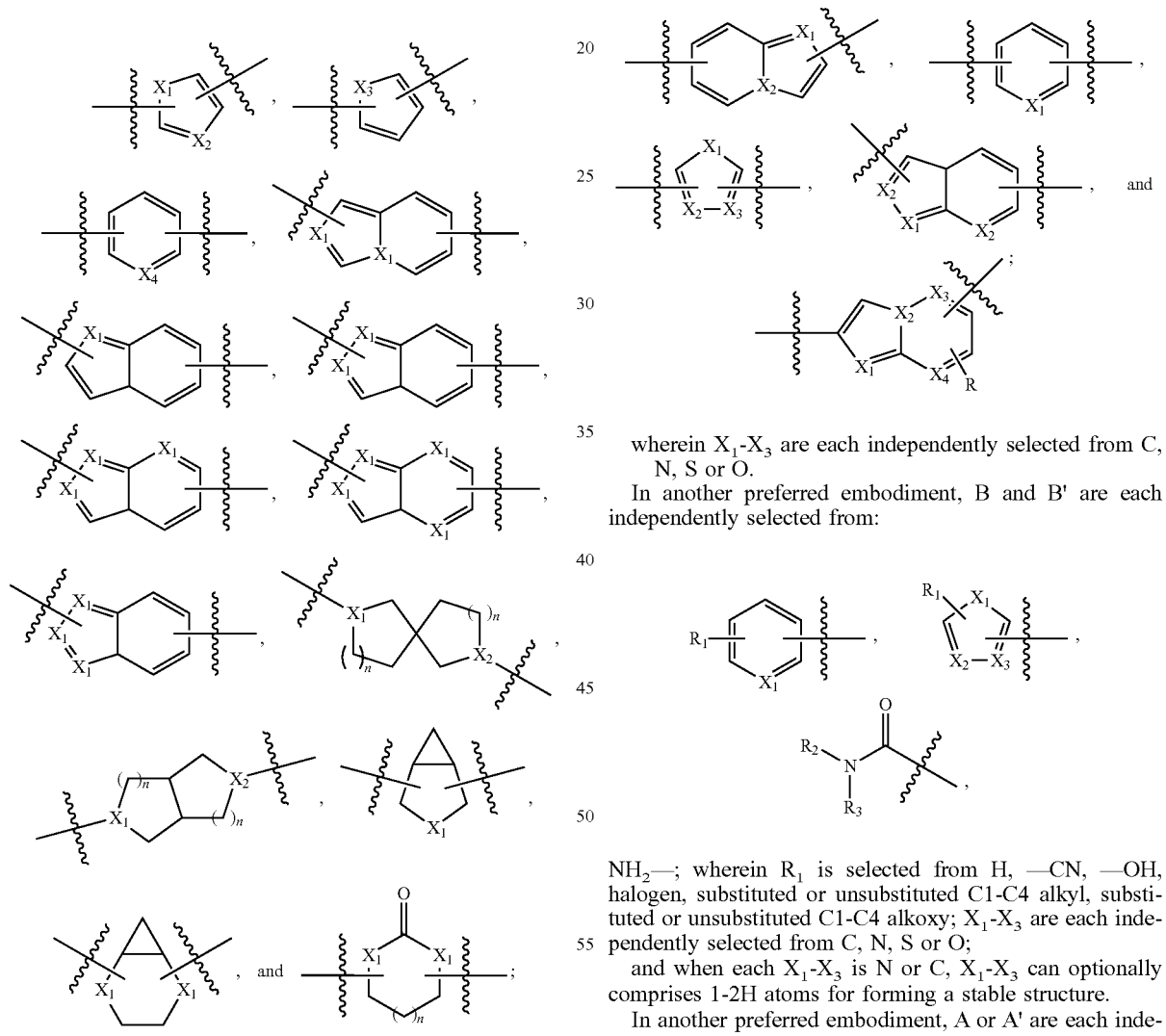

wherein n is 0, 1, 2, or 3;

$X_1$-$X_4$ are each independently selected from N, O, S or C;

and when each $X_1$-$X_4$ is N or C, $X_1$-$X_4$ can optionally comprises 1-2H atoms for forming a stable structure.

In another preferred embodiment, the $Y_1$ and $Y_2$ are each independently selected from:

C1-C4 alkyl, —NH$_2$—,

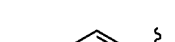

wherein $X_1$-$X_3$ are each independently selected from C, N, S or O.

In another preferred embodiment, B and B' are each independently selected from:

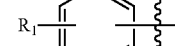

NH$_2$—; wherein $R_1$ is selected from H, —CN, —OH, halogen, substituted or unsubstituted C1-C4 alkyl, substituted or unsubstituted C1-C4 alkoxy; $X_1$-$X_3$ are each independently selected from C, N, S or O;

and when each $X_1$-$X_3$ is N or C, $X_1$-$X_3$ can optionally comprises 1-2H atoms for forming a stable structure.

In another preferred embodiment, A or A' are each independently selected from:

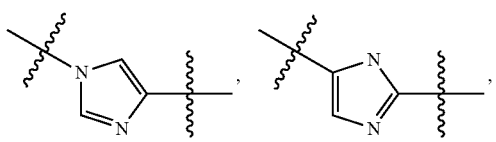

-continued

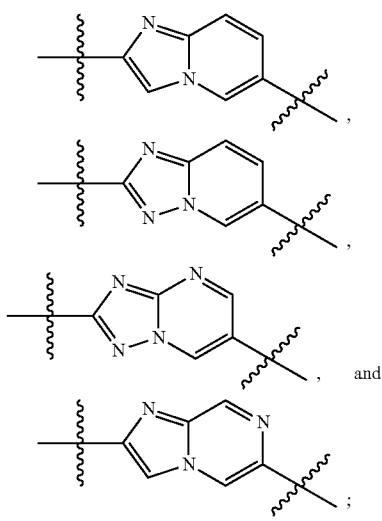

In another preferred embodiment, the $Y_1$ is selected from N, carbonyl, C1-C4 alkyl, In another preferred embodiment, the $Y_2$ is selected from the group consisting of O, N, C1-C4 alkyl, amido, pyridyl, piperidinyl, pyrrolyl,

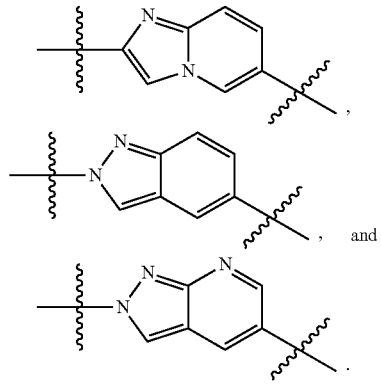

In another preferred embodiment, the compound of formula I is a compound of formula Ia as follows,

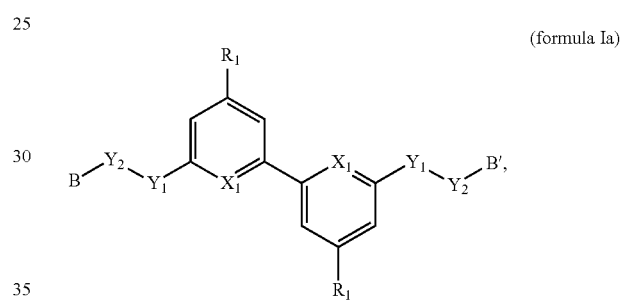

(formula Ia)

wherein the $R_1$, $Y_1$, $Y_2$, B, B' are as described above.

In another preferred embodiment, the compound of formula I is a compound of formula Ib as follows,

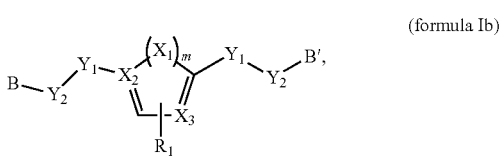

(formula Ib)

wherein, the $R_1$, $Y_1$, $Y_2$, B, B' are as described above; $X_1$, $X_2$, and $X_3$ are each independently selected from O, S, N or C; and m is 1, 2 or 3.

In another preferred embodiment, the compound of formula I is a compound of following formula Ic as follows,

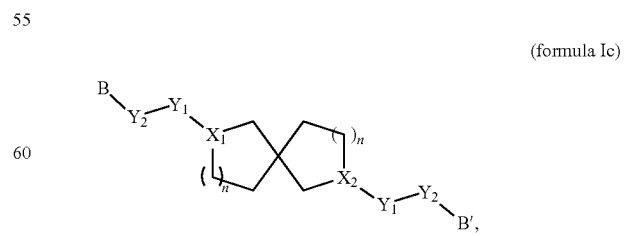

(formula Ic)

wherein, the $Y_1$, $Y_2$, B and B' are as described above; $X_1$ and $X_2$ are each independently selected from O, S, N or C; and n is 0, 1, 2 or 3.

In another preferred embodiment, the compound of formula I is a compound of following formula Id as follows,
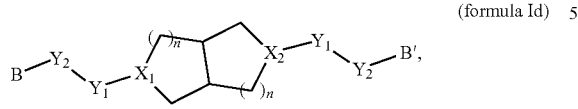
(formula Id)
wherein, the definitions of $Y_1$, $Y_2$, B, and B' are as described above; $X_1$ is selected from O, S, N or C; and n is 0, 1, 2 or 3.
In another preferred embodiment, the compound is selected from the group consisting of:
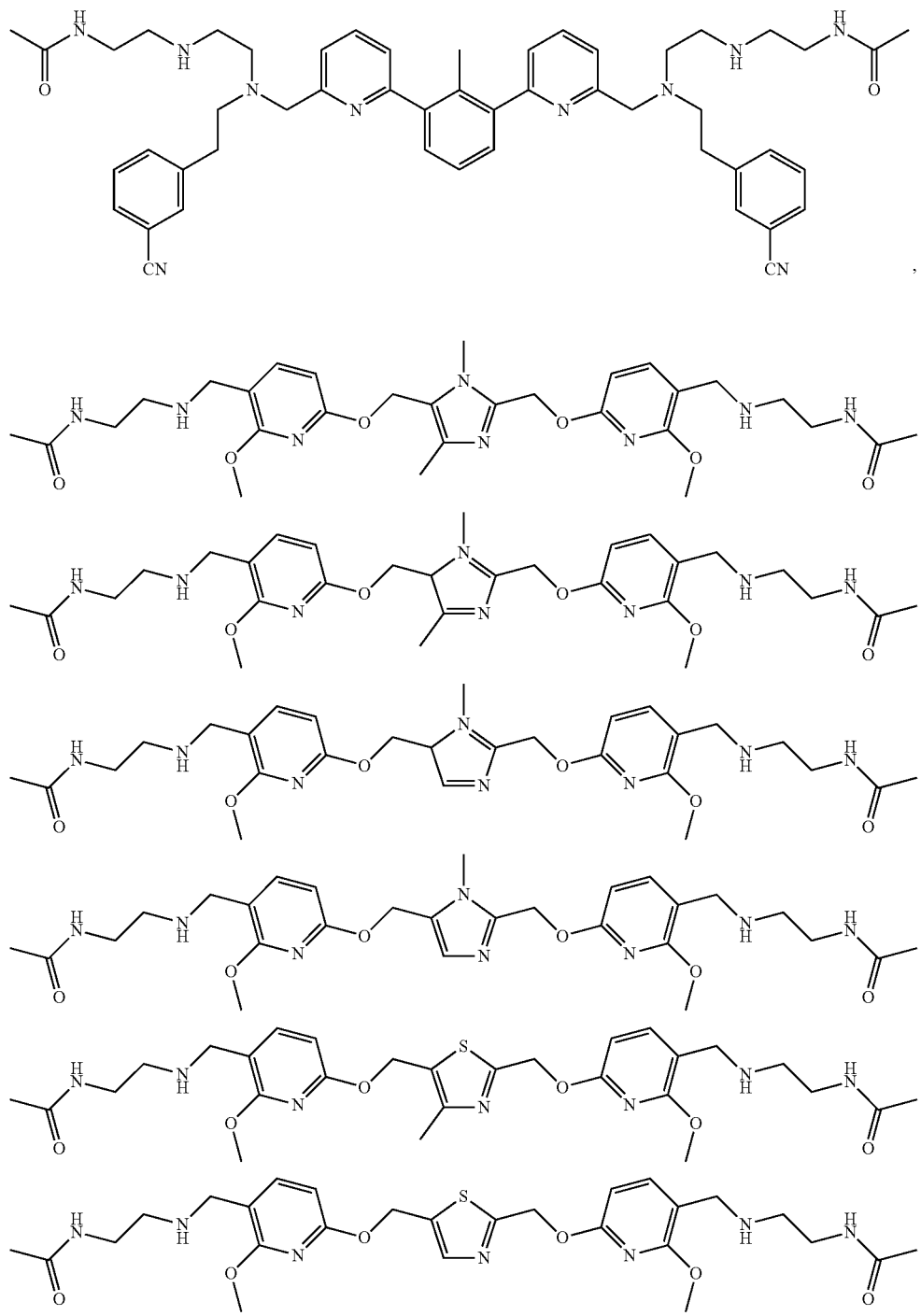

-continued
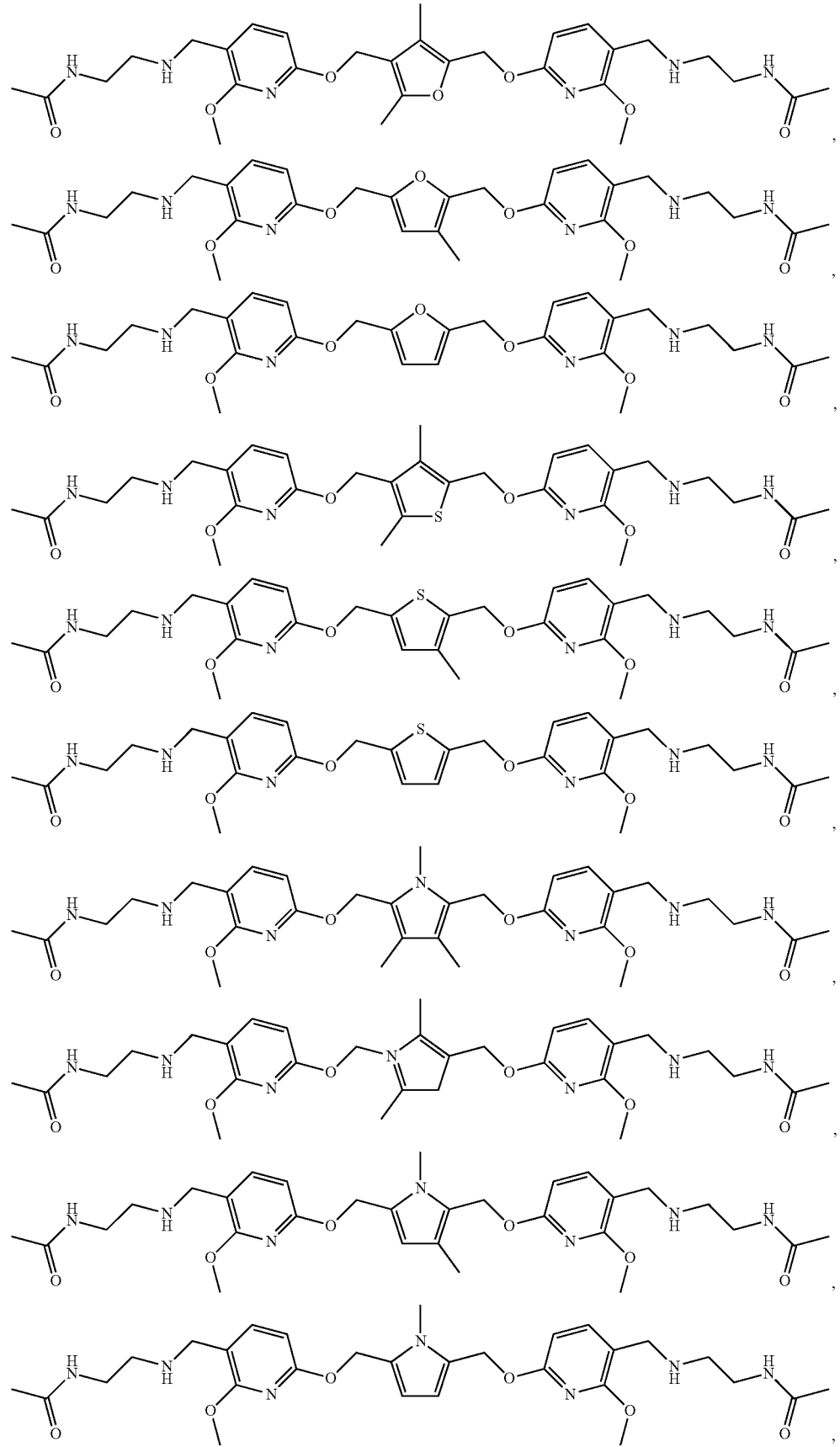

-continued
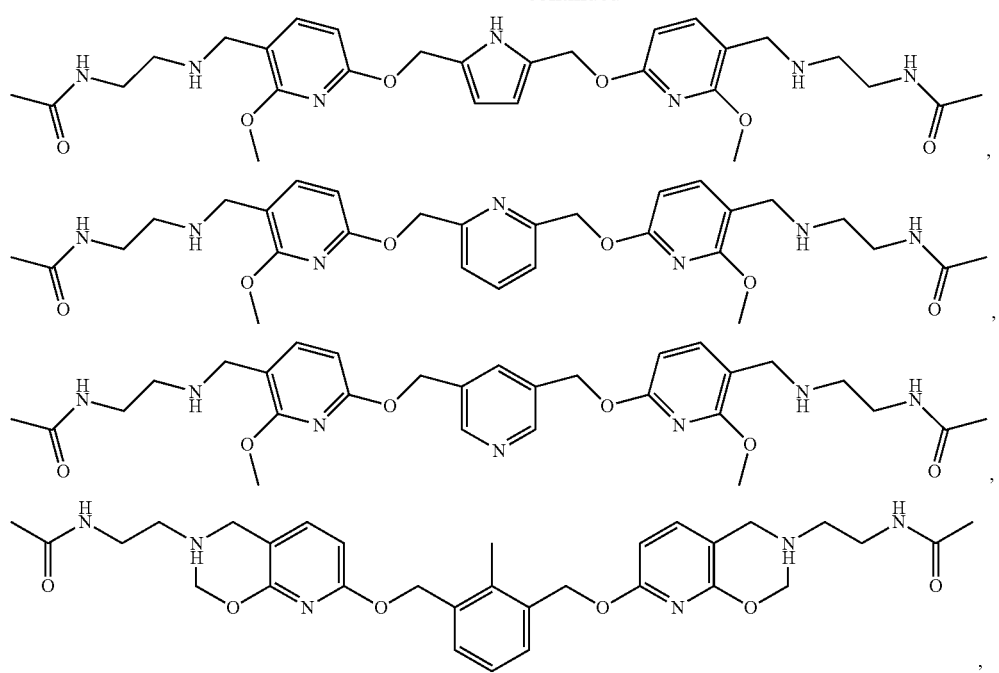
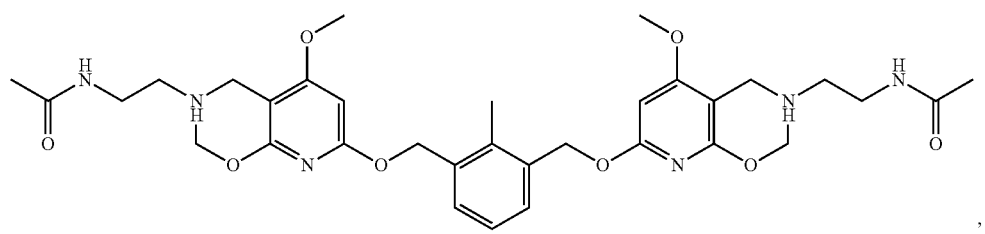
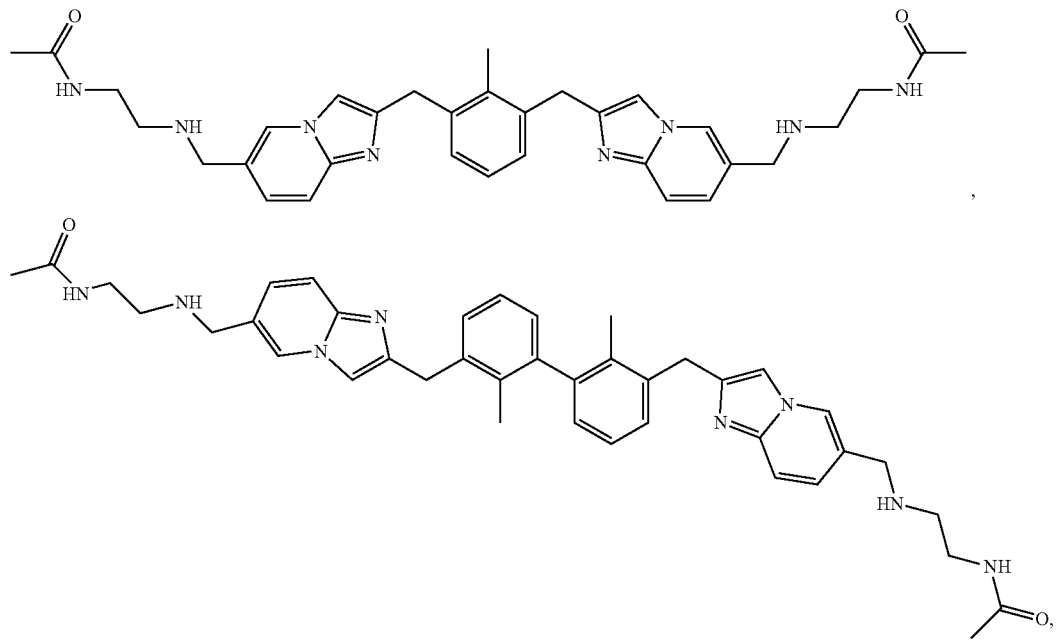

-continued
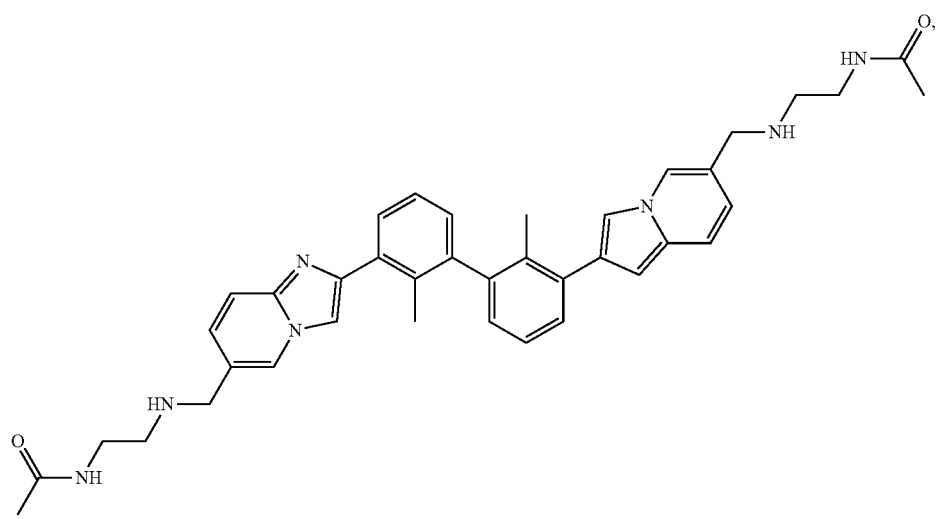
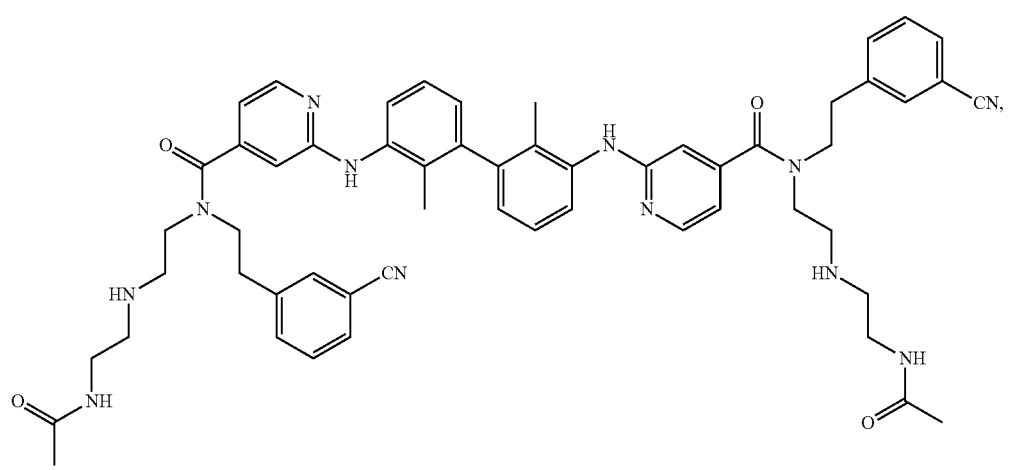
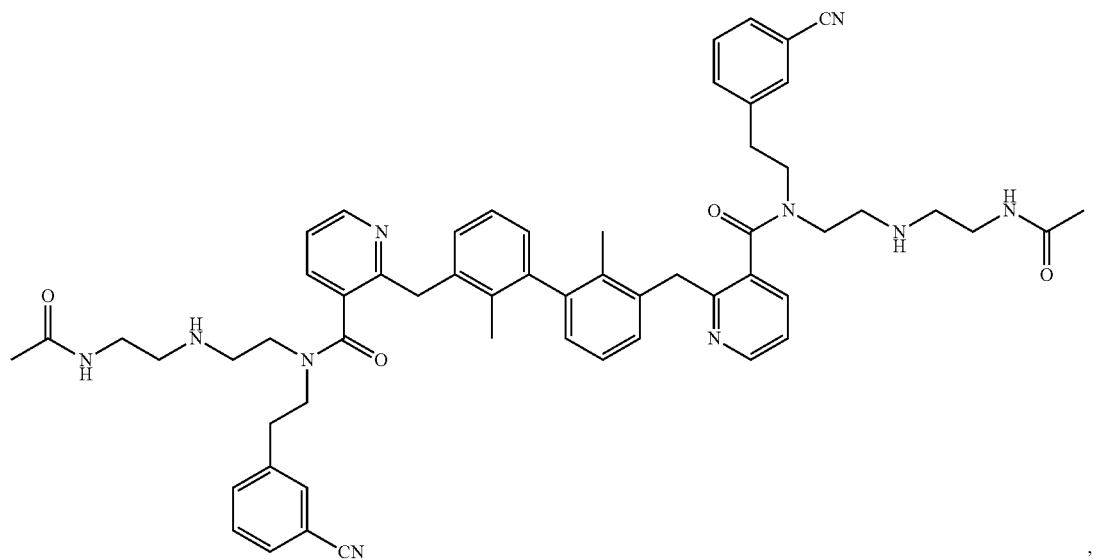

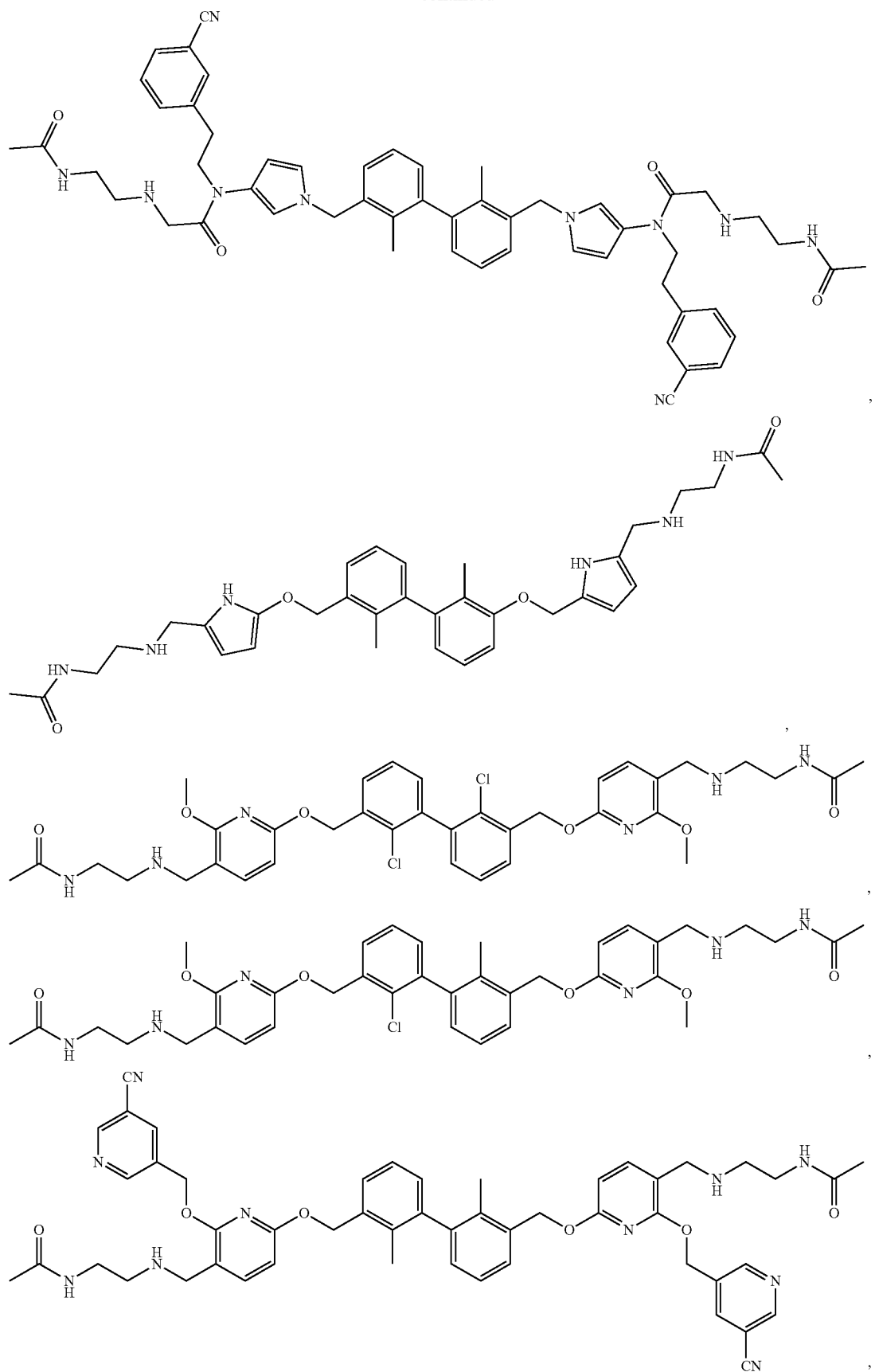

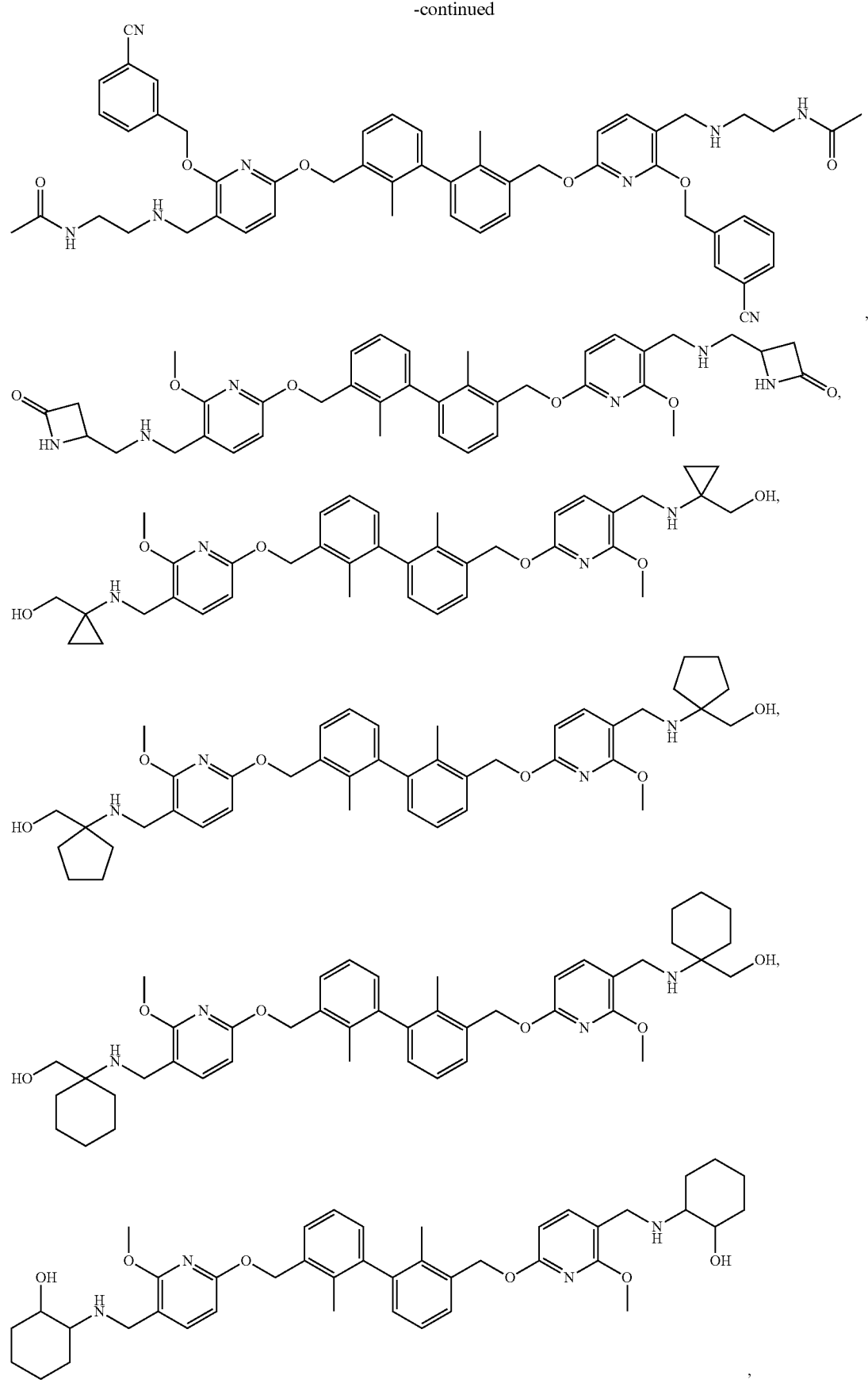

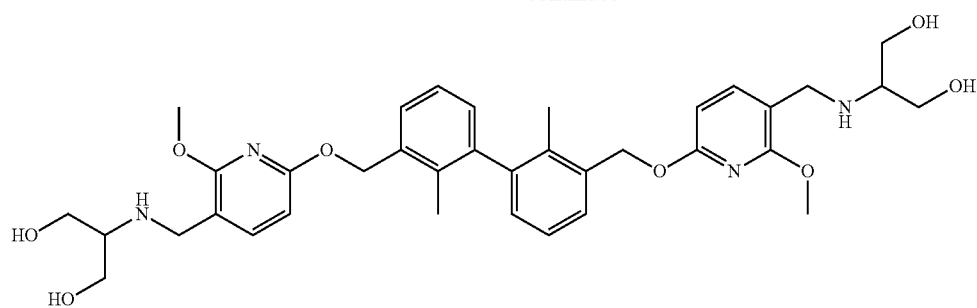
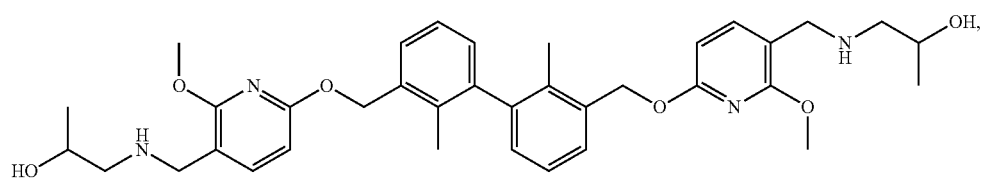
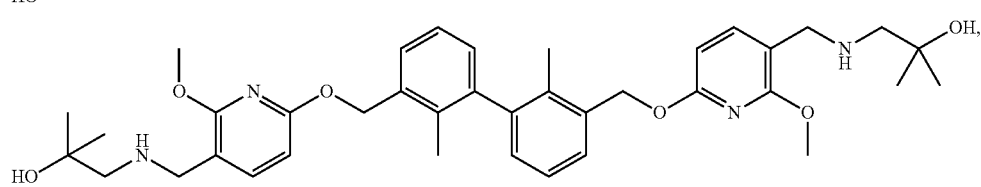
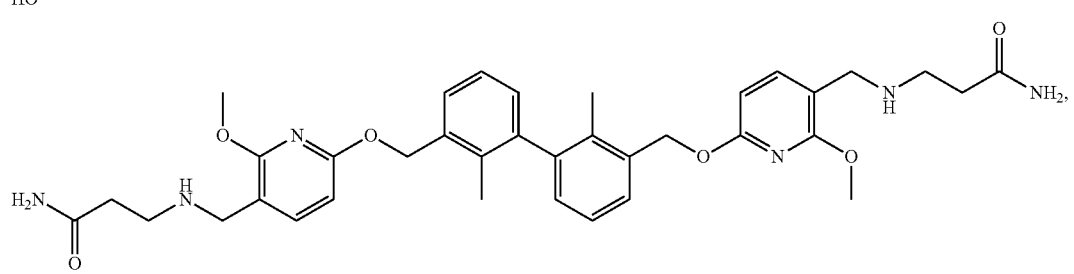
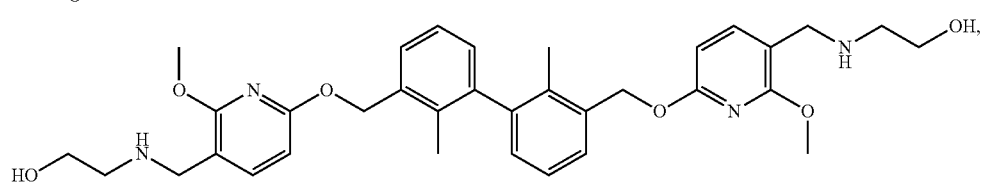
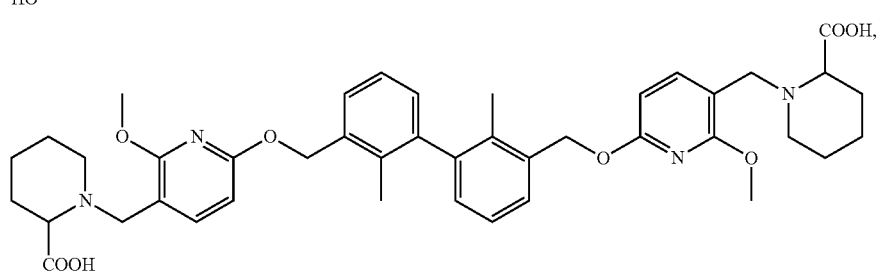
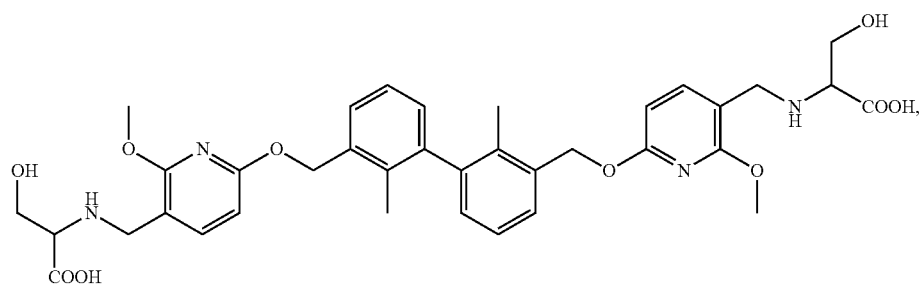

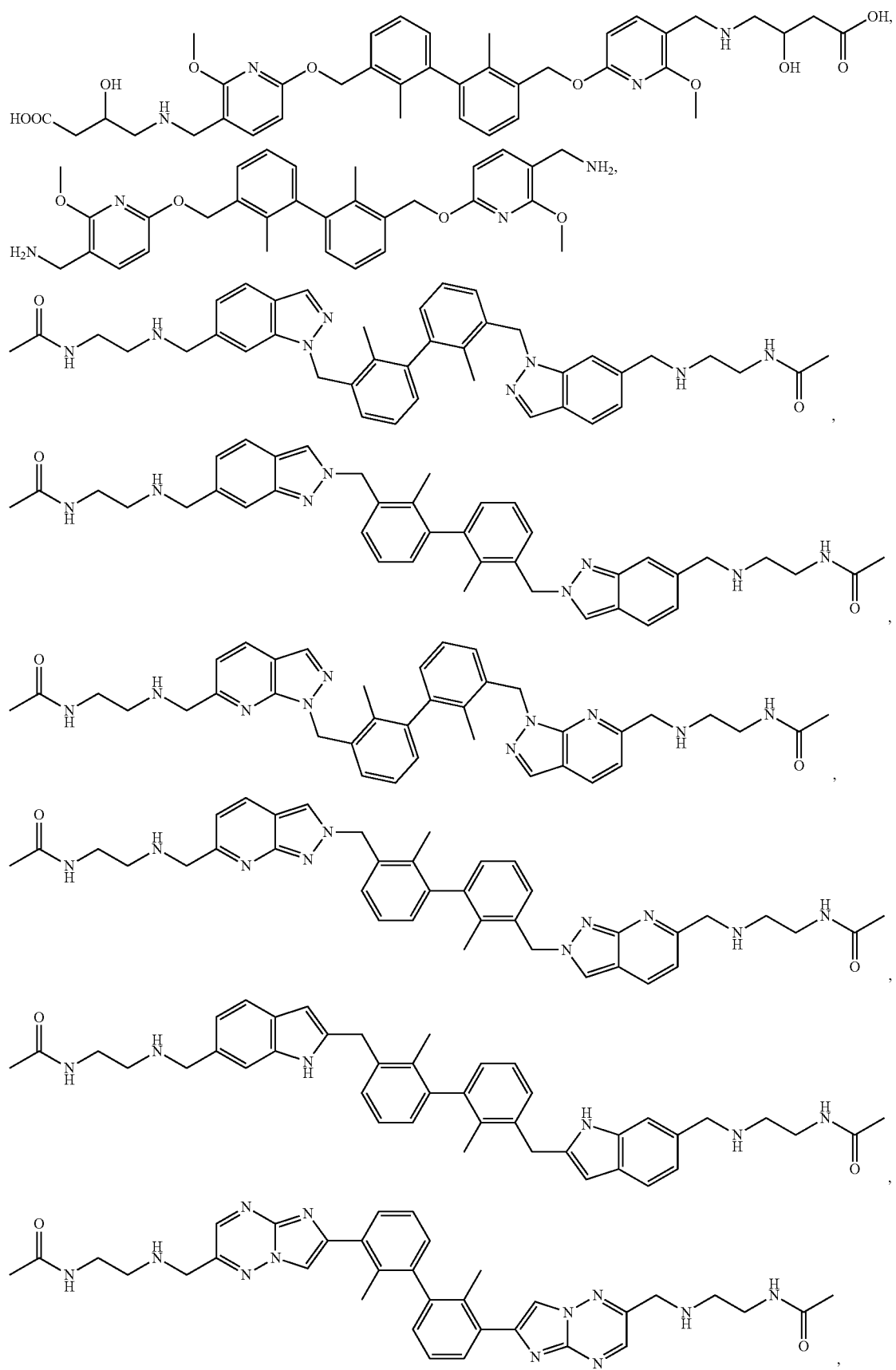

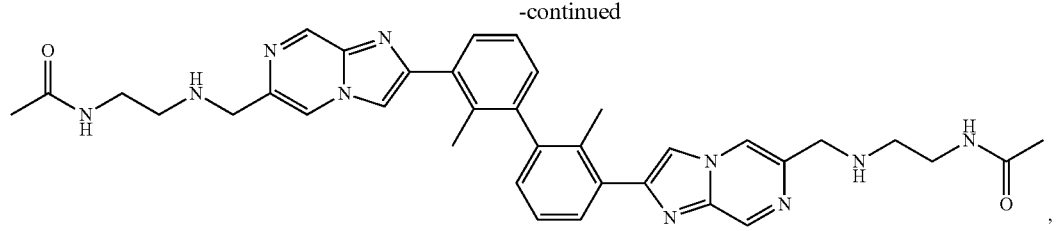,
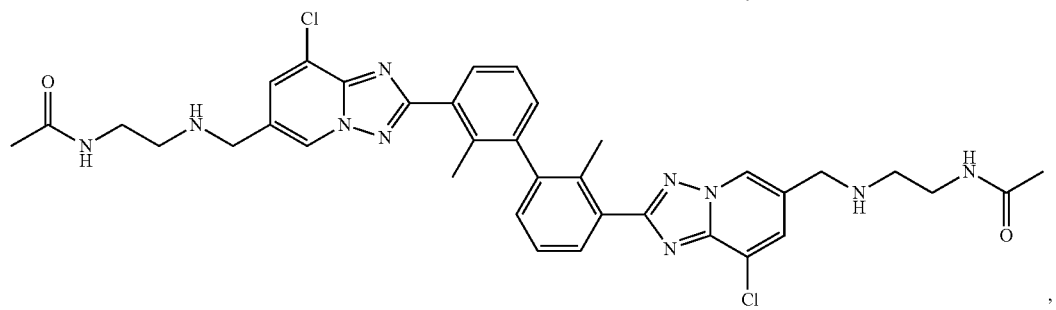,
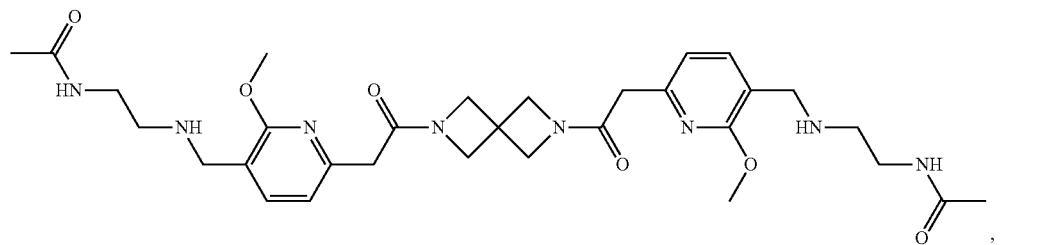,
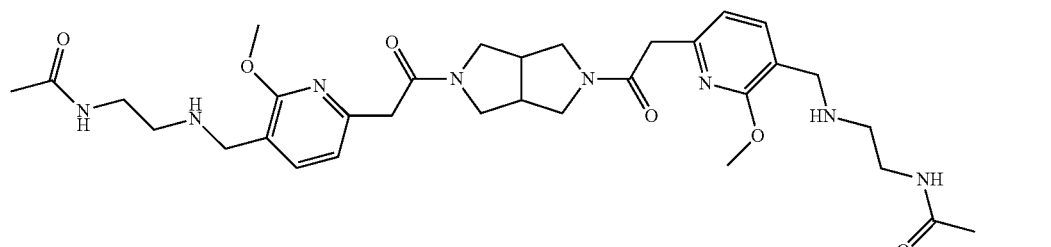,
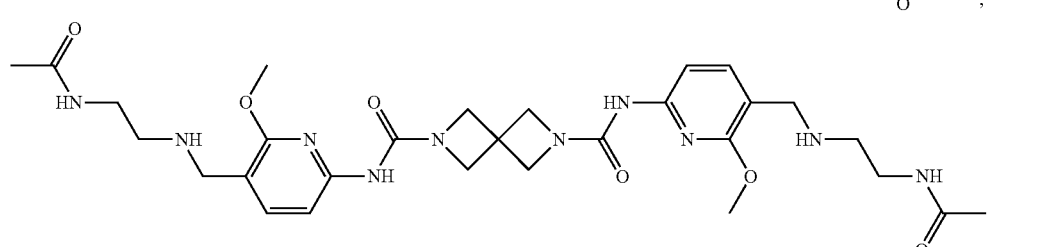,
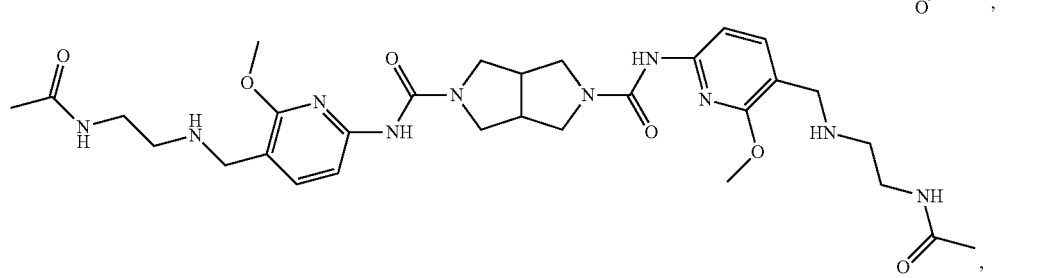,
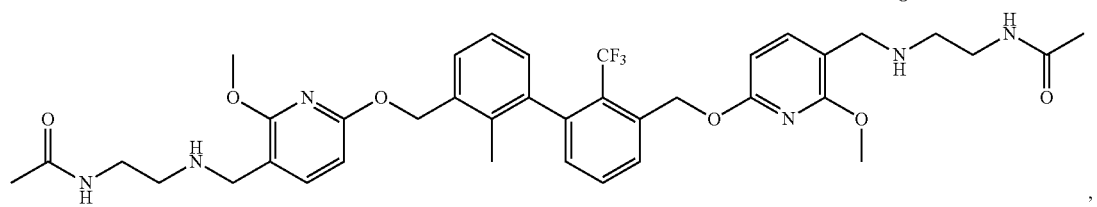,

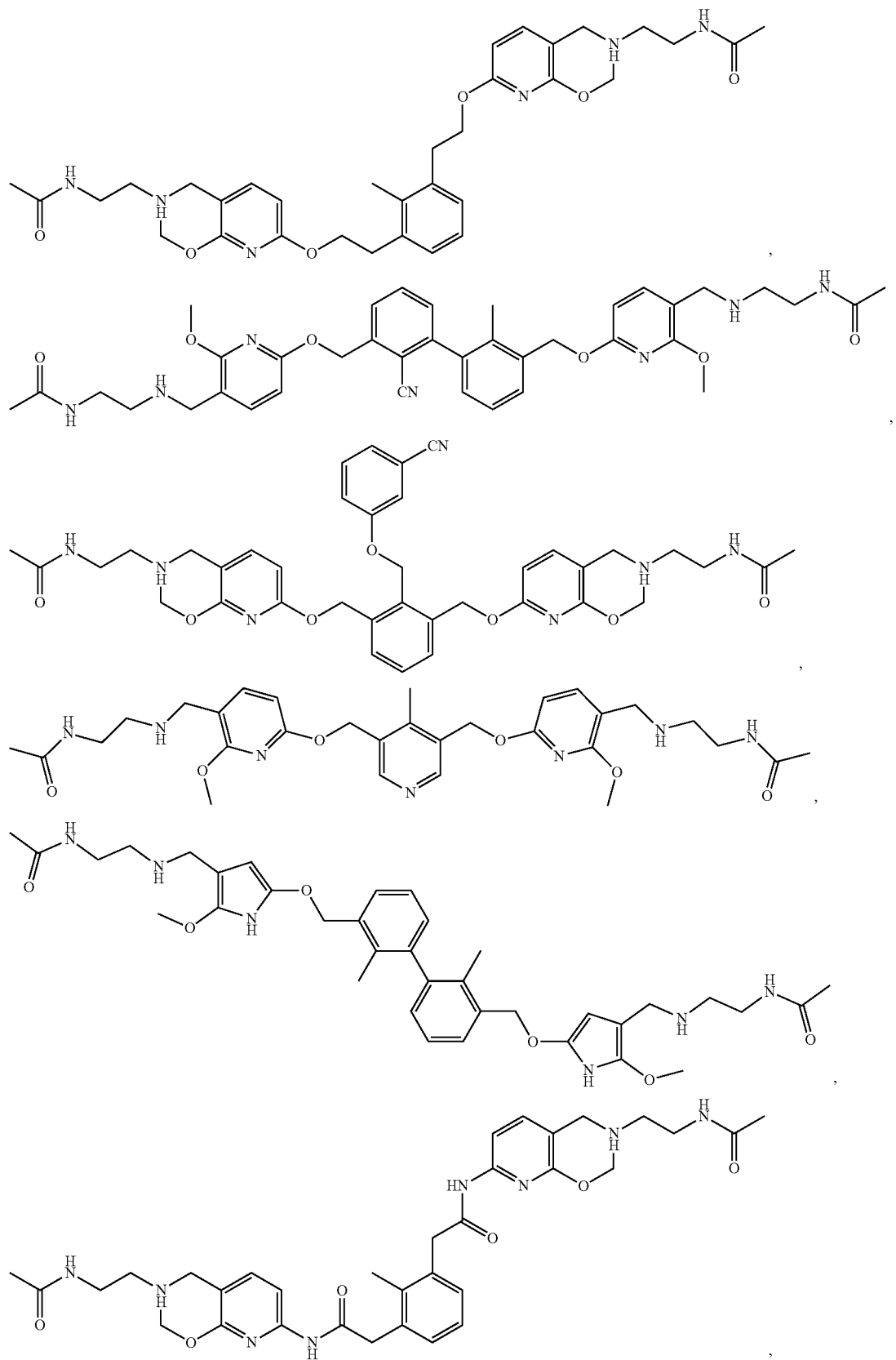

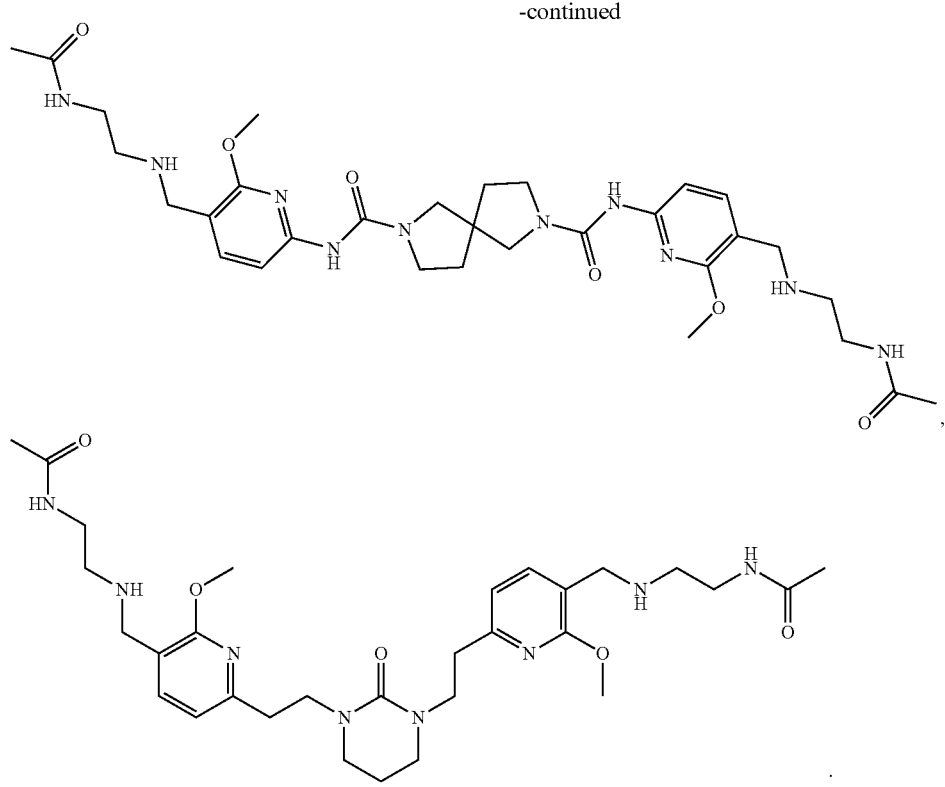

In the second aspect of the present invention, a pharmaceutical composition is provided, wherein comprising a therapeutically effective amount of the compound, or a stereoisomer, a racemate, or a pharmaceutically acceptable salt thereof according to the first aspect of the present invention, and pharmaceutically acceptable excipients.

In another preferred embodiment, the pharmaceutical composition is injection, capsule, tablet, pill, powder or granule.

In the third aspect of the present invention, a method for preparing the compound according to the first aspect of the present invention is provided, which comprises the steps: in a suitable solvent and in the presence of a base and a phosphine compound, reacting compound 1 (Q is selected from 0 or N) with compound 2 (n=1, 2) under the action of a palladium catalyst to afford compound 3; then subjecting compound 3 to a reductive amination reaction to obtain a compound of formula 4.

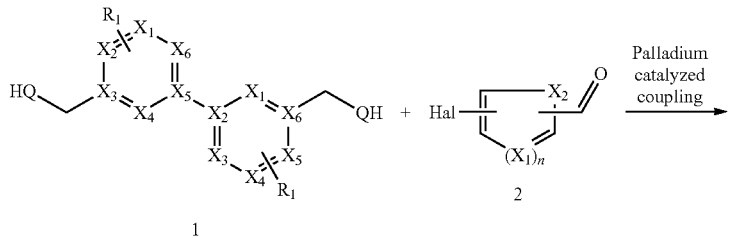

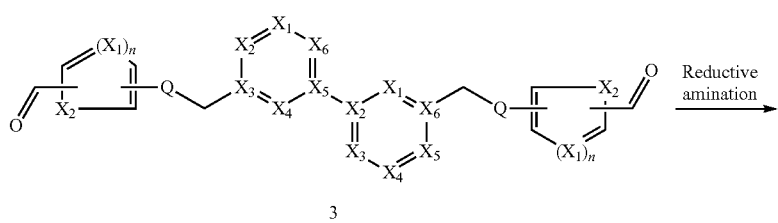

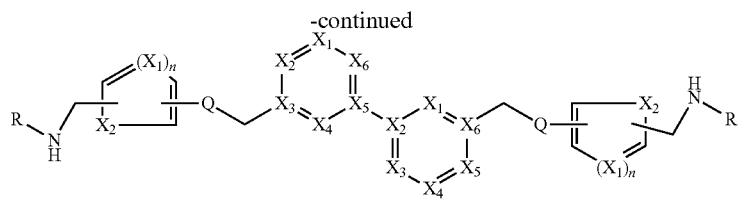

4

In another preferred embodiment, said solvent is selected from the group consisting of toluene, 1,4-dioxane, and N,N-dimethylformamide; In another preferred embodiment, the palladium catalyst is selected from palladium acetate;

In another preferred embodiment, the base is selected from cesium carbonate, potassium phosphate;

In another preferred embodiment, the phosphine compound is selected from 2-di(tert-butylphosphino)-2',4',6'-triisopropylbiphenyl.

In another preferred embodiment, in a suitable solvent, reacting compound 5 with compound 6 in the presence of a suitable base to obtain compound 7, subjecting compound 7 to a reductive amination reaction to obtain compound 8; reacting compound 8 with bis(pinacolato)diboron to obtain boron ester compound 9 in the presence of a palladium catalyst, then reacting compound 9 with compound 8 under standard Suzuki reaction conditions to obtain compound 10.

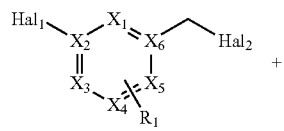

5

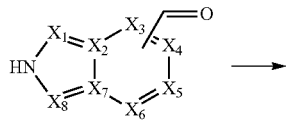

6

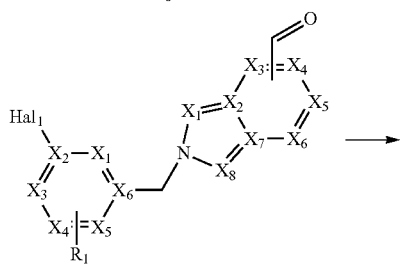

7

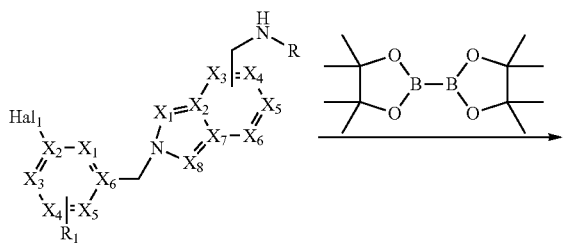

8

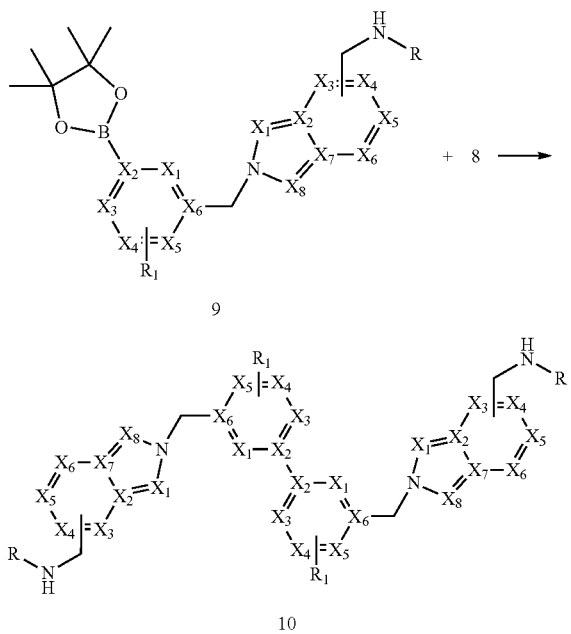

In another preferred embodiment, the solvent is selected from N, N-dimethylformamide, tetrahydrofuran, 1,4-dioxane, and toluene;

In another preferred embodiment, the base is selected from the group consisting of sodium hydride, potassium carbonate, potassium acetate, sodium carbonate, and potassium phosphate;

In another preferred embodiment, the palladium catalyst is selected from palladium acetate, (1,1'-bis (diphenylphosphino)ferrocene)palladium dichloride, and tetra (triphenylphosphine) palladium.

In another preferred embodiment, in an appropriate solvent, in the presence of a base and a phosphine compound, reacting compound 11 with compound 12 under the action of a palladium catalyst to obtain compound 13; then subjecting the compound 13 to a reductive amination reaction to obtain compound 14.

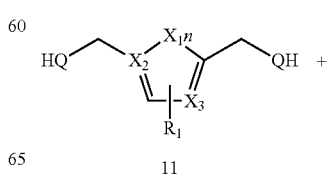

11

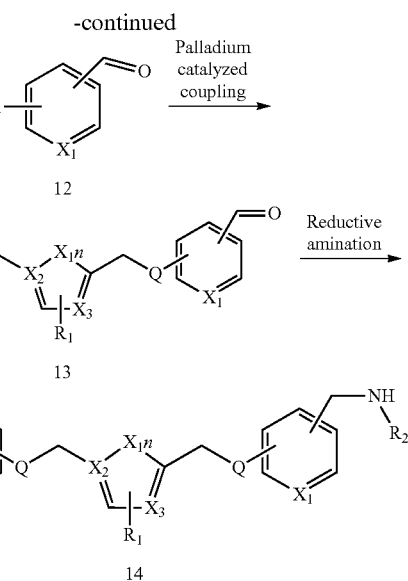

In another preferred embodiment, the solvent is selected from toluene, 1,4-dioxane, N,N-dimethylformamide;

In another preferred embodiment, the palladium catalyst is selected from palladium acetate; In another preferred embodiment, the base is selected from cesium carbonate and potassium phosphate;

In another preferred embodiment, the phosphine compound is selected from 2-di(tert-butylphosphino)-2',4',6'-triisopropylbiphenyl.

The definition of each group is as described above.

In the fourth aspect of the present invention, a use of the compound, a stereoisomer or a pharmaceutically acceptable salt thereof according to the first aspect of the present invention, or the composition according to the second aspect of the present invention in the preparation of a medicament for treating or preventing a disease related to PD-L1 is provided, wherein, the use comprises:

(1) For the treatment of various tumors, comprising but not limited to melanoma (such as metastatic malignant melanoma), kidney cancer (such as clear cell carcinoma), prostate cancer (such as hormone refractory prostate adenocarcinoma), breast cancer, colon cancer, and lung cancer (e.g., non-small cell lung cancer). Bone cancer, pancreatic cancer, skin cancer, head or neck cancer, skin or eye malignant melanoma, uterine cancer, ovarian cancer, rectal cancer, anal cancer, gastrointestinal, testicular cancer, fallopian tube cancer, endometrial cancer, cervical cancer, vaginal cancer, vulvar cancer, Hodgkin's disease, non-Hodgkin's lymphoma, esophageal cancer, small intestine cancer, endocrine system cancer, thyroid cancer, parathyroid cancer, adrenal cancer, soft tissue sarcoma, urethral cancer, penis cancer, chronic or acute leukemia (comprising acute myeloid leukemia, chronic myeloid leukemia, acute lymphoblastic leukemia, chronic lymphocytic leukemia), childhood solid tumor, lymphocytic lymphoma, bladder cancer, kidney or ureter cancer, renal pelvis cancer, central nervous system (CNS) neoplasm/tumor, primary CNS lymphoma, tumor angiogenesis, spinal axis tumor, brain stem glioma, pituitary adenoma, Kaposi's sarcomas, epidermoid carcinomas, squamous cell carcinomas, T-cell lymphomas, environmentally induced cancers (including those caused by asbestos), and combinations therefore. Metastatic cancer, especially metastatic cancer expressing PD-L1.

(2) For combined therapy regimen, such as combined tumor chemotherapy regimen, other tumor immunotherapeutics (small molecule compounds and antibodies, etc.), radiotherapy regimen, tumor-targeted drugs, tumor vaccines, etc, such as human papilloma virus (HPV), hepatitis virus (HBV and HCV) and Kaposi herpes sarcoma virus (KHSV). The agents may be administered before, after or at the same time or may be co-administered with other known therapies.

(3) For the treatment of patients exposed to specific toxins or pathogens, used alone or in combination, which comprises but are not limited to the treatment of various viruses, pathogenic bacteria, pathogenic fungi, pathogenic parasites, etc. Such as HIV, hepatitis virus (A, B, C), influenza virus, herpes virus, Giardia, malaria, *Leishmania, Staphylococcus aureus, Pseudomonas aeruginosa* and other established infections.

(4) For inducing therapeutic autoimmune response to treat patients with inappropriate accumulation of other autoantigens, such as amyloid deposits, comprising A β type of Alzheimer's disease, cytokines such as TNFα and IgE.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through extensive and in-depth research, the present inventors unexpectedly discovered it for the first time. The present invention is completed on this basis.

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes all the values between 99 and 101 and (eg, 99.1, 99.2, 99.3, 99.4, etc.).

As used herein, the terms "containing" or "comprise (comprising)" can be opened form, semi-closed form, or closed form. In other words, the terms also include situations such as "essentially consisting of . . . " or "consisting of . . . "

Group Definitions

The definition of standard chemical terms can be found in references (including Carey and Sundberg "ADVANCED ORGANIC CHEMISTRY 4TH ED." Vols. A (2000) and B (2001), Plenum Press, New York). Unless otherwise indicated, conventional methods within the skill of the art, such as mass spectrometry, NMR, IR and UV/VIS spectroscopy and pharmacological methods are employed. Unless specifically defined, the terms relates to analytical chemistry, organic synthetic chemistry, and pharmaceutical and pharmaceutical chemistry used herein are known in the art. Standard techniques can be used in chemical synthesis, chemical analysis, pharmaceutical preparation, formulation and delivery, and treatment of patients. For example, the reaction can be carried out and purified according to the manufacturer's instructions for use of the kit, or by methods well known in the art or as described in the present invention. The above techniques and methods can generally be carried out according to conventional methods well known in the art, as described in the various summaries and more specific references cited and discussed in this specification. In the present specification, the group and its substituents can be selected by those skilled in the art to provide stable structural moieties and compounds.

When a substituent is described by a conventional chemical formula written from left to right, the comparable substituent obtained when the structural formula is written from right to left. For example, —CH$_2$O— is comparable with —OCH$_2$—.

The section headings used herein are for the purpose of organizing articles only and are not to be construed as limiting the subject matter. All documents or parts of the literature cited in this application, including but not limited to patents, patent applications, articles, books, operating manuals and papers, are hereby incorporated by reference in their entirety.

Certain chemical groups defined herein are preceded by a simplified symbol to indicate the total number of carbon atoms present in the group. For example, C1-C6 alkyl refers to an alkyl group as defined below having a total of from 1 to 6 carbon atoms. The total number of carbon atoms in the simplified symbol does not include carbon that may be present in the substituents of the group.

In addition to the foregoing, when used in the specification and claims of the present application, unless otherwise specifically indicated, the following terms have the meanings indicated below.

In the present application, the term "halogen" means fluoro, chloro, bromo or iodo.

"Hydroxy" means —OH.

"Hydroxyalkyl" means alkyl groups as defined below which is substituted by hydroxy group (—OH).

"Carbonyl" means —C(=O)— group.

"Nitro" means —NO$_2$.

"Cyano" means —CN.

"Amino" means —NH$_2$.

"Substituted amino" means amino substituted by one or two alkyl, alkylcarbonyl, arylalkyl, heteroarylalkyl as defined below, for example, monoalkylamino, dialkylamino, alkylamido, arylalkylamino, heteroarylalkylamino.

"Carboxyl" means —COOH.

In the present application, as a group or part of another group (for example, used in a group such as a halogen-substituted alkyl group), the term "alkyl" means a fully saturated straight or branched hydrocarbon chain group which consists only of carbon atoms and hydrogen atoms, and has, for example, 1 to 12 (preferably 1 to 8, more preferably 1 to 6) carbon atoms, and is bonded to the rest of the molecule by a single bond, for example, comprising but not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl and decyl. For the present invention, the term "alkyl" refers to alkyl containing 1-6 carbon atoms.

In the present application, as a group or part of another group, the term "heterocyclyl" means a stable 3- to 20-membered non-aromatic cyclic group consisted of 2 to 14 carbon atoms and 1 to 6 heteroatoms selected from nitrogen, phosphorus, oxygen and sulfur. Unless otherwise specifically indicated in the specification, heterocyclic group can be monocyclic, bicyclic, tricyclic or ring system with ever more cyclic, which can contain fused ring system, bridged ring system or spiro ring system; the nitrogen, carbon or sulfur atom can optionally be oxidized; the nitrogen atom can optionally be quaternized; and the heterocyclic group may be partially or fully saturated. The heterocyclic group may be bonded to the remaining part of the molecule via a carbon atom or a hetero atom through a single bond. In the heterocyclic group containing a fused ring, one or more of the rings may be aryl or heteroaryl group as defined below, provided that the site of attachment to the rest part of the molecule is a non-aromatic ring atom. For the purposes of the present invention, the heterocyclic group is preferably a stable 4 to 11 membered non-aromatic monocyclic, bicyclic, bridged or spiro group containing 1-3 heteroatoms selected from nitrogen, oxygen and sulfur. More preferably, it is a stable 4- to 8-membered non-aromatic monocyclic, bicyclic, and bridged or spiro group containing 1-3 heteroatoms selected from nitrogen, oxygen and sulfur. Examples of heterocyclic groups comprises, but are not limited to, pyrrolidinyl, morpholinyl, piperazinyl, homopiperazinyl, piperidinyl, thiomorpholinyl, 2,7-diaza-spiro[3.5]nonane-7-yl, 2-oxa-6-aza-spiro[3.3]heptane-6-yl, 2,5-diaza-bicyclo[2.2.1]heptan-2-yl, aza-cyclobutane, pyranyl, tetrahydropyranyl, thiapyranyl, tetrahydrofuranyl, oxazinyl, dioxocyclopentyl, tetrahydroisoquinolinyl, decahydroisoquinolinyl, imidazolinyl, imidazolidinyl, quinazolidinyl, thiazolidinyl, isothiazolidinyl, isoxazolidinyl, dihydroindolyl, octahydroindolyl, octahydroisodolyl, pyrrolidinyl, pyrazolidinyl, phthalimidoyl and the like.

In the present application, as a group or part of another group, the term "aryl" means a conjugated hydrocarbon ring system group having 6 to 18 carbon atoms, preferably having 6 to 10 carbon atoms. For the purposes of the present invention, an aryl group can be a monocyclic, bicyclic, tricyclic or ring system of even more cyclic, and can also be fused to the cycloalkyl or heterocyclic group as defined above, provided that the aryl group is connected to the rest of the molecule by a single bond via atoms on the aromatic ring. Examples of aryl groups comprise, but are not limited to, phenyl, naphthyl, anthracenyl, phenanthryl, fluorenyl, 2,3-dihydro-1H-isoindolyl, 2-benzoxazolinone, 2H-1,4-benzoxazine-3(4H)-keto-7-yl, and the like.

In the present application, the term "arylalkyl" refers to alkyl groups as defined above substituted by aryl groups as defined above.

In the present application, as a group or part of another group, the term "heteroaryl" means a conjugated hydrocarbon ring system group having 1 to 15 carbon atoms (preferably having 1 to 10 carbon atoms) and 1 to 6 heteroatoms selected from nitrogen, oxygen and sulfur. Unless otherwise indicated in the present invention, a heteroaryl group can be a monocyclic, bicyclic, tricyclic or ring system of even more cyclic, and can also be fused to a cycloalkyl or heterocyclic group as defined above, provided that the aryl group is connected to the rest of the molecule by a single bond via atoms on the aromatic ring. The nitrogen, carbon or sulfur atom in the heteroaryl group can be optionally oxidized; and the nitrogen atom can optionally be quaternized. For the purposes of the present invention, the heterocyclic group is preferably a stable 5 to 12 membered aromatic group containing 1-5 heteroatoms selected from nitrogen, oxygen and sulfur. More preferably, it is a stable 5- to 10-membered aromatic group containing 1-3 heteroatoms selected from nitrogen, oxygen and sulfur, or 5- to 6-membered aromatic group containing from 1 to 3 heteroatoms selected from nitrogen, oxygen and sulfur Examples of heteroaryl groups comprise, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolyl, isoquinolyl, diazonaphthyl, naphthyridinyl, quinoxalinyl, pteridinyl, carbazolyl, carboline, phenanthridinyl, phenanthrolinyl, acridinyl, phenazinyl, isothiazolyl, benzothiazolyl, benzothienyl, oxatriazole, cinnolinyl, quinazolinyl, phenylthio, purrocolinyl, orthophenanthrolenyl, isoxazolyl, phenoxazinyl, phenothiazine, 4,5,6,7-tetrahydrobenzo[b]thienyl, naphthopyridyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, etc.

In the present application, the term "heteroarylalkyl" refers to alkyl groups as defined above which is substituted by heteroaryl groups as defined above.

In the present application, "optional" or "optionally" means that the subsequently described event or condition may or may not occur, and that the description includes both the occurrence and non-occurrence of the event or condition. For example, "optionally substituted aryl" means that the aryl is substituted or unsubstituted, and the description includes both the substituted aryl and the unsubstituted aryl. The "optionally" substituents described in the claims and the specification of the present invention are selected from the group consisting of alkyl, alkenyl, alkynyl, halogen, haloalkyl, haloalkenyl, haloalkynyl, cyano, nitro, optionally substituted aryl, optionally substituted heteroaryl, optionally substituted cycloalkyl, optionally substituted heterocyclic hydrocarbon group.

The terms "part", "structural moiety", "chemical moiety", "group", and "chemical group", as used herein, refer to a particular fragment or functional group in a molecule. A chemical moiety is generally considered to be a chemical entity that is embedded or attached to a molecule.

"Stereoisomer" refers to a compound composed of the same atom, bonded by the same bond, but having a different three-dimensional structure. The invention will cover various stereoisomers and mixtures thereof.

When the compound of the present invention contains olefinic double bonds, the compounds of the present invention are intended to comprise E- and Z-geometric isomers unless otherwise stated.

"Tautomer" refers to an isomer formed by the transfer of a proton from one atom of a molecule to another atom of the same molecule. All tautomeric forms of the compounds of the invention will also be included within the scope of the invention.

The compounds of the invention, or pharmaceutically acceptable salts thereof, can contain one or more chiral carbon atoms and, thus, can produce enantiomers, diastereomers, and other stereoisomeric forms. Each chiral carbon atom can be defined as (R)- or (S)-based on stereochemistry. The invention is intended to include all possible isomers, as well as racemic and optically pure forms thereof. Racemates, diastereomers or enantiomers may employed as starting materials or intermediates in the preparation of the compounds of the invention. Optically active isomers can be prepared by chiral synthons or chiral reagents, or resolved using conventional techniques, such as by crystallization and chiral chromatography.

Conventional techniques for the preparation/isolation of individual isomers include chiral synthesis from a suitable optically pure precursor, or resolution of the racemate (or racemic form of a salt or derivative) using, for example, chiral high performance liquid chromatography. For example, see Gerald Gübitz and Martin G. Schmid (Eds.), Chiral Separations, Methods and Protocols, Methods in Molecular Biology, Vol. 243, 2004; AM Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem Res. 1990, 23, 128.

In the present application, the term "pharmaceutically acceptable salt" comprises pharmaceutically acceptable acid addition salts and pharmaceutically acceptable base addition salts.

"Pharmaceutically acceptable acid addition salt" means a salt formed with an inorganic or organic acid which retains the bioavailability of the free base without bringing other side effects. Inorganic acid salts comprise, but are not limited to, hydrochlorides, hydrobromides, sulfates, nitrates, phosphates, and the like; organic acid salts comprise, but are not limited to, formate, acetate, 2,2-dichloroacetate, trifluoroacetate, propionate, hexanoate, octoate, decanoate, undecylenate, glycolate, gluconate, lactate, sebacate, adipates, glutaric acid salts, malonates, oxalates, maleates, succinates, fumarates, tartrates, citrates, palmitates, stearates, oleates, cinnamate, laurate, malate, glutamate, pyroglutamate, aspartate, benzoate, methanesulfonate, benzenesulfonate, p-toluenesulfonate, alginate, ascorbate, salicylate, 4-aminosalicylate, naphthalene disulfonate, and the like. These salts can be prepared by methods known in the art.

"Pharmaceutically acceptable base addition salt" means a salt formed with an inorganic or organic base capable of maintaining the bioavailability of the free acid without bringing other side effects. Salts derived from inorganic bases comprise, but are not limited to, sodium salts, potassium salts, lithium salts, ammonium salts, calcium salts, magnesium salts, iron salts, zinc salts, copper salts, manganese salts, aluminum salts, and the like. Preferred inorganic salts are ammonium, sodium, potassium, calcium and magnesium salts. Salts derived from organic bases comprise, but are not limited to, the following salts: primary amines, secondary amines and tertiary amines, substituted amines, containing naturally substituted amines, cyclic amines, and basic ion exchange resins. For example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, bicyclo hexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, and the like. Preferred organic bases comprise isopropylamine, diethylamine, ethanolamine, trimethylamine, dicyclohexylamine, choline, and caffeine. These salts can be prepared by methods known in the art.

In the present application, "pharmaceutical composition" refers to a formulation of a compound of the invention and a medium generally accepted in the art for delivery of a biologically active compound to a mammal, such as a human. The medium comprises pharmaceutically acceptable carriers. The purpose of the pharmaceutical composition is to promote the administration of the organism, thus facilitating the absorption of the active ingredients and thereby exerting the biological activity.

The term "pharmaceutically acceptable" as used herein, refers to a substance (such as a carrier or diluent) that does not affect the biological activity or properties of the compound of the invention, and is relatively non-toxic, i.e., the substance can be administered to an individual without causing undesirable organisms, or interacts with any of the components contained in the composition in an undesirable manner.

In the present application, "pharmaceutically acceptable excipients" comprise, but are not limited to, any adjuvants, carriers, excipients, glidants, sweeteners, diluents, preservatives, dyes/colorants, flavoring agents, surfactants, wetting agents, dispersing agents, suspending agents, stabilizers, isotonic agents, solvents or emulsifiers approved by the relevant government authorities for acceptable use in humans or domestic animals.

The "tumor" of the present invention comprises, but is not limited to, glioma, sarcoma, melanoma, articular chondrocarcinoma, cholangiocarcinoma, leukemia, gastrointestinal stromal tumor, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell carcinoma, cervical cancer, ovarian cancer, intestinal cancer, nasopharyngeal cancer, brain cancer, bone cancer, esophageal cancer, melanin tumor, kidney cancer, oral cancer and other diseases.

The terms "prevention", "preventing" and "prevented" as used herein comprise the possibility of reducing the occurrence or progression of a disease or condition by a patient.

The term "treatment" and other similar synonyms as used herein comprises the following meanings:
(i) preventing the occurrence of a disease or condition in a mammal, particularly when such a mammal is susceptible to the disease or condition, but has not been diagnosed as having the disease or condition;
(ii) inhibiting a disease or condition, i.e., inhibiting its development;
(iii) alleviating the disease or condition, i.e., degrading the condition of the disease or illness; or
(iv) alleviating the symptoms caused by the disease or condition.

The term "effective amount," "therapeutically effective amount," or "pharmaceutically effective amount," as used herein, refers to an amount of at least one agent or compound that, after administration, is sufficient to alleviate one or more symptoms of the disease or condition being treated to some extent. The result can be reduction and/or alleviation of signs, symptoms or causes, or any other desired change in the biological system. For example, an "effective amount" for treatment is an amount of a composition comprising a compound disclosed herein that is required to provide a significant conditional relief effect in clinic. An effective amount suitable for any individual case can be determined using techniques such as dose escalation testing.

The terms "take", "administrate", "apply" and the like, as used herein, refers to a method of delivering compound or composition to a desired site for biological action. These methods comprise, but are not limited to, oral, duodenal, parenteral injection (including intravenous, subcutaneous, intraperitoneal, intramuscular, intra-arterial injection or infusion), topical administration, and rectal administration. The techniques of administration of the compounds and methods described herein are well known to those skilled in the art, for example, those discussed in Goodman and Gilman, The Pharmacological Basis of Therapeutics, current edition; Pergamon; and Remington's, Pharmaceutical Sciences (current edition), Mack Publishing Co., Easton, Pa. In a preferred embodiment, the compounds and compositions discussed herein are administered orally.

The terms "pharmaceutical combination", "drug combination", "combination", "administering other treatments", "administering other therapeutic agents" and the like, as used herein, mean a pharmaceutical treatment obtained by mixing or combining more than one active ingredient which includes both fixed and unfixed combinations of active ingredients. The term "fixed combination" refers to simultaneous administrating at least one compound described herein and at least one synergistic agent to a patient in the form of a single entity or a single dosage form. The term "unfixed combination" refers to simultaneous administrating, administrating in combination or sequentially administrating in variable interval time at least one of the compounds described herein and at least one synergistic formulation to the patient in the form of separate entities. These can also be applied to cocktail therapy, for example, administrating three or more active ingredients.

It will also be understood by those skilled in the art that in the methods described below, the intermediate compound functional groups may need to be protected by suitable protecting groups. Such functional groups comprise hydroxyl group, amino group, thiol group, and carboxyl. Suitable hydroxy protecting groups comprise trialkylsilyl or diarylalkylsilyl (e.g., tert-butyldimethylsilyl, tert-butyldiphenylsilyl or trimethylsilyl), tetrahydropyranyl, benzyl, etc. Suitable protecting groups for amino, amidino and guanidino comprise t-butoxycarbonyl, benzyloxycarbonyl, and the like. Suitable thiol protecting groups include —C(O)—R" (wherein R" is alkyl, aryl or aralkyl), p-methoxybenzyl, trityl, and the like. Suitable carboxy protecting groups comprise alkyl, aryl or aralkyl esters.

Protecting groups can be introduced and removed according to standard techniques known to those skilled in the art and as described herein. The use of protecting groups is described in detail in Greene, T. W. and P. G. M. Wuts, Protective Groups in Organi Synthesis, (1999), 4th Ed., Wiley. The protecting group can also be polymeric resins.

Compound of Formula I

In the first aspect of the present invention, a compound of formula I, or a stereoisomer, a racemate or a pharmaceutically acceptable salt thereof is provided,

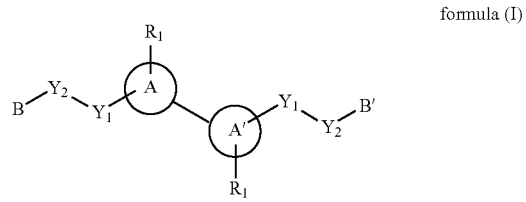

formula (I)

wherein,
The A ring and A' ring are each independently selected from the group consisting of none, substituted or unsubstituted 5-6 membered aryl ring, substituted or unsubstituted 5-7 membered saturated or unsaturated heterocyclic ring, substituted or unsubstituted 7-10 membered heterospiro ring, substituted or unsubstituted 6-10 membered heterocyclic fused substituted or unsubstituted 5-10 membered heteroaromatic ring; and the heterocyclic ring has 1-3 heteroatoms selected from S, O or N; and A ring and A' ring cannot be absent simultaneously;

$R_1$ is selected from the group consisting of H, —CN, —OH, halogen, substituted or unsubstituted C1-C4 alkyl, substituted or unsubstituted C1-C4 alkoxy; and the "substituted" means having the one or more (such as 1, 2, or 3) substituents selected from halogen, and substituted or unsubstituted phenoxy;

$Y_1$ is selected from carbonyl, 0, S, amino, substituted or unsubstituted C1-C4 alkyl, substituted or unsubstituted 5-10 membered heteroaryl; and the heteroaryl has 1-4 heteroatoms selected from N or O;

$Y_2$ is selected from O, S, N, substituted or unsubstituted amido, sulfonamido, substituted or unsubstituted C1-C4 alkyl, substituted or unsubstituted 5-10 membered aromatic group, substituted or unsubstituted 5-10 membered heteroaryl and the heteroaryl has 1-3 heteroatoms selected from S, O or N; and $Y_1$ and $Y_2$ cannot be heteroatoms simultaneously;

B and B' are each independently selected from the group consisting of none, H, substituted or unsubstituted amino, substituted or unsubstituted C1-C4 alkylamino, substituted or unsubstituted 5-10 membered aryl, substituted or unsubstituted 5-10 membered heteroaryl, and the heteroaryl has 1-3 heteroatoms selected from S, O, N, substituted or unsubstituted —NH—C(=O)—, substituted or unsubstituted C1-C4 alkyl; and the B ring and B' ring cannot be absent at the same time; and the "substituted" means having one or more (such as 1, 2, 3 or 4) substituents selected from the group Z:

group Z substituents are selected from the group consisting of H, substituted or unsubstituted C1-C4 alkylamino, substituted or unsubstituted C1-C4 alkyl, substituted or unsubstituted C1-C4 alkoxy; and the "substituted" means having one or more (such as 1, 2, 3, or 4) substituents selected from the Z' group; wherein the Z' substituent is selected from: substituted or unsubstituted 5-7 membered aryl, C1-C4 alkylamino, substituted or unsubstituted C1-C4 alkyl, methylcarbonyl, substituted or unsubstituted 5-6 membered saturated carbocyclic ring, substituted or unsubstituted 5-7 membered saturated heterocyclic group, substituted or unsubstituted 5-7 membered heteroaryl, and the heteroaryl or heterocyclic group has 1-3 heteroatoms selected from S, O and N;

and, in the A ring, A' ring, $Y_1$-$Y_2$ and Z' substituents, the "substituted" means substituted by groups selected from the group consisting of —OH, —CN, —COOH, —O—, aminocarbonyl, C1-C4 alkyl, hydroxy C1-C4 alkyl,

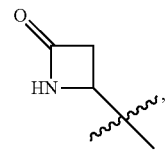

C1-C4 alkylcarbonyl;

and the compound of formula I is other than compounds selected from the group consisting of:

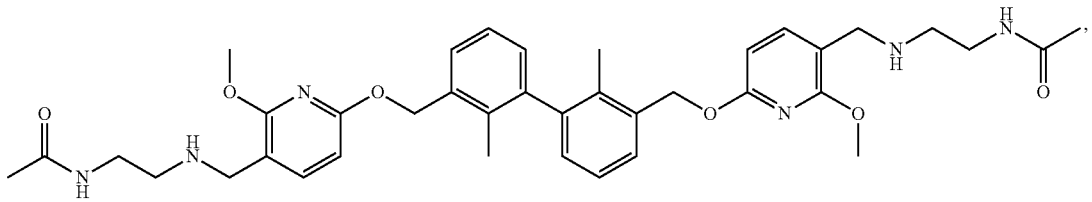

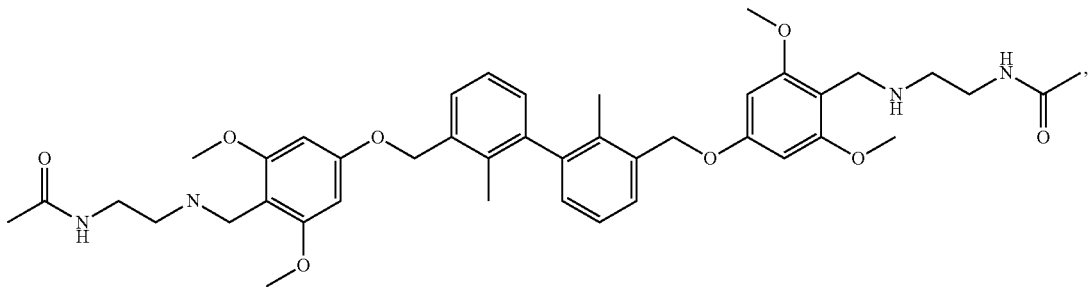

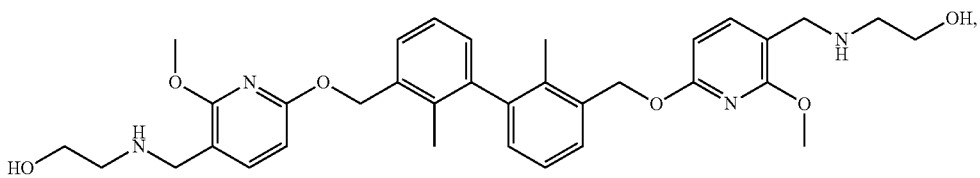

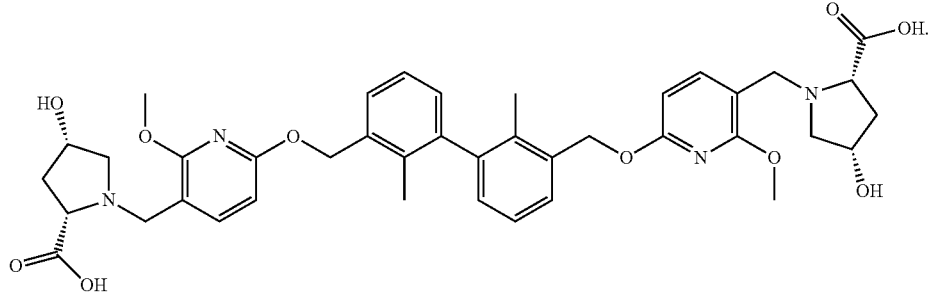

In another preferred embodiment, the compound of formula I is compound 1 to compound 82 described in the examples.

The Preparation of Compound of Formula I

The following reaction scheme exemplarily illustrates a method for preparing the compound of formula I, a stereoisomer or a mixture thereof, or a pharmaceutically acceptable salt thereof, wherein each group is as described in the embodiment section of the compound of formula I above. It should be understood that in the following reaction schemes, combinations of substituents and/or variables in the general formula are only permissible if such combinations result in stable compounds. It should also be understood that other general formulas, such as the general formulae (Ia), (Ib), (Ic), (Id), and other compounds of formula I specifically disclosed herein can be prepared by those skilled in the art of organic chemistry through the methods disclosed herein (by applying appropriately substituted starting materials and modifying the synthesis parameters corresponding to the need) or methods known by those skilled in the art.

The invention provides a method for preparing the compound according to the invention, which comprising the steps:

In a suitable solvent, reacting compound 1 (wherein Q is selected from 0 or N) with compound 2 (n=1, 2) under the action of a palladium catalyst and in the presence of a base and a phosphine compound to afford compound 3; then subjecting compound 3 to a reductive amination reaction to obtain the compound of formula 4.

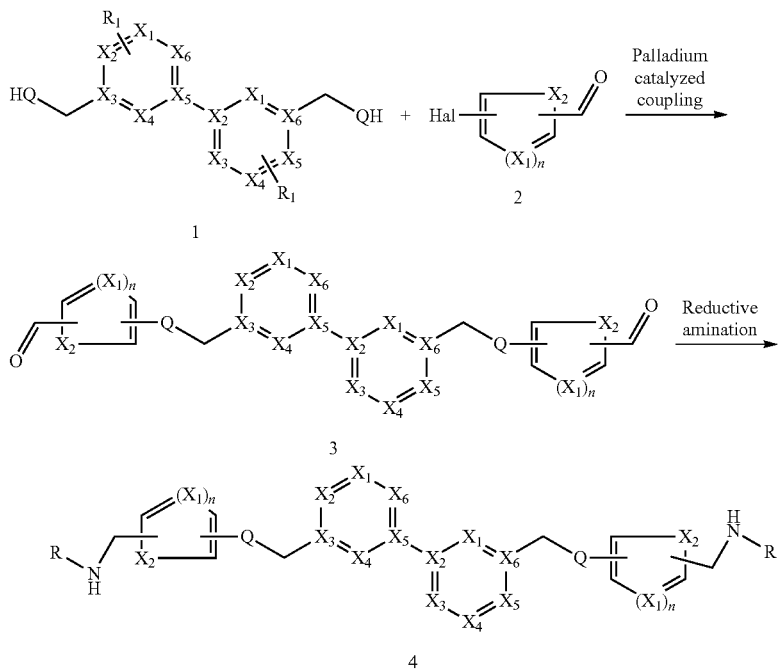

In another preferred embodiment, the solvent is selected from toluene, 1,4-dioxane, and N,N-dimethylformamide;

In another preferred embodiment, the palladium catalyst is selected from palladium acetate;

In another preferred embodiment, the base is selected from cesium carbonate and potassium phosphate;

In another preferred embodiment, the phosphine compound is selected from 2-di(tert-butylphosphino)-2',4',6'-triisopropylbiphenyl.

In another preferred embodiment, in a suitable solvent, reacting compound 5 with compound 6 in the presence of a suitable base to obtain compound 7, subjecting compound 7 to a reductive amination reaction to obtain compound 8; reacting compound 8 with bis(pinacolato)diboron to provide boron ester compound 9 in the presence of a palladium catalyst, then reacting compounds 9 with compound 8 under standard Suzuki reaction conditions to provide compound 10.

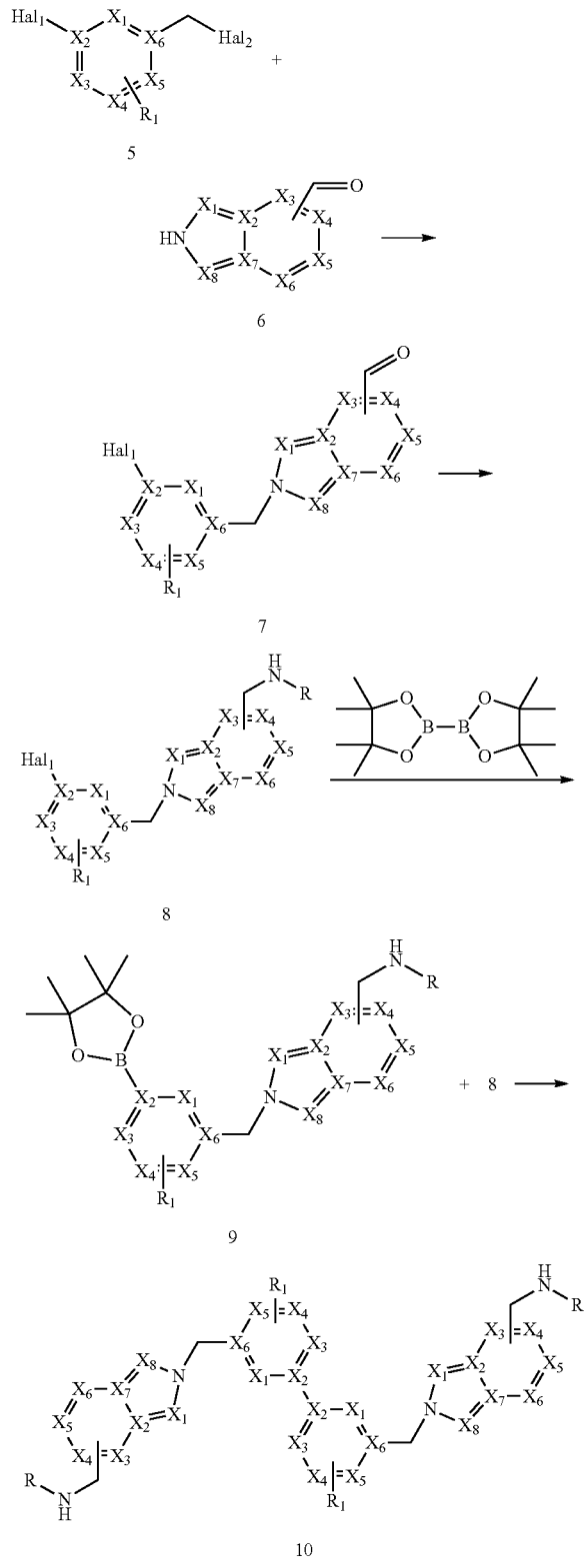

In another preferred embodiment, the solvent is selected from N, N-dimethylformamide, tetrahydrofuran, 1,4-dioxane, and toluene;

In another preferred embodiment, the base is selected from the group consisting of sodium hydride, potassium carbonate, potassium acetate, sodium carbonate, and potassium phosphate;

In another preferred embodiment, the palladium catalyst is selected from palladium acetate, (1,1'-bis (diphenylphosphino)ferrocene)palladium dichloride, and tetra (triphenylphosphine) palladium.

In another preferred embodiment, in an appropriate solvent, reacting compound 11 with compound 12 under the action of a palladium catalyst and in the presence of a base and a phosphine compound to obtain compound 13; then subjecting compound 13 to a reductive amination reaction to obtain compound 14.

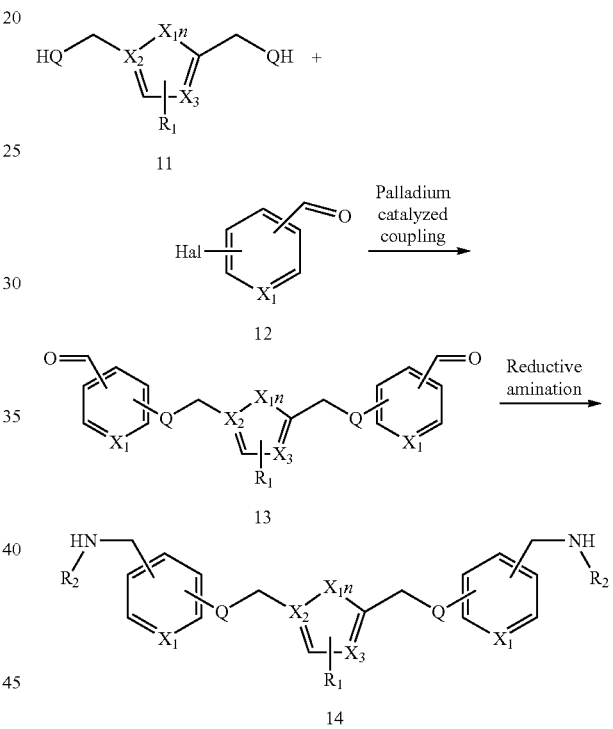

In another preferred embodiment, the solvent is selected from toluene, 1,4-dioxane, and N,N-dimethylformamide;

In another preferred embodiment, the palladium catalyst is selected from palladium acetate;

In another preferred embodiment, the base is selected from cesium carbonate and potassium phosphate;

In another preferred embodiment, the phosphine compound is selected from 2-di(tert-butylphosphino)-2',4',6'-triisopropylbiphenyl.

The definition of each group is as described above.

The main advantages of the present invention are:
1. Providing a compound of formula I.
2. Providing a pharmaceutical composition with novel structure for preventing and treating PD-L1-related diseases.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

In each example:
Analysis Method I
LCMS instrument: Agilent 6110, UV detector: G1315D
Chromatographic column: Xbridge C18 3.0×50 mm, 2.5 uM, column temperature 30° C.
Mobile phase: A: H$_2$O (0.05% TFA), B: acetonitrile, gradient elution: 0-1 minute 10% B, 1-8 minutes 10-95% B, 9 minute 95% B Synthesis of Intermediate A (2,2'-dimethyl-[1,1'-biphenyl]-3,3'-diyl) dimethanol

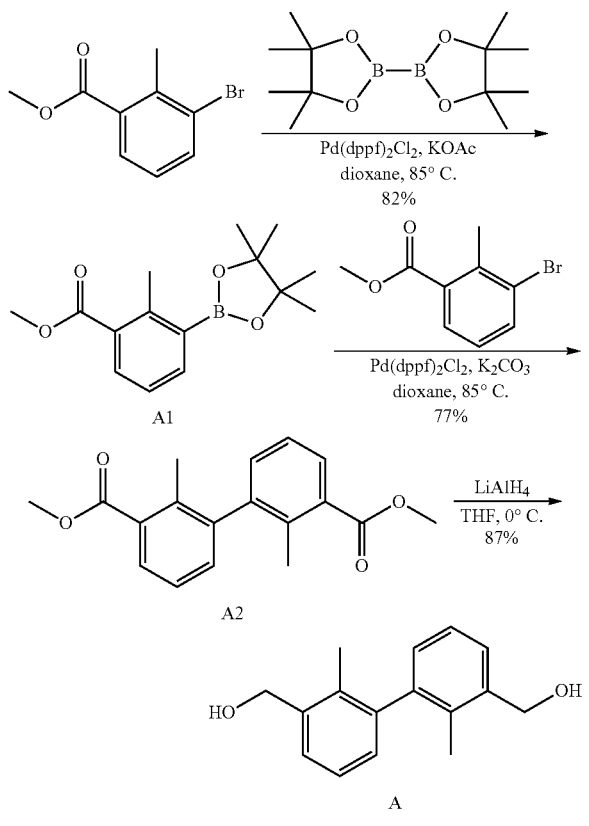

Methyl 2-methyl-3-(4,4,5,5-tetramethyl-1,3,2-dioxoborolan-2-yl) benzoate

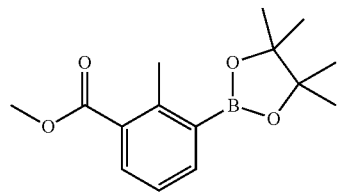

To methyl 3-bromo-2-methylbenzoate (10.0 g, 43.7 mmol), bis(pinacolato)diboron (33.3 g, 131 mmol), potassium acetate (9.0 g, 91.7 mmol) in dioxane (100 mL), 1,4-[1,1-bis (diphenylphosphine) ferrocene] palladium dichloride-dichloromethane complex (3.2 g, 4.37 mmol) was added, and the mixture was reacted under argon atmosphere in sealed vessel at 85° C. for 3 hours. The cooled reaction mixture was diluted with water, extracted with ethyl acetate, dried over anhydrous sodium sulfate, then filtered and concentrated. The crude product was purified with a silica gel column (eluted with ethyl acetate) to obtain the target compound A1 (10.0 g, 82%) as a yellow oil.

$^1$H NMR (400 MHz, DMSO-d$_6$) δ 7.87-7.82 (m, 2H), 7.26-7.19 (m, 1H), 3.88 (s, 3H), 2.74 (s, 3H), 1.35 (s, 12H).

Dimethyl 2,2'-dimethyl-[1,1'-biphenyl]-3,3'-dicarboxylate

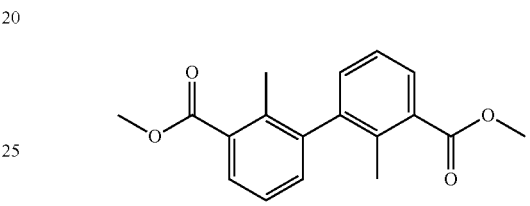

To methyl 3-bromo-2-methylbenzoate (9.1 g, 39.8 mmol), intermediate A1 (10.0 g, 36.2 mmol), and potassium carbonate (10.1 g, 72.4 mmol) in dioxane (100 mL), 1,4-[1,1-bis (diphenylphosphine) ferrocene] palladium dichloride-dichloromethane complex (2.6 g, 3.6 mmol) was added, and the mixture was reacted under argon atmosphere in sealed vessel at 85° C. for 5 hours. The cooled reaction mixture was diluted with water, extracted with ethyl acetate, dried over anhydrous sodium sulfate, then filtered and concentrated. The crude product was purified with a silica gel column chromatography (eluted with petroleum ether/ethyl acetate=100/1) to give the target compound A2 (8.4 g, 77%) as a yellow solid.

(2,2'-dimethyl[1,1'-biphenyl]-3,3'-diyl) dimethanol

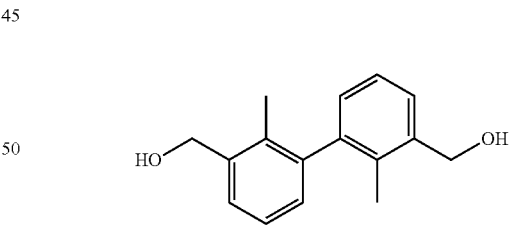

Under ice bath, lithium aluminum hydrogen (3.2 g, 84.5 mmol) was slowly added to a solution of the intermediate A2 (8.4 g, 28.2 mmol) in tetrahydrofuran (100 mL), and the mixture was stirred for 1 hour at 0° C. The mixture was quenched with water, extracted with ethyl acetate, dried over anhydrous sodium sulfate, then filtered and concentrated. The crude product was purified by silica gel column chromatography (eluted with petroleum ether/ethyl acetate=10/1) to give the target compound A (6.0 g, 87%) as a white solid.

$^1$H NMR (400 MHz, DMSO-d$_6$) δ 7.39 (d, J=7.2 Hz, 2H), 7.21 (dd, J=7.2, 7.2 Hz, 2H), 6.93 (d, J=7.2 Hz, 2H), 5.14-5.10 (brs, 2H), 4.54 (s, 4H), 1.90 (s, 6H).

Example 1

2,2,2-trifluoro-N-((6-((3'-(hydroxymethyl)-2,2'-dimethyl-[1,1'-biphenyl]-3-yl)methoxy)-2-methoxypyridin-3-yl)methyl)acetamide

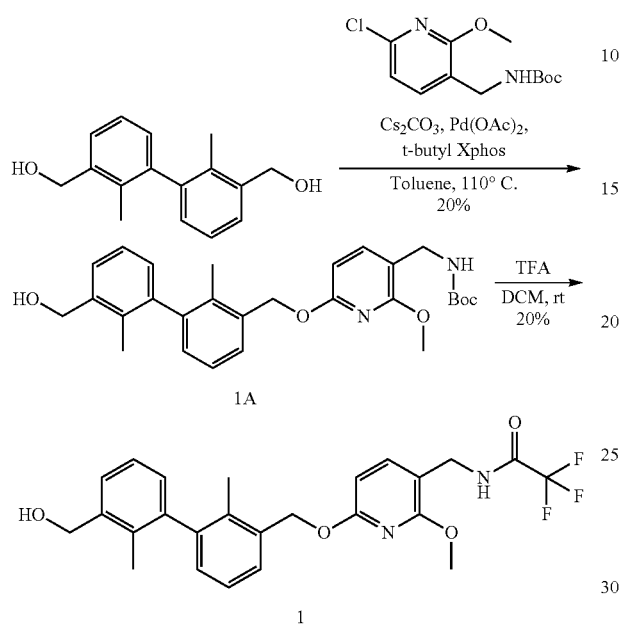

Tert-butyl((6-((3'-(hydroxymethyl)-2,2'-dimethyl-[1,1'-biphenyl]-3-yl)methoxy)-2-methoxypyridin-3-yl)methyl)carbamate

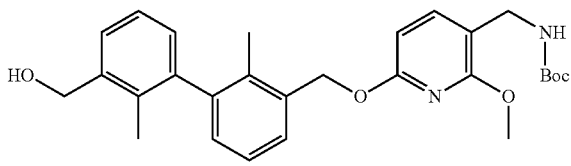 [SMILES: COc1nc(OCc2cccc(-c3cccc(CO)c3C)c2C)ccc1CNC(=O)OC(C)(C)C]

To intermediate A (50.0 mg, 0.20 mmol), tert-butyl ((6-chloro-2-methoxypyridin-3-yl)methyl)carbamate (56.0 mg, 0.20 mmol), cesium carbonate (134.0 mg, 0.41 mmol) in toluene (1 mL), palladium acetate (4.6 mg, 0.02 mmol) and 2-di-tert-butylphosphino-2',4',6'-triisopropylbiphenyl (17.5 mg, 0.041 mmol) were added, the mixture was exchanged with nitrogen for 3 minutes and heated to 110° C. to react overnight under argon atmosphere in sealed vessel. The reaction mixture was filtered through celite, the filtrate was concentrated, and the residue was separated and purified with Prep-TLC (petroleum ether/ethyl acetate=4/1) to obtain the target compound (20.0 mg, 20%) as a yellow oil.

MS (ESI): m/z=479.3 [M+H]$^+$.

$^1$H NMR (400 MHz, DMSO-d$_6$) δ 7.47-7.33 (m, 3H), 7.22-7.14 (m, 3H), 6.99 (d, J=7.5 Hz, 1H), 6.93 (d, J=7.5 Hz, 1H), 6.40 (d, J=8.0 Hz, 1H), 5.41-5.31 (m, 2H), 5.09 (t, J=5.4 Hz, 1H), 4.50 (t, J=7.1 Hz, 2H), 3.95 (d, J=5.8 Hz, 2H), 3.84 (s, 3H), 1.96 (s, 3H), 1.86 (s, 3H), 1.35 (s, 7H).

2,2,2-trifluoro-N-(((6-((3'-(hydroxymethyl)-2,2'-dimethyl-[1,1'-biphenyl]-3-yl)methoxy)-2-methoxypyridin-3-yl)methyl)acetamide (Compound 1)

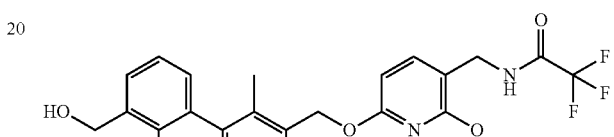

Under 0° C., trifluoroacetic acid (1 mL) was added to the solution of example 1A (20.0 mg, 0.041 mmol) in dichloromethane (4 mL), and the mixture was stirred at room temperature for 2 hours. The reaction mixture was concentrated, then water (5 mL) and dichloromethane (10 mL) were added. A saturated sodium bicarbonate solution was added to in portion adjust pH to 9. The organic layer was separated, washed with brine, dried (anhydrous sodium sulfate), filtered and concentrated. The residue was separated and purified by combiflash column chromatography (methanol/water) to obtain the target compound Example 1 (4.0 mg, 20%) as an orange solid.

MS (ESI): m/z=475.1 [M+H]$^+$.

$^1$H NMR (400 MHz, DMSO-d$_6$) δ 9.72 (s, 1H), 7.48 (d, J=8.1 Hz, 1H), 7.38 (dd, J=10.9, 7.5 Hz, 2H), 7.20 (dd, J=14.0, 7.3 Hz, 2H), 7.00 (d, J=6.5 Hz, 1H), 6.93 (d, J=7.0 Hz, 1H), 6.43 (d, J=8.0 Hz, 1H), 5.38 (s, 2H), 5.09 (t, J=5.4 Hz, 1H), 4.51 (d, J=5.0 Hz, 2H), 4.21 (s, 2H), 3.86 (s, 3H), 1.96 (s, 3H), 1.87 (s, 3H).

Example 2

N-(2-(((6-(3'-(hydroxymethyl)-2,2'-dimethyl-[1,1'-biphenyl]-3-yl)methoxy)-2-methoxypyridin-3-yl)methyl)amino)ethyl)acetamide

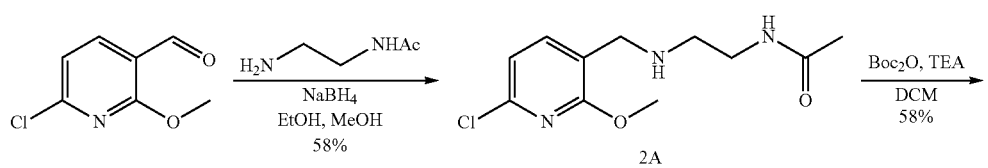

-continued

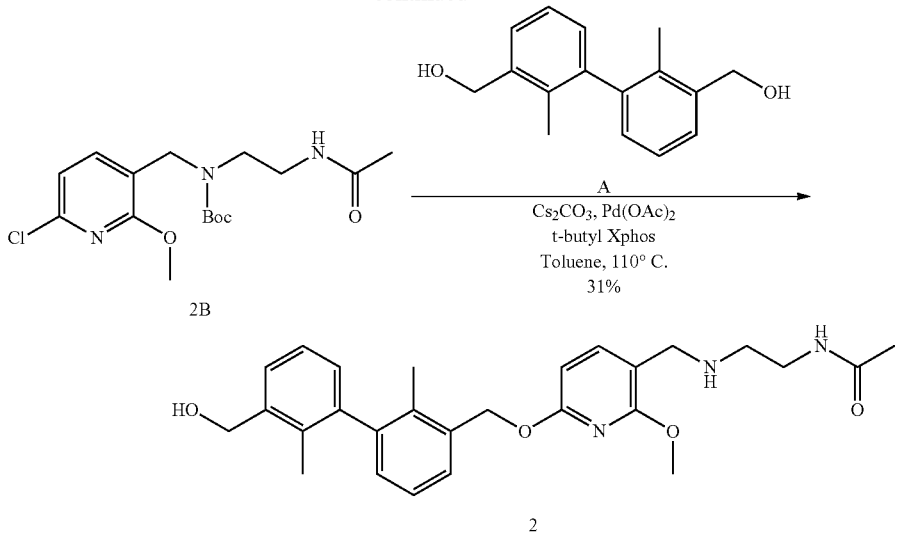

N-(2-(((6-chloro-2-methoxypyridin-3-yl)methyl)amino)ethyl)acetamide

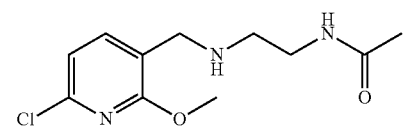 [SMILES: COc1nc(Cl)ccc1CNCCNC(C)=O]

6-chloro-2-methoxynicotyraldehyde (400.0 mg, 2.34 mmol) and N-(2-aminoethyl)acetamide (240.0 mg, 2.34 mmol) were mixed into ethanol (10 mL), and the mixture was stirred at reflux for 2 hours, then concentrated under reduced pressure. The crude product was redissolved in methanol (10 mL), sodium borohydride (89.0 mg, 2.34 mmol) was added in portions, the mixture was reacted under stirring at room temperature for 2 hours. The solvent was removed under reduced pressure, and the crude product was purified by silica gel column chromatography (eluted with dichloromethane/methanol from 50/1 to 10/1) to obtain compound 2A (350.0 mg, 58%).

$^1$H NMR (400 MHz, DMSO-$d_6$) δ 7.78 (brs, 1H), 7.73 (d, J=7.6 Hz, 1H), 7.06 (d, J=7.56 Hz, 1H), 3.88 (s, 3H), 3.61 (s, 2H), 3.15-3.10 (m, 2H), 2.54-2.50 (m, 2H), 1.79 (s, 3H).

Tert-butyl (2-acetylaminoethyl)((6-chloro-2-methoxypyridin-3-yl)methyl)carbamate

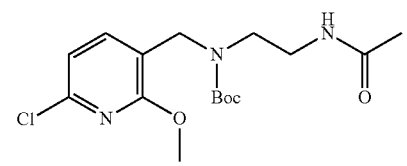 [SMILES: COc1nc(Cl)ccc1CN(CCNC(C)=O)C(=O)OC(C)(C)C]

In ice bath, di-tert-butyl dicarbonate (360.0 mg, 1.63 mmol) was added to a mixture of compound 2A (350.0 mg, 1.36 mmol) and triethylamine (10 mL) in dichloromethane (10 mL). The mixture was reacted under stirring at room temperature for 2 hours, then concentrated to afford crude product, and purified by silica gel column chromatography (eluted with dichloromethane/methanol=50/1) to give compound 2B (285.0 mg, 58%) as a colorless oil.

$^1$H NMR (400 MHz, DMSO-$d_6$) δ 7.89 (brs, 1H), 7.44 (d, J=7.6 Hz, 1H), 7.10 (d, J=7.6 Hz, 1H), 4.27 (s, 2H), 3.88 (s, 3H), 3.23-3.14 (m, 4H), 1.79 (s, 3H), 1.41 (s, 9H).

N-(2-(((6-(3'-(hydroxymethyl)-2,2'-dimethyl-[1,1'-biphenyl]-3-yl)methoxy)-2-methoxy pyridin-3-yl)methyl)amino)ethyl)acetamide (Compound 2)

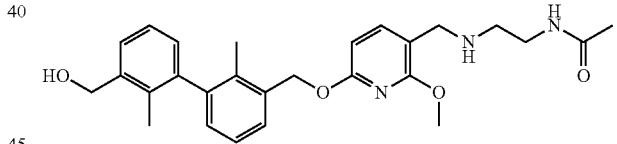

Palladium acetate (18.0 mg, 0.083 mmol) and 2-di-tert-butylphosphino-2',4',6'-triisopropylbiphenyl (70.0 mg, 0.165 mmol) were added to a mixture of intermediate A (200.0 mg, 0.83 mmol), compound 2B (295.0 mg, 0.83 mmol), cesium carbonate (538.0 mg, 1.65 mmol) and toluene (3 mL). The mixture was exchanged with nitrogen for 3 minutes, and reacted at 110° C. under nitrogen in sealed vessel overnight. The reaction mixture was filtered through celite, and the filtrate was concentrated. The residue was separated and purified with a combiflash column chromatography (methanol/water) to obtain the target compound example 2 (120.0 mg, 31%) as a yellow oil.

MS (ESI): m/z=362.1 [M-101]$^+$.

$^1$H NMR (400 MHz, DMSO-$d_6$) δ 7.86 (s, 1H), 7.40-7.36 (m, 3H), 7.22-7.17 (m, 2H), 6.99 (d, J=6.6 Hz, 1H), 6.93 (d, J=6.6 Hz, 1H), 6.42 (d, J=8.0 Hz, 1H), 5.37 (s, 2H), 5.09 (t, J=5.4 Hz, 1H), 4.49 (dd, J=14.2, 5.3 Hz, 2H), 4.20 (s, 2H), 3.85 (s, 3H), 3.20-3.03 (m, 4H), 1.96 (s, 3H), 1.86 (s, 3H), 1.73 (s, 3H).

Example 3

(3'-(((5-(aminomethyl)-6-methoxypyridin-2-yl)oxo)methyl)-2,2'-dimethyl-[1,1'-biphenyl]-3-yl)methanol

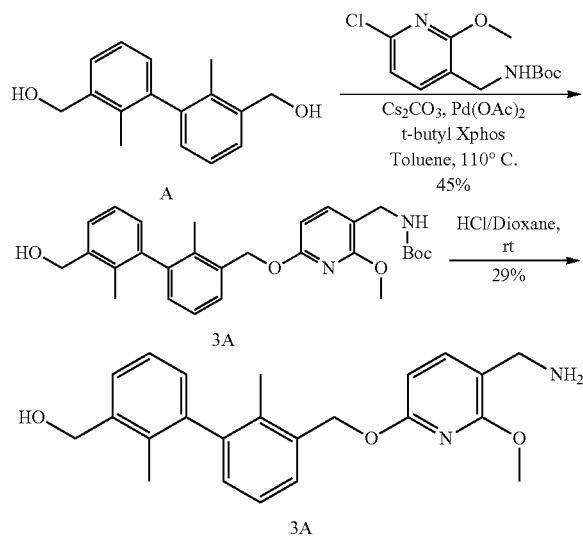

Tert-butyl((6-((3'-(hydroxymethyl)-2,2'-dimethyl-[1,1'-biphenyl]-3-yl)methoxy)-2-methoxypyridin-3-yl)methyl)carbamate

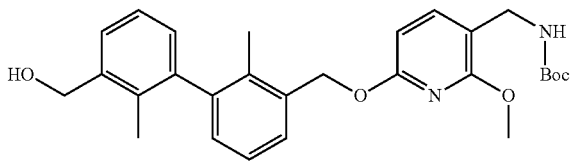 [SMILES: COc1nc(OCc2cccc(-c3cccc(CO)c3C)c2C)ccc1CNC(=O)OC(C)(C)C]

To intermediate A (500.0 mg, 2.0 mmol), tert-butyl ((6-chloro-2-methoxypyridin-3-yl)methyl)carbamate (560.0 mg, 2.0 mmol), cesium carbonate (1340.0 mg, 4.1 mmol) in toluene (5 mL), palladium acetate (46.0 mg, 0.2 mmol) and 2-di-tert-butylphosphino-2',4',6'-triisopropylbiphenyl (175.0 mg, 0.41 mmol) were added. The mixture was exchanged with nitrogen for 3 minutes, and reacted at 110° C. under nitrogen in sealed vessel overnight. The reaction mixture was filtered through celite, the filtrate was concentrated, and the residue was separated and purified with combiflash column chromatography (eluted with petroleum ether/ethyl acetate=5/1) to obtain the target compound 3A (450.0 mg, 45%) as a yellow oil.

MS (ESI): m/z=479.3 [M+H]$^+$.

(3'-(((5-(aminomethyl)-6-methoxypyridin-2-yl)oxo)methyl)-2,2'-dimethyl-[1,1'-biphenyl]-3-yl)methanol (Compound 3)

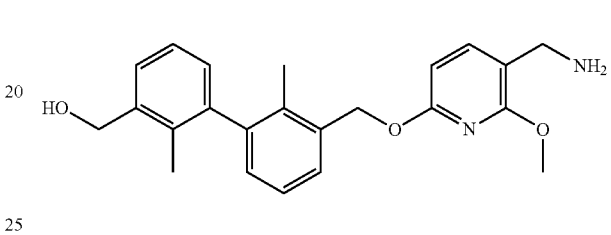

Under 0° C., 1,4-dioxane hydrochloride solution (4 M, 3 mL) was added to compound 3A (65.0 mg, 0.13 mmol), the mixture was stirred at room temperature for 2 hours. The reaction mixture was concentrated, and the residue was separated and purified with combiflash column chromatography (methanol/water) to obtain the target compound example 3 (15.0 mg, 29%) as a transparent gum.

MS (ESI): m/z=362.1 [M-16]$^+$.

$^1$H NMR (400 MHz, DMSO-d$_6$) δ 8.15 (s, 2H), 7.72 (d, J=8.0 Hz, 1H), 7.38 (dd, J=10.4, 7.8 Hz, 2H), 7.20 (dd, J=7.8, 7.3 Hz, 2H), 7.00 (d, J=6.8 Hz, 1H), 6.92 (d, J=6.9 Hz, 1H), 6.48 (d, J=8.0 Hz, 1H), 5.41 (s, 2H), 5.13 (t, J=5.2 Hz, 1H), 4.51 (d, J=4.5 Hz, 2H), 3.89 (s, 3H), 3.85 (s, 2H), 1.96 (s, 3H), 1.86 (s, 3H).

Example 4

N,N-(((((((2,2'-dimethyl-[1,1'-biphenyl]-3,3'-diyl)bis(methylene))bis(oxo))bis(2-methoxypyridine-6,3-diyl))bis(methylene))bis(azetanediyl))bis(ethane-2,1-diyl))diethylamide

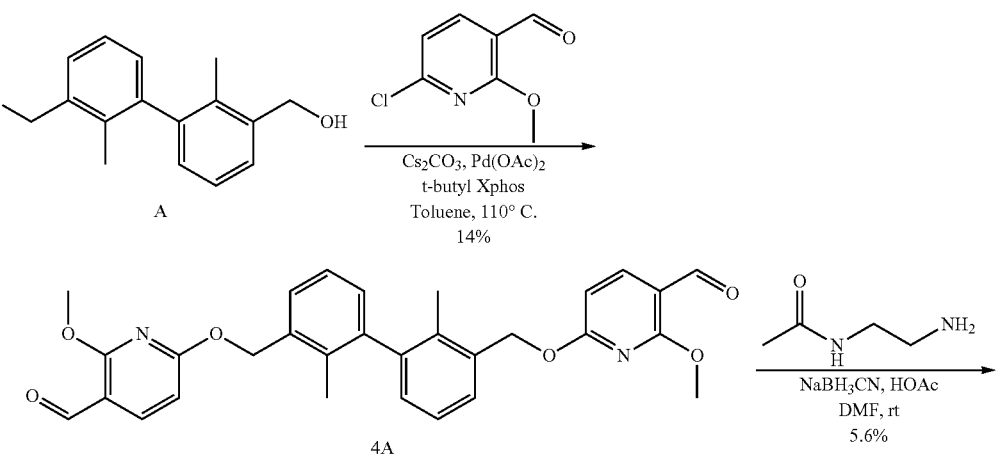

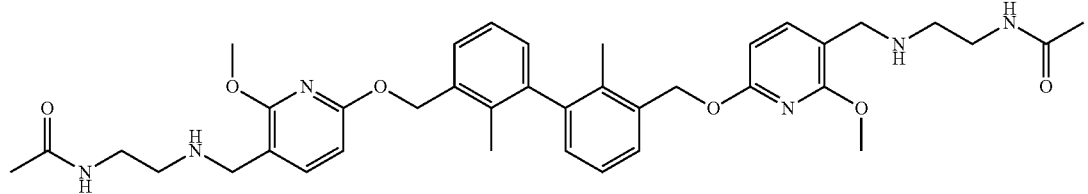

4

6,6'-(((2,2'-dimethyl-[1,1'-biphenyl]-3,3'-diyl)bis(methylene))bis(oxo))bis(2-methoxy nicotyraldehyde)

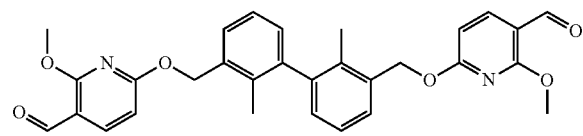 [SMILES: COc1nc(OCc2cccc(-c3cccc(COc4ccc(C=O)c(OC)n4)c3C)c2C)ccc1C=O]

Palladium acetate (25 mg, 0.11 mmol) and 2-di-tert-butylphosphino-2',4',6'-triisopropylbiphenyl (93.0 mg, 0.22 mmol) were added to a mixture of intermediate A (133.0 mg, 0.55 mmol), 6-chloro-2-methoxynicotyraldehyde (188.0 mg, 1.1 mmol) and cesium carbonate (716.0 mg, 2.2 mmol) in toluene (3 mL), the mixture was exchanged with nitrogen for 3 minutes, and reacted at 110° C. under nitrogen in sealed vessel overnight. The reaction mixture was filtered through celite, the filtrate was concentrated, and the residue was separated and purified with combiflash column chromatography (eluted with petroleum ether/ethyl acetate=8/1) to obtain the target compound 4A (40.0 mg, 14%) as a white solid.

MS (ESI): m/z=513.0 [M+H]$^+$.

N,N-(((((((2,2'-dimethyl-[1,1'-biphenyl)-3,3'-diyl) bis(methylene)) bis (oxo)) bis (2-methoxypyridine-6,3-diyl)) bis (methylene)) bis (azetanediyl)) bis (ethane-2,1-diyl)) diethylamide (Compound 4)

Acetic acid (2 drops) was added to a mixture of 4A (40.0 mg, 0.078 mmol) and N-(2-aminoethyl) acetamide (24.0 mg, 0.23 mmol) in N, N-dimethylformamide (2 mL). The mixture was stirred at room temperature for 1 hour, sodium cyanoborohydride (19.0 mg, 0.31 mmol) was added and the mixture was stirred at room temperature overnight. The reaction mixture was separated and purified with combiflash column chromatography (acetonitrile/ammonium bicarbonate aqueous solution (10 mmol/L)) to obtain the target compound example 4 (3 mg, 5.6%) as a transparent gum.

MS (ESI): m/z=343.2 [M/2+H]$^+$.

$^1$H NMR (400 MHz, DMSO-d$_6$) δ 7.75 (s, 2H), 7.58 (d, J=7.9 Hz, 2H), 7.41 (d, J=7.3 Hz, 2H), 7.22 (t, J=7.5 Hz, 2H), 7.02 (d, J=7.6 Hz, 2H), 6.39 (d, J=7.9 Hz, 2H), 5.36 (s, 4H), 3.83 (s, 6H), 3.51 (s, 4H), 3.34 (s, 4H), 3.07 (dd, J=12.5, 6.4 Hz, 4H), 1.97 (s, 6H), 1.74 (s, 6H).

Example 5

6,6'-(((2,2'-dimethyl-[1,1'-biphenyl]-3,3'-diyl) bis(methylene)) bis (oxo)) di(2-methoxynicotyronitrile) (Compound 5)

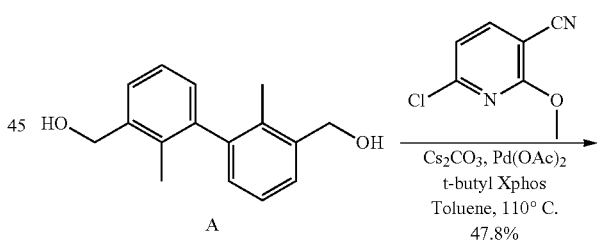

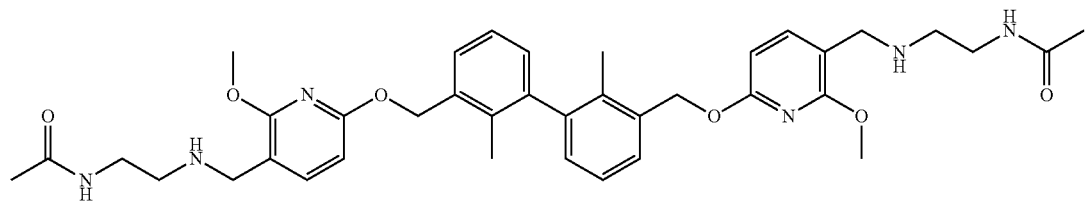 [SMILES: COc1nc(OCc2cccc(-c3cccc(COc4ccc(CNCCNC(C)=O)c(OC)n4)c3C)c2C)ccc1CNCCNC(C)=O]

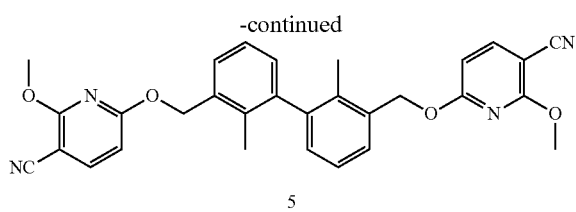

Palladium acetate (55 mg, 0.248 mmol) and 2-di-tert-butylphosphino-2',4',6'-triisopropylbiphenyl (210.0 mg, 0.496 mmol) were added to a mixture of intermediate A (300.0 mg, 1.24 mmol), 6-chloro-2-methoxynicotyronitrile (416 mg, 2.48 mmol) and cesium carbonate (1616.0 mg, 4.96 mmol) in toluene (5 mL). The mixture was exchanged with nitrogen for 3 minutes, and reacted at 110° C. under nitrogen in sealed vessel overnight. The reaction mixture was filtered through celite, the filtrate was concentrated, and the residue was separated and purified with combiflash column chromatography (eluted with petroleum ether/ethyl acetate=4/1) to obtain the target compound example 5 (300.0 mg, 47.8%) as a white solid.

MS (ESI): m/z=507.2 [M+H]$^+$.

$^1$H NMR (400 MHz, DMSO-$d_6$) δ 8.07 (d, J=8.4 Hz, 2H), 7.43 (d, J=7.5 Hz, 2H), 7.24 (t, J=7.6 Hz, 2H), 7.06 (d, J=7.3 Hz, 2H), 6.60 (d, J=8.3 Hz, 2H), 5.49 (s, 4H), 3.98 (s, 6H), 1.97 (s, 6H).

Example 6

(((((2,2'-dimethyl-[1,1'-biphenyl]-3,3'-diyl) bis (methylene)) bis (oxo)) bis (2-methoxypyridine-6,3-diyl)) dimethylamine (Compound 6)

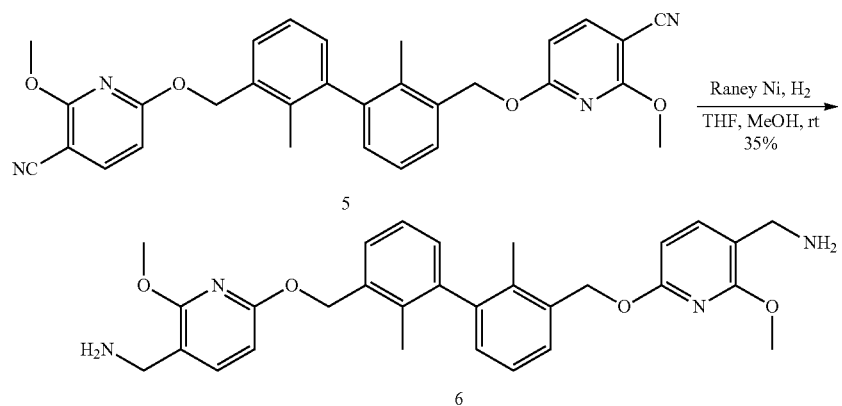

Raney nickel (45.0 mg, 50%) was added to a mixture of compound example 5 (90.0 mg, 0.17 mmol) and aqueous ammonia (0.5 mL) in tetrahydrofuran (1 mL) and methanol (3 mL), and the mixture was stirred at room temperature under hydrogen overnight. The reaction mixture was filtered through celite, and the filtrate was concentrated. The residue was separated and purified with combiflash column chromatography (acetonitrileaqueous ammonium bicarbonate solution (10 mmol/L)) to obtain the target compound example 6 (32.0 mg, 35%) as a transparent gum.

MS (ESI): m/z=241.1 [(M-32)/2]$^+$.

$^1$H NMR (400 MHz, DMSO-$d_6$) δ 7.60 (d, J=7.9 Hz, 2H), 7.40 (d, J=7.5 Hz, 2H), 7.21 (t, J=7.5 Hz, 2H), 7.02 (d, J=7.5 Hz, 2H), 6.38 (d, J=7.9 Hz, 2H), 5.36 (s, 4H), 3.83 (s, 6H), 3.53 (s, 4H), 1.97 (s, 6H).

Example 7

(3'-(((6-(aminomethyl)pyridin-2-yl)oxo)methyl)-2,2'-dimethyl-[1,1'-biphenyl]-3-yl)methanol

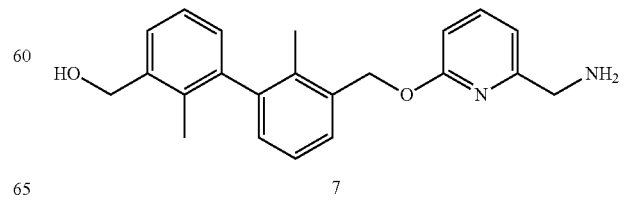

6-((3'-(hydroxymethyl)-2,2'-dimethyl-[1,1'-biphenyl]-3-yl)methoxy)cyanopyridine

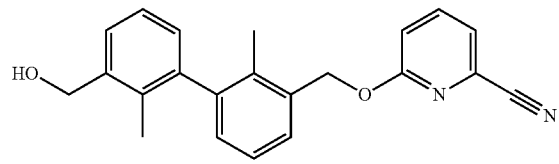 [SMILES: Cc1c(CO)cccc1-c1cccc(COc2cccc(C#N)n2)c1C]

The intermediate A (400.0 mg, 1.65 mmol), 6-chlorocyanopyridine (150.0 mg, 1.08 mmol), palladium acetate (22.4 mg, 0.1 mmol), 2-di-tert-butylphosphino-2',4',6'-triisopropylbiphenyl (120.0 mg, 0.28 mmol) and cesium carbonate (700.0 mg, 2.13 mmol) were added into anhydrous toluene. The mixture was replaced with nitrogen for three times, heated to reflux overnight, cooled, filtered, and concentrated, then the residue was separated and purified with combiflash column chromatography (eluted with petroleum ether/ethyl acetate=1/5) to provide the target compound 7A (58.0 mg, 15%).
MS (ESI): m/z=367.1[M-23]$^+$.

(3'-(((6-(aminomethyl)pyridin-2-yl)oxo)methyl)-2,2'-dimethyl-[1,1'-biphenyl]-3-yl)methanol (Compound 7)

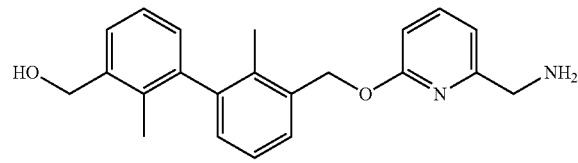 [SMILES: Cc1c(CO)cccc1-c1cccc(COc2cccc(CN)n2)c1C]

Compound 7A (58.0 mg, 0.17 mmol) was dissolved in methanol (5 mL), raney Ni and a drop of saturated ammonia water were added, the mixture was replaced with hydrogen for three times and stirred overnight under hydrogen atmosphere. The mixture was filtered and concentrated, and the residue was separated and purified with combiflash column chromatography (methanol/water) to obtain the target compound Example 7 (16 mg, 27%).
MS (ESI): m/z=349.1 [M+H]$^+$.
$^1$H NMR (400 MHz, CD$_3$OD) δ 7.66 (dd, J=8.1, 7.4 Hz, 1H), 7.46 (d, J=7.4 Hz, 1H), 7.40 (d, J=7.4 Hz, 1H), 7.24 (t, J=7.6 Hz, 2H), 7.05 (d, J=8.2 Hz, 1H), 7.03 (d, J=7.8 Hz, 1H), 6.94 (d, J=7.2 Hz, 1H), 6.74 (d, J=8.2 Hz, 1H), 5.47 (s, 2H), 4.71 (s, 2H), 3.83 (s, 2H), 2.08 (s, 3H), 2.03 (s, 3H).

Example 8

(3'-(((6-(aminomethyl)pyridin-2-yl)oxo)methyl)-2,2'-dimethyl-[1,1'-biphenyl]-3-yl)methanol

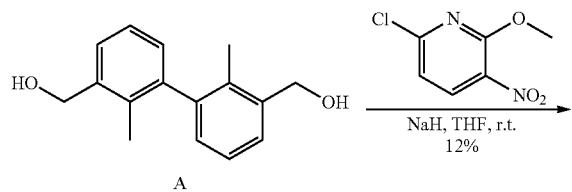

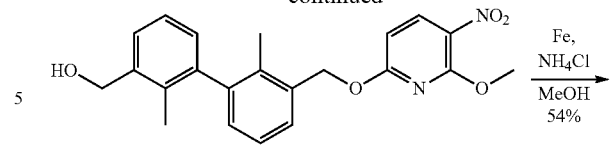

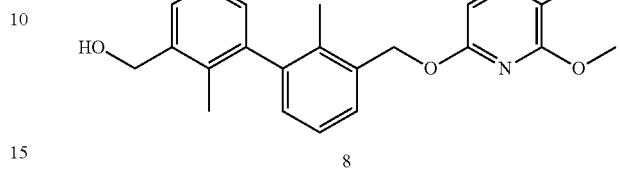

(3'-(((6-methoxy-5-nitropyridin-2-yl)oxo)methyl)-2,2'-dimethyl-[1,1'-biphenyl]-3-yl)methanol

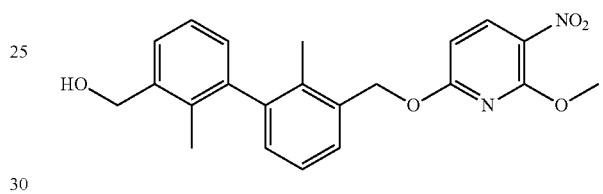

Intermediate A (290.0 mg, 1.2 mmol) was dissolved in tetrahydrofuran (20 mL), and sodium hydride (60.0 mg, 1.5 mmol) was added under ice bath. after the mixture was stirred for half an hour, 6-chloro-2-methoxy-3-nitropyridine (188.0 mg, 1.0 mmol) was added and the mixture was stirred at room temperature overnight. The reaction was quenched by adding water and extracted with ethyl acetate. The organic phase was washed with brine, dried over anhydrous sodium sulfate, filtered and concentrated. The residue was separated and purified with combiflash column chromatography (eluted with petroleum ether/ethyl acetate=1/5) to give the target compound 8A (50.0 mg, 12%).
MS (ESI): m/z=377.1 [M-OH]$^+$.

(3'-(((6-(aminomethyl)pyridin-2-yl)oxo)methyl)-2,2'-dimethyl-[1,1'-biphenyl]-3-yl)methanol (Compound 8)

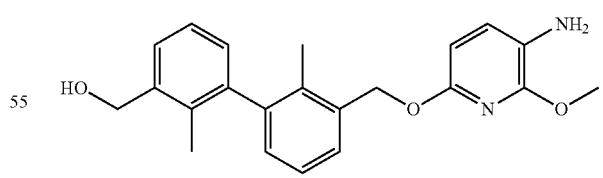

Compound 8A (50.0 mg, 0.12 mmol) was dissolved in methanol (8 mL), iron powder (30.0 mg, 0.6 mmol) and statured ammonium chloride solution (1 mL) were added, and the mixture was stirred at reflux overnight under nitrogen protection. The mixture was filtered and concentrated, and the residue was separated and purified by Prep-HPLC to obtain the target compound Example 8 (25.0 mg, 54%).
MS (ESI): m/z=365.1[M+H]$^+$.

¹H NMR (400 MHz, CD₃OD) δ 7.41 (d, J=8.6 Hz, 2H), 7.23 (d, J=7.8 Hz, 2H), 7.09 (d, J=8.2 Hz, 1H), 7.03 (dd, J=6.7, 4.9 Hz, 2H), 6.27 (d, J=8.1 Hz, 1H), 5.35 (s, 2H), 4.70 (s, 2H), 3.97 (s, 3H), 2.06 (s, 3H), 2.03 (s, 3H).

Example 9

1,1'-(((((2,2'-dimethyl-[1,1'-biphenyl]-3,3'-diyl) bis (methylene)) bis (oxo))bis (2-methoxypyridine-6,3-diyl)) bis (methylene)) bis (piperidine-2-carboxylic acid) (Compound 9)

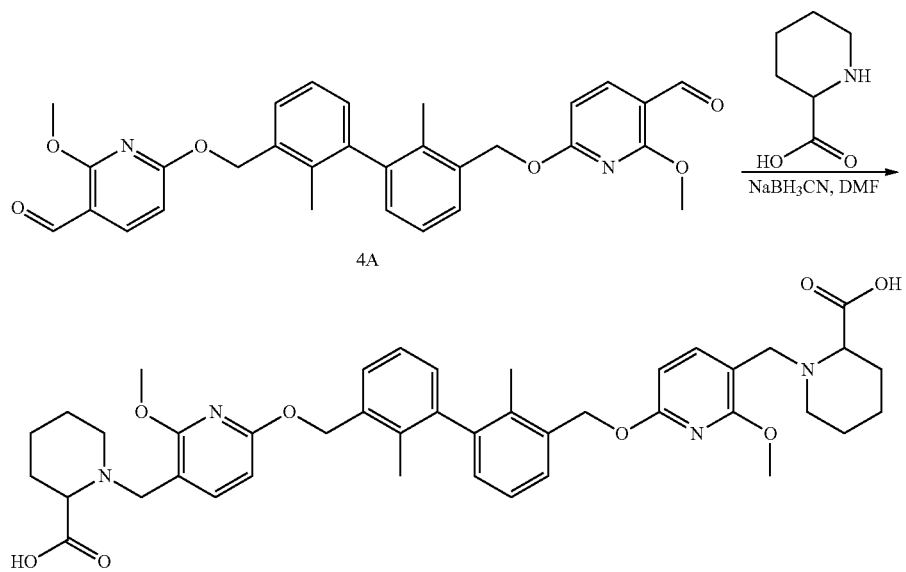

Intermediate 4A (60.0 mg, 0.12 mmol) was dissolved in N,N-dimethylformamide (3 mL), and piperidine-2-carboxylic acid (75.0 mg, 0.5 mmol) was added and stirred at 80° C. under nitrogen protection for 2 hours. After cooled, sodium cyanoborohydride (32.0 mg, 0.5 mmol) was added to the system, stirred at room temperature overnight, and concentrated. The residue was purified by Prep-HPLC to obtain the target compound example 9 (5.0 mg, 6%).

MS (ESI): m/z=739.3[M+H]⁺.

¹H NMR (400 MHz, CD₃OD) δ 8.18 (s, 2H), 7.79 (d, J=8.1 Hz, 2H), 7.46 (d, J=7.4 Hz, 2H), 7.25 (t, J=7.6 Hz, 2H), 7.12-7.01 (m, 2H), 6.52 (d, J=8.1 Hz, 2H), 5.52 (s, 4H), 4.34 (m, 4H), 4.03 (s, 6H), 3.46 (m, 4H), 2.97 (t, J=11.8 Hz, 2H), 2.25 (m, 2H), 2.07 (s, 6H), 1.92-1.46 (m, 10H).

Example 10

N-(2-((4-((3'-(hydroxymethyl)-2,2'-dimethyl-[1,1'-biphenyl]-3-yl)methoxy)-2,6-dimethoxybenzyl) amino)ethyl) acetamide

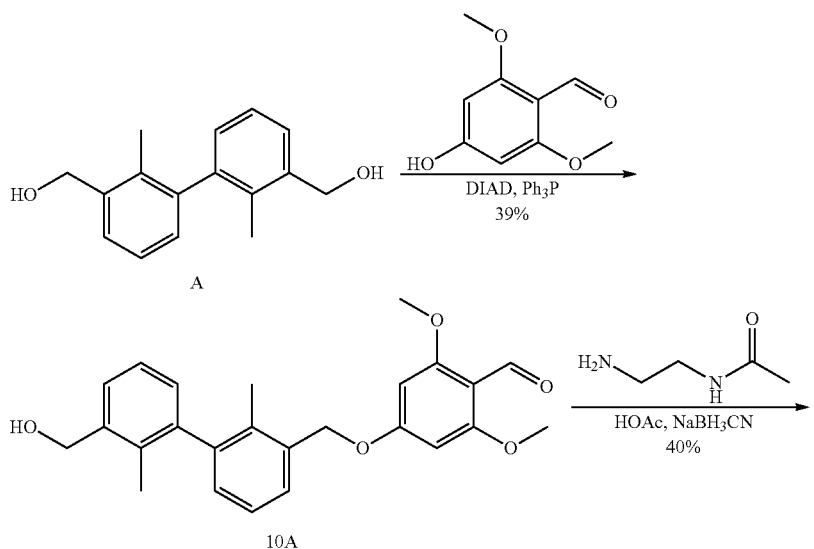

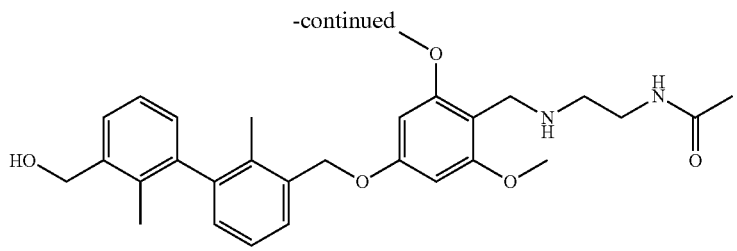

10

4-((3'-(hydroxymethyl)-2,2'-dimethyl-[1,1'-biphenyl]-3-yl) methoxy)-2,6-dimethoxy benzaldehyde

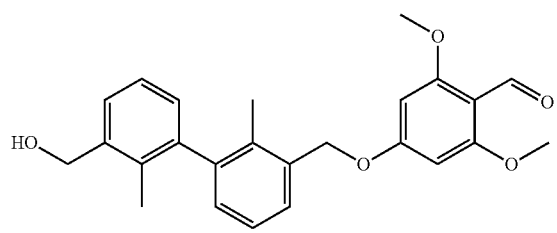 [SMILES: COc1cc(OCc2cccc(-c3cccc(CO)c3C)c2C)cc(OC)c1C=O]

Intermediate A (200.0 mg, 0.83 mmol), 4-hydroxy-2,6-dimethoxybenzaldehyde (331.0 mg, 1.8 mmol), and triphenylphosphine (551.0 mg, 2.1 mmol) in tetrahydrofuran (4 mL) was cooled to 0° C. A solution of diisopropyl azodicarboxylate (420.0 mg, 2.1 mmol) in tetrahydrofuran (2 mL) was added to the reaction mixture. The reaction mixture was stirred overnight at room temperature and then concentrated. The residue was purified by silica gel column chromatography (petroleum ether/ethyl acetate=9/1-3/7) to provide a mixture, then the mixture was further separated and purified with combiflash column chromatography (eluted with ~0.01% of trifluoroacetic acid aqueous solution/acetonitrile=90/10-50/50) to obtain the target compound 10A (138.0 mg, 39%) as a white solid.

MS (ESI): m/z=407 [M+H]$^+$.

N-(2-((4-((3'-(hydroxymethyl)-2,2'-dimethyl-[1,1'-biphenyl]-3-yl) methoxy)-2,6-Dimethoxybenzyl) amino) ethyl) acetamide (Compound 10)

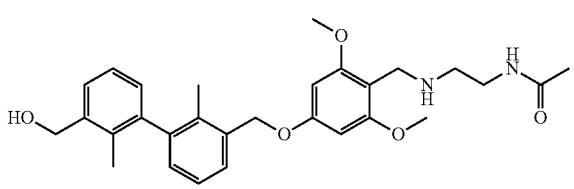 [SMILES: COc1cc(OCc2cccc(-c3cccc(CO)c3C)c2C)cc(OC)c1CNCCNC(C)=O]

A mixed solution of compound 10A (50.0 mg, 0.12 mmol), N-(2-aminoethyl) acetamide (18.0 mg, 0.18 mmol) and acetic acid (4 mg, 0.06 mmol) in N, N-dimethylformamide (0.2 mL) and methanol (0.2 mL) was stirred at room temperature for 1 hour. Then sodium cyanoborohydride (30.0 mg, 0.48 mmol) was added to the reaction mixture, and the reaction mixture was stirred at room temperature for 2 hours. The reaction mixture was directly separated and purified with combiflash column chromatography (eluted with ~0.1% formic acid aqueous solution/acetonitrile=95/5-70/30) to obtain the target compound example 10 (24.0 mg, 40%) as a white solid.

MS (ESI): m/z=493 [M+H]$^+$.

$^1$H NMR (400 MHz, CD3OD) δ 8.52 (s, 1H), 7.47-7.34 (m, 2H), 7.25-7.18 (m, 2H), 7.07-6.95 (m, 2H), 6.37 (s, 2H), 5.17 (s, 2H), 4.67 (s, 2H), 4.09 (s, 2H), 3.85 (s, 6H), 3.41 (t, J=5.9 Hz, 2H), 2.97 (t, J=6.0 Hz, 2H), 2.03 (s, 3H), 1.99 (s, 3H), 1.94 (s, 3H).

Example 11

(3'-((4-(aminomethyl)-3,5-dimethoxyphenoxy) methyl)-2,2'-dimethyl-[1,1'-biphenyl]-3-yl)methanol (Compound 11)

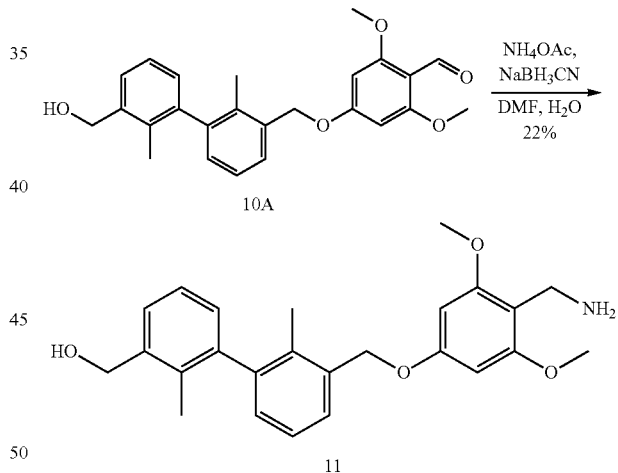

A mixture of compound 10A (50.0 mg, 0.12 mmol) and ammonium acetate (46.0 mg, 0.60 mmol) in N, N'-dimethylformamide (0.2 mL) and methanol (0.2 mL) was stirred at room temperature for 1 hour, and sodium cyanoborohydride (30.0 mg, 0.48 mmol) was added to the reaction mixture and the reaction mixture was stirred overnight at room temperature. The reaction mixture was directly separated and purified with combiflash column chromatography (eluted with ~0.1% formic acid aqueous solution/acetonitrile=95/5-70/30) to obtain the target compound example 11 (12.0 mg, 22%) as a white solid.

MS (ESI): m/z=391 [M+H-NH3]$^+$.

$^1$H NMR (400 MHz, CD$_3$OD): δ 8.40 (s, 1H), 7.43 (d, J=6.9 Hz, 1H), 7.37 (d, J=7.4 Hz, 1H), 7.27-7.14 (m, 2H), 7.02 (d, J=6.7 Hz, 1H), 6.93 (d, J=6.8 Hz, 1H), 6.36 (s, 2H), 5.20-5.08 (m, 2H), 4.59-4.41 (m, 2H), 3.76 (s, 6H), 1.96 (s, 3H), 1.87 (s, 3H).

Example 12

(3'-(((4-amino-6-methoxypyridin-2-yl)oxo)methyl)-2,2'-dimethyl-[1,1'-biphenyl]-3-yl)methanol (Compound 12)

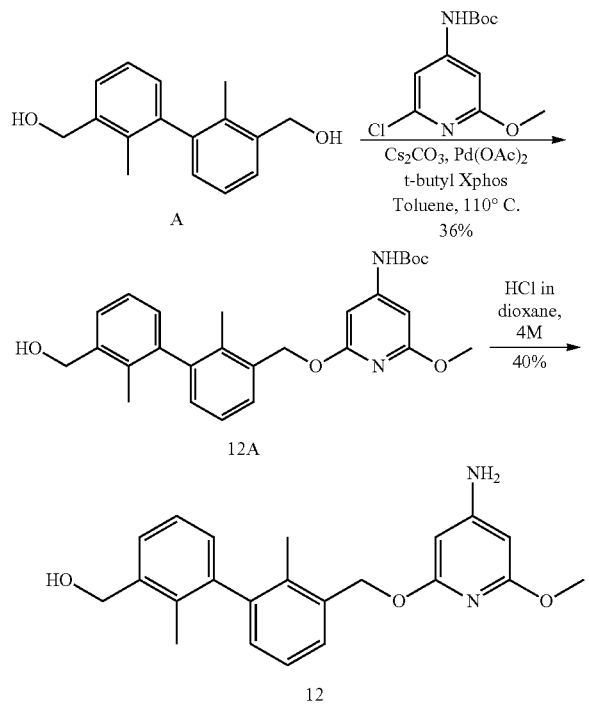

Tert-butyl (2-((3'-(hydroxymethyl)-2,2'-dimethyl-[1,1'-biphenyl]-3-yl) methoxy)-6-methoxypyridin-4-yl) carbamate

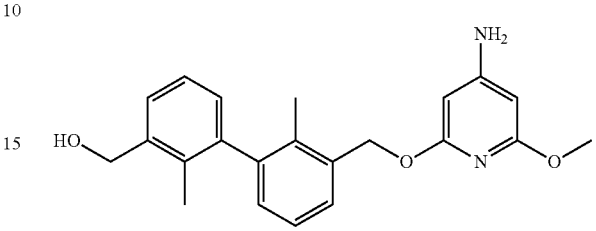

Palladium acetate (13.0 mg, 0.06 mmol) and 2-di-tert-butylphosphino-2',4',6'-triisopropylbiphenyl (51 mg, 0.12 mmol) were added to a mixture of intermediate A (150.0 mg, 0.60 mmol), tert-butyl ((2-chloro-6-methoxypyridin-4-yl) carbamate (156.0 mg, 0.60 mmol), cesium carbonate (390.0 mg, 1.2 mmol) in toluene (3 mL), the mixture was exchanged with nitrogen for 3 minutes, and was allowed to react at 100° C. under nitrogen in sealed vessel overnight. The reaction mixture was concentrated, and residue was separated and purified with combiflash column chromatography (eluted with ~0.05% trifluoroacetic acid aqueous solution/acetonitrile=99/1-30/70) to obtain the target compound 12A (100.0 mg, 36%) as a white solid.

MS (ESI): m/z=465 [M+H]⁺.

(3'4-(4-amino-6-methoxypyridin-2-yl) oxo) methyl)-2,2'-dimethyl-[1,1'-biphenyl]-3-yl) methanol Compound 12A (50.0 mg, 0.11 mmol) was dissolved in dioxane hydrochloride solution (4 M, 2 mL), and the reaction mixture was stirred for 2 hours. The reaction mixture was concentrated, and residue was separated and purified with combiflash column chromatography (eluted with ~0.1% formic acid aqueous solution/acetonitrile=99/1-30/70) to obtain the target compound example 12 (16.0 mg, 40%) as a white solid.

MS (ESI): m/z=365 [M+H]⁺.

$^1$H NMR (400 MHz, DMSO-$d_6$) δ 7.36 (dd, J=7.0, 3.5 Hz, 2H), 7.19 (t, J=7.5 Hz, 2H), 6.97 (d, J=6.9 Hz, 1H), 6.93 (d, J=6.9 Hz, 1H), 5.84 (s, 2H), 5.56 (d, J=1.4 Hz, 1H), 5.50 (d, J=1.4 Hz, 1H), 5.09 (s, 1H), 4.51 (s, 2H), 3.67 (s, 3H), 1.94 (s, 3H), 1.87 (s, 3H).

Example 13

(3'(((6-aminopyridin-2-yl) oxo) methyl)-2,2'-dimethyl-[1,1'-biphenyl]-3-yl) methanol

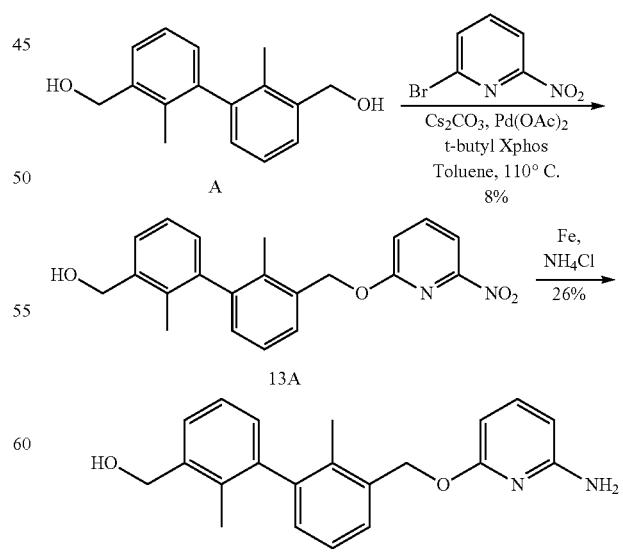

(2,2'-dimethyl-3'(((6-nitropyridin-2-yl) oxo) methyl)-[1,1'-biphenyl]-3-yl) methanol

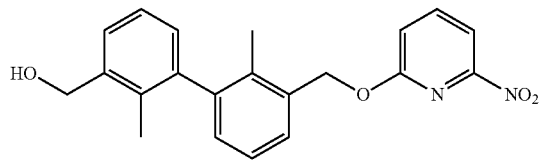 [SMILES: Cc1c(CO)cccc1-c1cccc(COc2cccc([N+](=O)[O-])n2)c1C]

Palladium acetate (37.0 mg, 0.165 mmol) and 2-di-tert-butylphosphino-2',4',6'-triisopropylbiphenyl (140.0 mg, 0.33 mmol) were added to a solution of intermediate A (400.0 mg, 1.65 mmol), 2-bromo-6-nitropyridine (335.0 mg, 1.65 mmol), cesium carbonate (1.08 g, 3.30 mmol) in toluene (3 mL), the mixture was exchanged with nitrogen for 3 minutes, and reacted at 100° C. under nitrogen in sealed vessel overnight. The reaction mixture was concentrated, and residue was purified with combiflash column chromatography (eluted with ~0.05% trifluoroacetic acid aqueous solution/acetonitrile=99/1-30/70) to obtain the target compound 13A (50.0 mg, 8%) as a pale yellow solid.

MS (ESI): m/z=365 [M+H]$^+$.

(3'(((6-aminopyridin-2-yl) oxo) methyl)-2,2'-dimethyl-[1,1'-biphenyl]-3-yl) methanol (Compound 13)

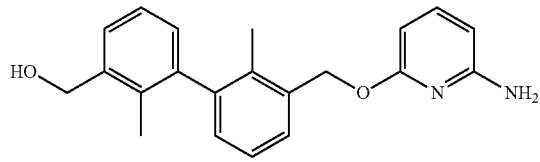

A mixture of compound 13A (50.0 mg, 0.14 mmol), iron powder (50.0 mg, 0.90 mmol) and statured ammonium chloride (50.0 mg, 0.94 mmol) in ethanol (4 mL) and water (1 mL) was heated to 80° C. and stirred for 3 hours. The reaction mixture was diluted with ethyl acetate and methanol and then filtered. The filtrate was concentrated, and residue was separated and purified with combiflash column chromatography (eluted with ~0.1% formic acid aqueous solution/acetonitrile=99/1-30/70) to obtain the target compound example 13 (12.0 mg, 26%) as a white solid.

MS (ESI): m/z=335 [M+H]$^+$.

$^1$H NMR (400 MHz, DMSO-d$_6$) δ 7.41-7.34 (m, 2H), 7.26 (t, J=7.8 Hz, 1H), 7.19 (m, 2H), 6.98 (d, J=7.5 Hz, 1H), 6.93 (d, J=7.4 Hz, 1H), 5.98 (d, J=7.8 Hz, 1H), 5.91 (d, J=7.8 Hz, 1H), 5.83 (s, 2H), 5.23 (s, 2H), 4.51 (s, 2H), 1.93 (s, 3H), 1.88 (s, 3H).

Example 14

N, N'-(((((((2,2'-dimethyl-[1,1'-biphenyl]-3,3'-diyl) bis(methylene))bis(oxo))bis (2,6-dimethoxy-4,1-phenylene)) bis (methylene)) bis (azetanediyl)) bis (ethane-2,1-diyl) diacetamide

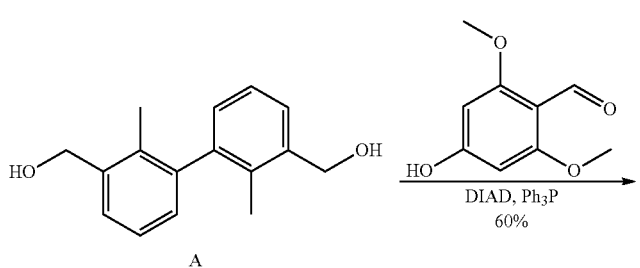

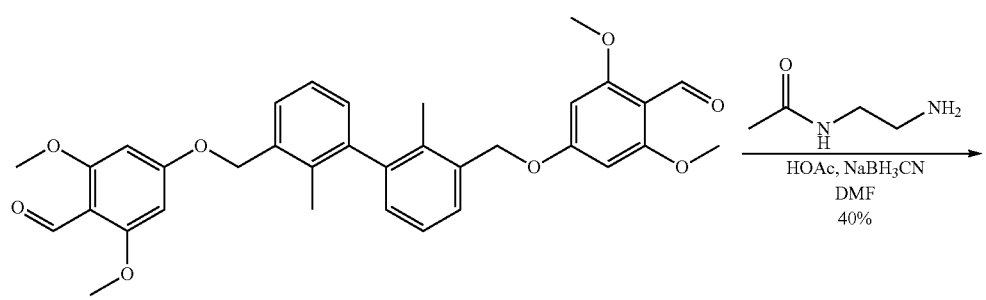

14A

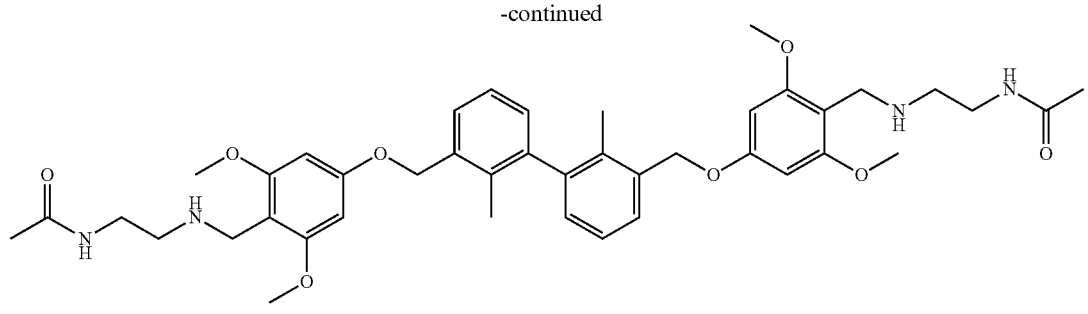

14

4,4'-(((2,2'-dimethyl-[1,1'-biphenyl]-3,3'-diyl) bis (methylene)) bis (oxo)) di (2,6-dimethoxybenzaldehyde)

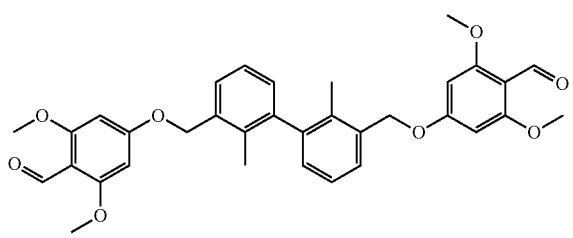 [SMILES: COc1cc(OCc2cccc(-c3cccc(COc4cc(OC)c(C=O)c(OC)c4)c3C)c2C)cc(OC)c1C=O]

The mixture of intermediate A (500.0 mg, 2.1 mmol), 4-hydroxy-2,6-dimethoxybenzaldehyde (950.0 mg, 5.2 mmol) and triphenylphosphine (1.4 g, 5.2 mmol) in tetrahydrofuran (10 mL) was cooled to 0° C. A solution of diisopropyl azodicarboxylate (1.1 g, 5.2 mmol) in tetrahydrofuran (4 mL) was added to the reaction mixture. The reaction mixture was stirred at room temperature for 24 hours, concentrated. The residue was separated and purified with combiflash column chromatography (eluted with petroleum ether/ethyl acetate=4/1-1/4) to obtain the target compound 14A (710.0 mg, 60%) as a white solid.

MS (ESI): m/z=571 [M+H]$^+$.

N, N-(((((((2,2'-dimethyl-[1,1'-biphenyl]-3,3'-diyl) bis(methylene))bis(oxo))bis (2,6-dimethoxy-4,1-phenylene)) bis (methylene)) bis (azetanediyl)) bis (ethane-2,1-diyl) diacetamide (Compound 14)

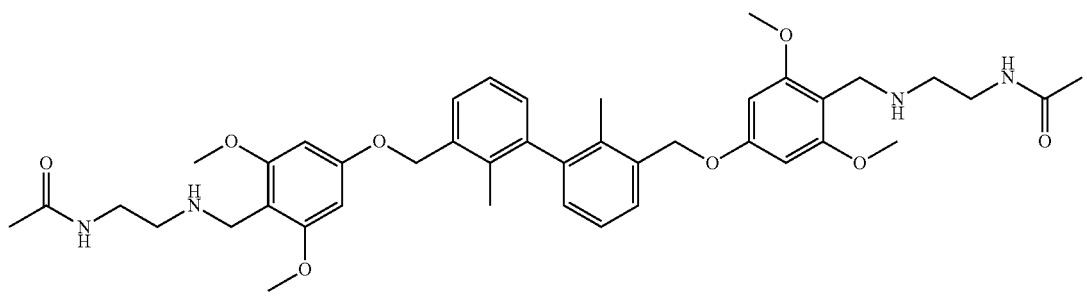 [SMILES: COc1cc(OCc2cccc(-c3cccc(COc4cc(OC)c(CNCCNC(C)=O)c(OC)c4)c3C)c2C)cc(OC)c1CNCCNC(C)=O]

A mixture of compound 14A (50.0 mg, 0.087 mmol), N-(2-aminoethyl) acetamide (27.0 mg, 0.26 mmol) and acetic acid (1 drop) in N, N-dimethylformamide (1 mL) was stirred at room temperature for 1 hour. Cyanoborohydride (22.0 mg, 0.35 mmol) was added to the reaction mixture and stirred at room temperature for 2 hours. The reaction mixture was directly separated and purified with combiflash column chromatography (eluted with 10 mM NH$_4$HCO$_3$ aqueous solution/acetonitrile=99/1-40/60) to obtain the target compound example 14 (24.0 mg, 40%) as a white solid.

MS (ESI): m/z=372 [M/2+H]$^+$.

$^1$H NMR (400 MHz, DMSO-d$_6$) δ 7.73 (s, 2H), 7.46 (d, J=7.7 Hz, 2H), 7.26 (m, 2H), 7.06 (d, J=7.5 Hz, 2H), 6.32 (s, 4H), 5.13 (s, 4H), 3.72 (s, 12H), 3.57 (s, 4H), 3.04 (dd, J=12.2, 6.1 Hz, 4H), 2.42 (t, J=6.4 Hz, 4H), 1.99 (s, 6H), 1.74 (s, 6H).

Example 15

(3'-(((5-(2-aminoethyl)-6-methoxypyridin-2-yl) oxo) methyl)-2,2'-dimethyl-[1,1'-biphenyl]-3-yl) methanol

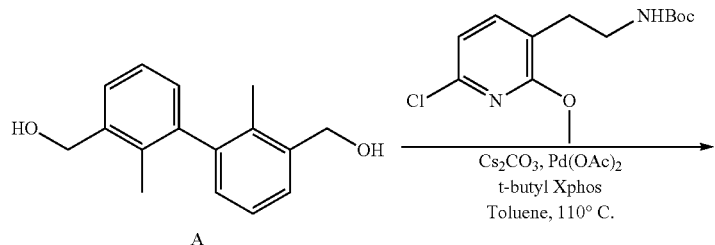

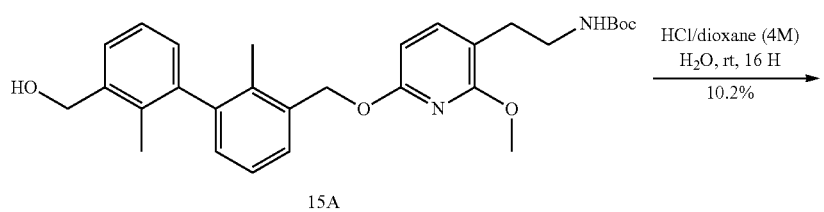

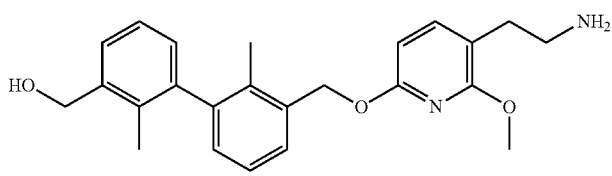

Tert-butyl (2-(6-((3'-(hydroxymethyl)-2,2'-dimethyl-[1,1'-biphenyl]-3-yl) methoxy)-2-methoxypyridin-3-yl) ethyl) carbamate

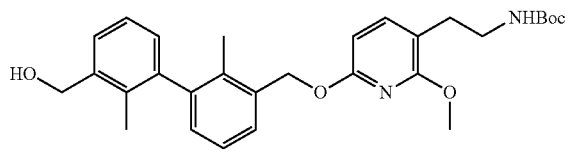 [SMILES: COc1nc(OCc2cccc(-c3cccc(CO)c3C)c2C)ccc1CCNC(=O)OC(C)(C)C]

Palladium acetate (16.0 mg, 0.07 mmol) and 2-di-tert-butylphosphino-2',4',6'-triisopropylbiphenyl (30 mg, 0.07 mmol) were added to a mixture of intermediate A (181.0 mg, 0.75 mmol), tert-butyl (2-(6-chloro(2-methoxypyridin-3-yl) ethyl)carbamate (214.0 mg, 0.75 mmol), cesium carbonate (489.0 mg, 1.50 mmol) in toluene (2 mL), the mixture was exchanged with nitrogen for 3 minutes, and was allowed to heat to 100° C. under nitrogen in sealed vessel overnight. The reaction mixture was concentrated, and the residue was purified with combiflash column chromatography (eluted with petroleum ether/ethyl acetate=5/1) and combiflash column chromatography (eluted with acetonitrile/water) to obtain an aqueous solution (5 mL) of the target compound 15A.

MS (ESI): m/z=493.2 [M+H]$^+$ (3'-(((5-(2-aminoethyl)-6-methoxypyridin-2-yl) oxo) methyl)-2,2'-dimethyl-[1,1'-biphenyl]-3-yl) methanol (Compound 15)

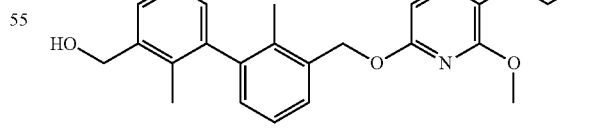

Hydrochloric acid/1,4-dioxane solution (4 M, 4 mL) was added to an aqueous solution (5 mL) of compound 15A, and the reaction was stirred at room temperature for 24 hours. The reaction mixture was concentrated to 4 mL, the residue was purified with combiflash column chromatography (eluted with acetonitrile/water) to obtain the target compound example 15 (30.0 mg, 10.2%) as a white solid.

MS (ESI): m/z=393.2 [M+H]$^+$.

¹H NMR (400 MHz, CDCl₃) δ 8.25 (s, 3H), 7.42-7.33 (m, 3H), 7.20 (m, 2H), 7.05 (m, 2H), 6.29 (d, J=7.9 Hz, 1H), 5.37 (s, 2H), 4.73 (s, 2H), 3.92 (s, 3H), 3.18 (s, 2H), 2.93 (m, 2H), 2.02 (s, 3H), 1.94 (s, 3H).

Example 16

(6-((3'-(aminomethyl)-2'-methyl-[1,1'-biphenyl]-3-yl)methoxy)-2-methoxypyridin-3-yl) methylamine

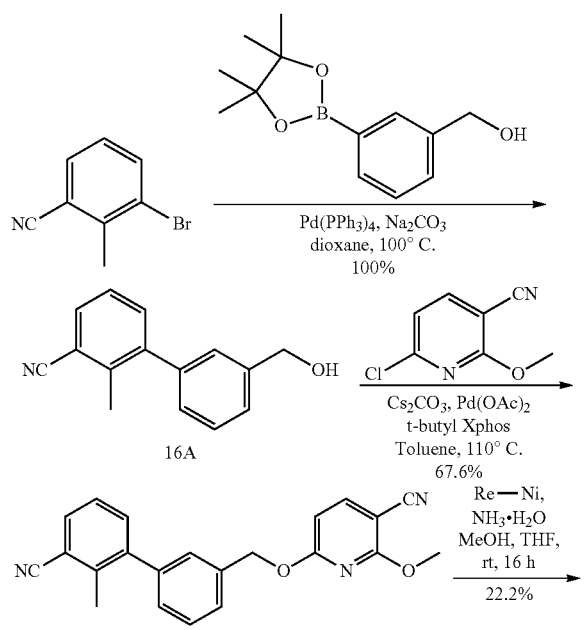

3'-(hydroxymethyl)-2-methyl-[1,1'-biphenyl]-3-carbonitrile

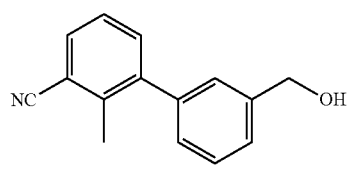 [SMILES: Cc1c(C#N)cccc1-c1cccc(CO)c1]

Tetrakis (triphenylphosphine) palladium (58.0 mg, 0.05 mmol) was added to a mixture of 3-bromo-2-methylbenzonitrile (195.0 mg, 1.0 mmol), 3-hydroxymethylphenylborate (304.0 mg, 1.30 mmol), sodium carbonate (318.0 mg, 3.0 mmol) in 1,4-dioxane (3 mL). The mixture was exchanged with nitrogen for 1 minute, and reacted at 100° C. under argon atmosphere in sealed vessel for two days. The reaction mixture was cooled and concentrated. The crude product was separated and purified by silica gel column chromatography (eluted with petroleum ether/ethyl acetate=1/2) to obtain the target compound 16A (230.0 mg, 100%) as a colorless oil.

MS (ESI): m/z=224.1 [M+H]⁺.

6-((3'-cyano-2'-methyl-[1,1'-biphenyl]-3-yl)methoxy)-2-methoxynicotyronitrile

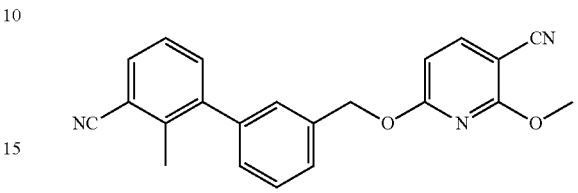

Palladium acetate (44.0 mg, 0.2 mmol) and 2-di-tert-butylphosphino-2',4',6'-triisopropylbiphenyl (45 mg, 0.1 mmol) was added to a mixture of intermediate 16A (223.0 mg, 1.00 mmol), 6-chloro-2-methoxy-3-pyridinecarbonitrile (168.0 mg, 1.00 mmol), cesium carbonate (652.0 mg, 2.00 mmol) in toluene (2 mL). The mixture was exchanged with nitrogen for 3 minutes, and reacted at 100° C. under argon atmosphere in sealed vessel overnight. The reaction mixture was concentrated, and the crude product was separated and purified by silica gel column chromatography (eluted with petroleum ether/ethyl acetate=3/1) to obtain target compound 16B (240.0 mg, 67.6%) as a white solid.

MS (ESI): m/z=356.1 [M+H]⁺.

(6-((3'-(aminomethyl)-2'-methyl-[1,1'-biphenyl]-3-yl)methoxy)-2-methoxypyridin-3-yl) methylamine
(Compound 16)

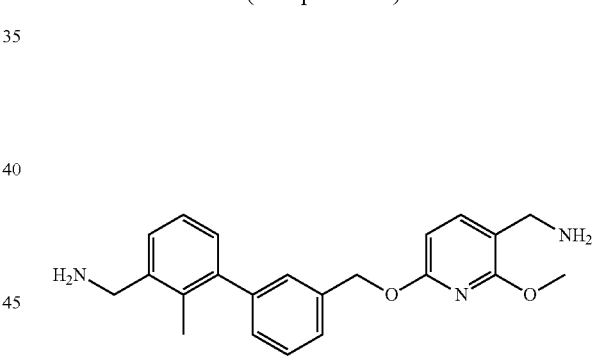

Ammonia (2 mL) and Raney nickel (20.0 mg) was added to a mixture of compound 16B (90.0 mg, 0.25 mmol) in Methanol (10 mL) and tetrahydrofuran (5 mL), and the mixture was reacted at room temperature overnight under hydrogen atmosphere. The reaction mixture was filtered, and the filtrate was concentrated. The crude product was purified by combiflash column chromatography (eluted with acetonitrile/water gradient) to obtain the target compound Example 16 (20.0 mg, 22.2%) as a colorless oil.

MS (ESI): m/z=347.1 [M-16]⁺.

¹H NMR (400 MHz, CDCl₃) δ 7.42-7.37 (m, 3H), 7.36-7.34 (m, 1H), 7.33-7.30 (m, 1H), 7.23-7.19 (m, 2H), 7.14-7.10 (m, 1H), 6.31 (d, J=7.8 Hz, 1H), 5.39 (s, 2H), 3.91 (s, 5H), 3.69 (s, 2H), 2.18 (s, 3H).

Example 17

N-(2-(((6-((3'-(((5-cyano-6-methoxypyridin-2-yl)oxo)methyl)-2,2'-dimethyl-[1,1'-biphenyl]-3-yl)methoxy)-2-methoxypyridin-3-yl)methyl)amino)ethyl) acetamide (Compound 17)

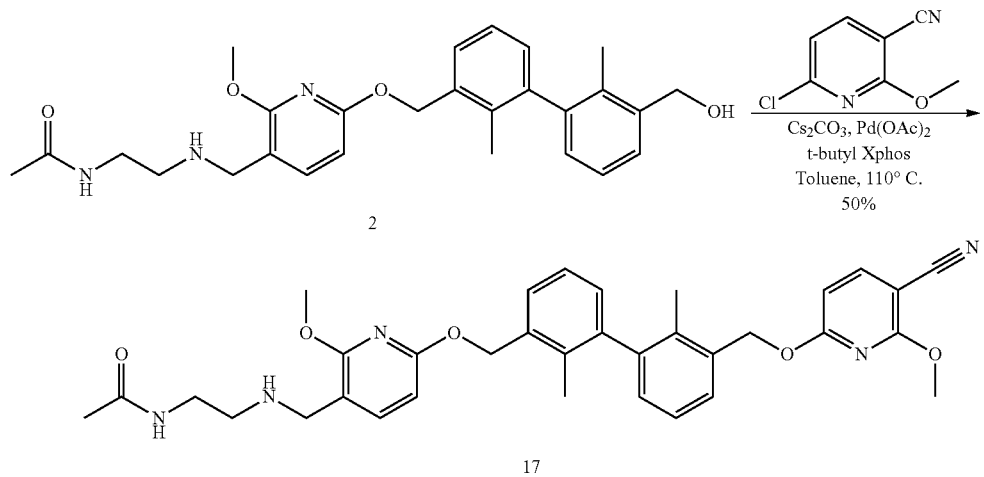

Palladium acetate (8.0 mg, 0.04 mmol) and 2-di-tert-butylphosphino-2',4',6'-triisopropylbiphenyl (8.0 mg, 0.02 mmol) was added to a mixture of Example compound 2 (223.0 mg, 1.0 mmol), 6-chloro-2-methoxy-3-pyridinecarbonitrile (8.0 mg, 0.05 mmol), cesium carbonate (33.0 mg, 0.1 mmol) in toluene (2 mL). The mixture was exchanged with nitrogen for 3 minutes, and was allowed to react at 100° C. under nitrogen in sealed vessel overnight. The reaction mixture was concentrated, and the crude product was separated and purified by silica gel column chromatography (eluted with petroleum ether/ethyl acetate=1/10) to obtain target compound example 17 (15.0 mg, 50%) as a white solid.

MS (ESI): m/z=596.3 [M+H]$^+$.

$^1$H NMR (400 MHz, CDCl$_3$) δ 7.71 (d, J=8.3 Hz, 1H), 7.45-7.33 (m, 3H), 7.24-7.19 (m, 2H), 7.12 (dd, J=7.6, 1.4 Hz, 1H), 7.08 (dd, J=7.6, 1.5 Hz, 1H), 6.48 (s, 1H), 6.42 (d, J=8.3 Hz, 1H), 6.34 (d, J=8.0 Hz, 1H), 5.46 (s, 2H), 5.39 (s, 2H), 4.34-4.26 (m, 2H), 4.04 (s, 3H), 3.93 (s, 3H), 3.44-3.31 (m, 4H), 2.05 (s, 6H), 1.91 (s, 3H).

Example 18

N,N-((((((pyridine-2,6-diyl-bis(methylene)) bis(oxo)) bis (2-methoxypyridine-6,3-diyl)) bis (methylene)) bis (azetanediyl)) bis (ethane-2,1-diyl)) diacetamide

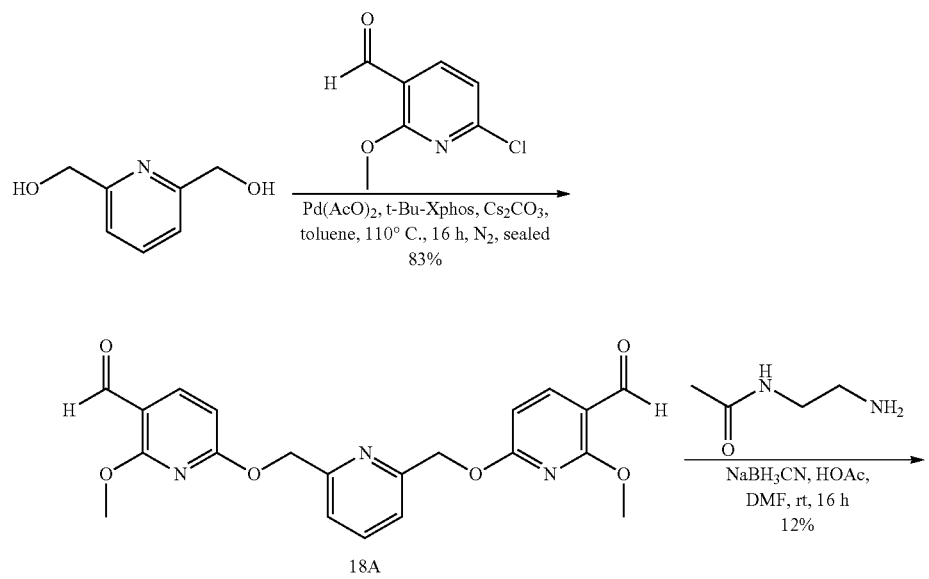

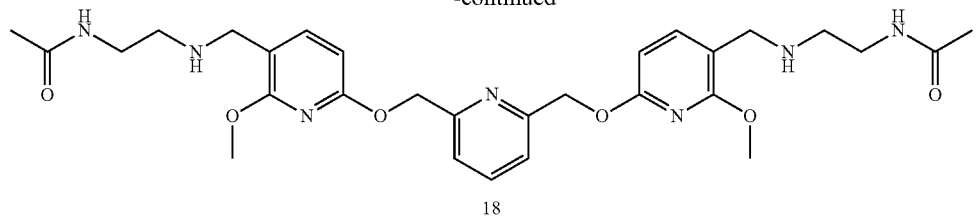

18

6,6'-((pyridine-2,6-diyl-bis (methylene)) bis (oxo)) bis (2-methoxynicotyraldehyde)

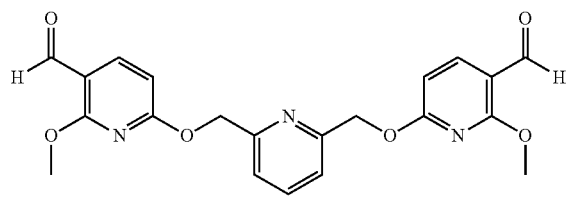 [SMILES: COc1nc(OCc2cccc(COc3ccc(C=O)c(OC)n3)n2)ccc1C=O]

Palladium acetate (22.0 mg, 0.1 mmol) and 2-di-tert-butylphosphino-2',4',6'-triisopropylbiphenyl (85.0 mg, 0.2 mmol) was added to pyridine-2,6-diyl-dimethanol (70.0 mg, 0.5 mmol), 6-chloro-2-methoxynicotyraldehyde (214 mg, 1.25 mmol), cesium carbonate (977.0 mg, 3.0 mmol) in toluene (5 mL). The mixture was exchanged by bubbling nitrogen for 1 minute. Then the mixture was quickly capped and sealed, heated to 110° C., and reacted overnight at that temperature. The reaction mixture was filtered through celite, the filtrate was concentrated, and the residue was separated and purified with combiflash column chromatography (eluted with petroleum ether/ethyl acetate=4/1) to obtain the target compound 18A (170.0 mg, 83%) as a white solid.

MS (ESI): m/z=410.1 [M+H]$^+$.

N,N-((((((pyridine-2,6-diyl-bis (methylene)) bis (oxo)) bis (2-methoxypyridine-6,3-diyl)) bis (methylene)) bis (azetanediyl)) bis (ethane-2,1-diyl)) diacetamide (Compound 18)

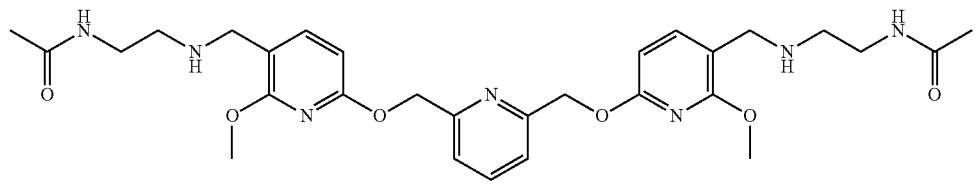 [SMILES: COc1nc(OCc2cccc(COc3ccc(CNCCNC(C)=O)c(OC)n3)n2)ccc1CNCCNC(C)=O]

Acetic acid (3 drops) was added to a mixture of compound 18A (170.0 mg, 0.42 mmol) and N-(2-aminoethyl) acetamide (129.0 mg, 1.26 mmol) in N,N-dimethylformamide (3 mL). The mixture was stirred at room temperature for one hour, then sodium cyanoborohydride (79.0 mg, 1.26 mmol) was added to mixture and the mixture was stirred at room temperature overnight. The reaction mixture was separated and purified by combiflash column chromatography (eluted with acetonitrile/ammonium bicarbonate aqueous solution (10 mmol/L)=30%) to obtain example compound 18 (30.0 mg, 12%) as a transparent gum.

MS (ESI): m/z=291.7 [M/2+H]$^+$.

$^1$H NMR (400 MHz, CD$_3$OD) δ 7.77 (t, J=7.8 Hz, 1H), 7.53 (d, J=7.9 Hz, 2H), 7.39 (d, J=7.8 Hz, 2H), 6.42 (d, J=7.9 Hz, 2H), 5.44 (s, 4H), 3.80 (s, 6H), 3.63 (s, 4H), 3.29-3.24 (m, 4H), 2.64 (t, J=6.4 Hz, 4H), 1.90 (s, 6H).

Example 19

N,N'-(((((((2-methyl-1,3-phenylene) bis (methylene)) bis (oxo)) bis (2-methoxypyridine-6,3-diyl)) bis (methylene)) bis (azetanediyl)) bis (ethane-2,1-diyl)) diacetamide

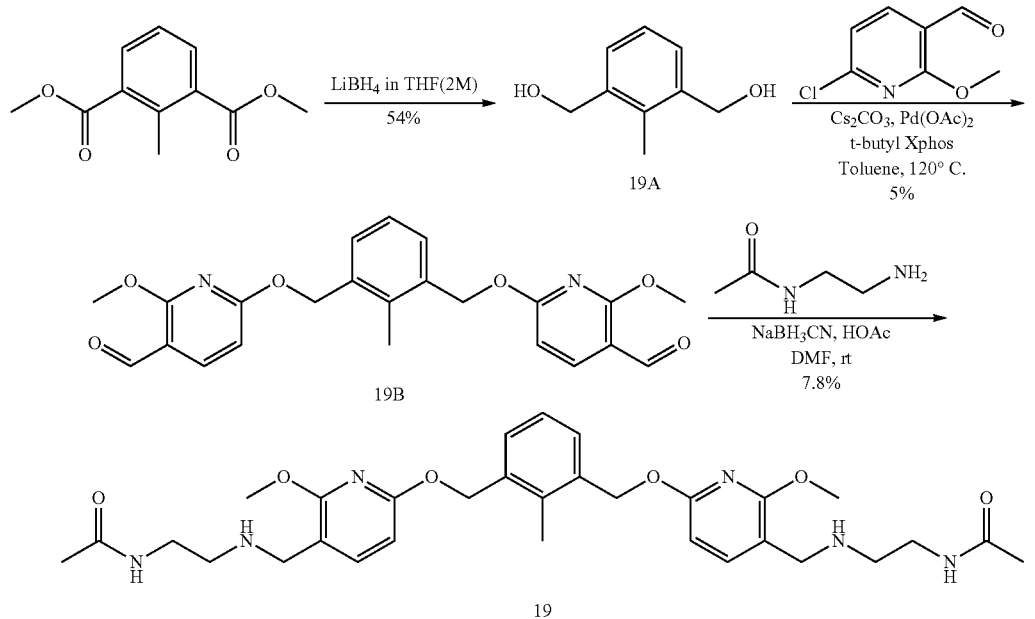

(2-methyl-1,3-phenylene) dimethanol 6,6'-(((2-methyl-1,3-phenylene) bis (methylene)) bis (oxo)) bis (2-methoxynicotyraldehyde)

Under 0° C., a solution of lithium borohydride in tetrahydrofuran (2 M, 19 mL, 37.5 mmol) was added to dimethyl 2-methylisophthalate (780.0 mg, 3.75 mmol), and the reaction was carried out at room temperature under nitrogen atmosphere overnight. The mixture was quenched by adding methanol (20 mL) and water (5 mL), neutralized to neutral with dilute hydrochloric acid (1 M), and concentrated. The residue was separated and purified by reversed-phase column chromatography (methanol/water), and the product was filtered through silica gel (eluted with ethyl acetate). The filtrate was concentrated to obtain the target compound 19A (310.0 mg, 54%) as a white solid.

MS (ESI): m/z=135.1 [M-17]$^+$.

$^1$H NMR (400 MHz, DMSO-d$_6$) δ7.22 (d, J=7.6 Hz, 2H), 7.09 (t, J=7.5 Hz, 1H), 4.97 (t, J=5.4 Hz, 2H), 4.46 (d, J=5.4 Hz, 4H), 2.12 (s, 3H).

Palladium acetate (53.0 mg, 0.23 mmol) and 2-di-tert-butylphosphino-2',4',6'-triisopropylbiphenyl (200.0 mg, 0.47 mmol) were added to a mixture of compound 19A (120.0 mg, 0.78 mmol), 6-chloro-2-methoxynicotyraldehyde (270.0 mg, 1.57 mmol) and cesium carbonate (1029.0 mg, 3.15 mmol) in toluene (7 mL). The mixture was exchanged with nitrogen for 5 minutes, and reacted at 120° C. under nitrogen in sealed vessel overnight. The reaction mixture was filtered through celite, the filtrate was concentrated, and the residue was separated and purified by combiflash column chromatography (eluted with petroleum ether/ethyl acetate=8/1), and the product was further purified by combiflash column chromatography (methanol/water) to obtain the target compound 19B (18.0 mg, 5%) as a white solid.

MS (ESI): m/z=423.1 [M+H]$^+$.

N,N'-(((((((2-methyl-1,3-phenylene) bis (methylene)) bis (oxo)) bis (2-methoxypyridine-6,3-diyl)) bis (methylene)) bis (azetanediyl)) bis (ethane-2,1-diyl)) diacetamide (Compound 19)

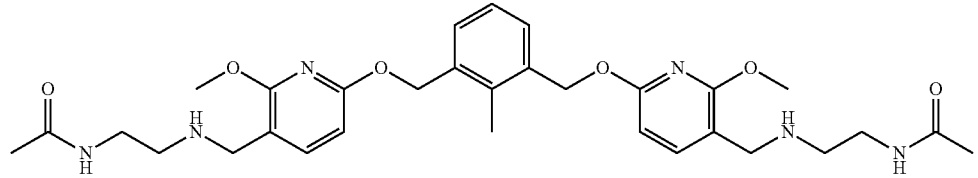 [SMILES: COc1nc(OCc2cccc(COc3ccc(CNCCNC(C)=O)c(OC)n3)c2C)ccc1CNCCNC(C)=O]

Acetic acid (1 drop) was added to a mixture of compound 19B (18.0 mg, 0.042 mmol) and N-(2-aminoethyl) acetamide (17.0 mg, 0.17 mmol) in N,N-dimethylformamide (3 mL). The mixture was stirred at room temperature for one hour, then sodium cyanoborohydride (11.0 mg, 0.17 mmol) was added and the mixture was stirred at room temperature overnight. The reaction mixture was separated and purified by combiflash column chromatography (eluted with acetonitrile/ammonium bicarbonate aqueous solution (10 mmol/L)) to obtain example compound 19 (2.0 mg, 7.8%) as a white solid.

MS (ESI): m/z=298.2 [M/2+H]+.

$^1$H NMR (400 MHz, DMSO-$d_6$) δ 7.74 (s, 2H), 7.57 (d, J=7.8 Hz, 2H), 7.38 (d, J=7.5 Hz, 2H), 7.16 (t, J=7.7 Hz, 1H), 6.35 (d, J=7.8 Hz, 2H), 5.34 (s, 4H), 3.84 (s, 6H), 3.52 (s, 3H), 3.23 (s, 4H), 3.10-3.04 (m, 4H), 2.31 (s, 4H), 1.74 (s, 6H).

Example 20

1,1'-(((((((2,2'-dimethyl-[1,1'-biphenyl]-3,3'-diyl) bis (methylene)) bis (oxo)) bis (2-methoxypyridine-6,3-diyl)) bis (methylene)) bis (azetanediyl)) bis (2-methylpropane-2-ol) (Compound 20)

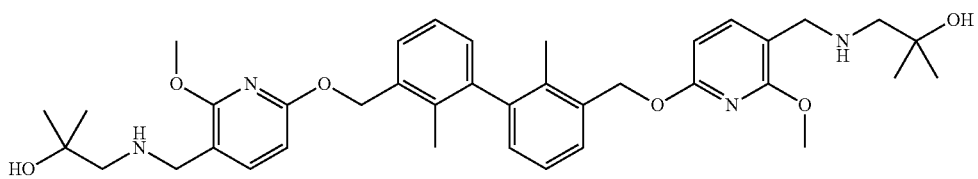 [SMILES: COc1nc(OCc2cccc(-c3cccc(COc4ccc(CNCC(C)(C)O)c(OC)n4)c3C)c2C)ccc1CNCC(C)(C)O]

The target compound was prepared from compound 4A and 1-amino-2-methyl-2-propanol under conditions similar to those of example 4.

MS (ESI): m/z=330.2[1/2M+H]$^+$.

$^1$H NMR (400 MHz, CD$_3$OD) δ 7.51 (d, J=7.9 Hz, 2H), 7.40 (d, J=7.3 Hz, 2H), 7.20 (t, J=7.6 Hz, 2H), 7.02 (d, J=7.6 Hz, 2H), 6.35 (d, J=7.9 Hz, 2H), 5.41 (s, 4H), 3.93 (s, 6H), 3.65 (s, 4H), 2.48 (s, 4H), 2.03 (s, 6H), 1.17 (s, 12H).

Example 21

2,2'-(((((((2,2'-dimethyl-[1,1'-biphenyl]-3,3'-diyl) bis (methylene)) bis (oxo)) bis (2-methoxypyridine-6,3-diyl)) bis (methylene)) bis (azetanediyl)) bis (ethane-1-ol) (Compound 21)

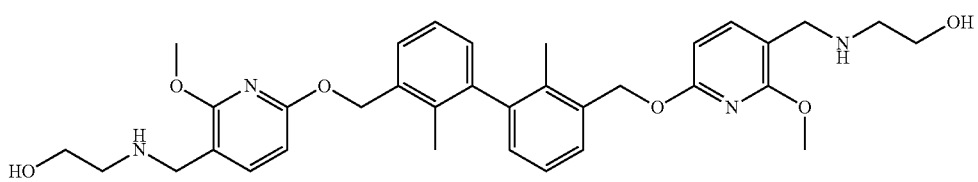 [SMILES: COc1nc(OCc2cccc(-c3cccc(COc4ccc(CNCCO)c(OC)n4)c3C)c2C)ccc1CNCCO]

The target compound was prepared from compound 4A and ethanolamine under conditions similar to those of example 4.

MS (ESI): m/z=302.2[1/2M+H]$^+$.

$^1$H NMR (400 MHz, CD$_3$OD) δ 7.67 (d, J=8.0 Hz, 2H), 7.42 (d, J=7.5 Hz, 2H), 7.21 (t, J=7.6 Hz, 2H), 7.03 (d, J=7.3 Hz, 2H), 6.45 (d, J=8.0 Hz, 2H), 5.47 (s, 4H), 4.12 (s, 4H), 4.01 (s, 6H), 3.78 (t, J=4.0 Hz, 4H), 3.07 (t, J=4.0 Hz, 4H), 2.04 (s, 6H).

Example 22

3,3'-((((((2,2'-dimethyl[1,1'-biphenyl]-3,3'-diyl) bis (methylene)) bis (oxo)) bis (2-methoxypyridine-6,3-diyl)) bis (methylene)) bis (azetanediyl)) dipropionamide (Compound 22)

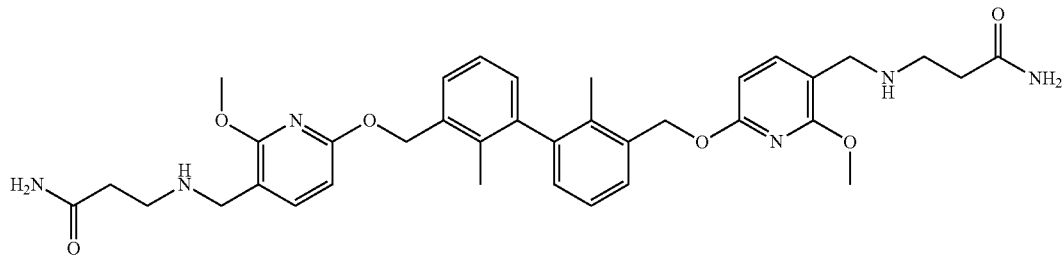 [SMILES: COc1nc(OCc2cccc(-c3cccc(COc4ccc(CNCCC(N)=O)c(OC)n4)c3C)c2C)ccc1CNCCC(N)=O]

The target compound was prepared from compounds 4A and 3-aminopropionamide under conditions similar to those of example 4.

MS (ESI): m/z=657.3[M+H]$^+$.

$^1$H NMR (400 MHz, CD$_3$OD) δ 7.65 (d, J=8.0 Hz, 2H), 7.42 (d, J=7.4 Hz, 2H), 7.21 (t, J=7.6 Hz, 2H), 7.03 (d, J=7.5 Hz, 2H), 6.45 (d, J=8.0 Hz, 2H), 5.47 (s, 4H), 4.10 (s, 4H), 4.02 (s, 6H), 3.21 (t, J=6.1 Hz, 4H), 2.65 (t, J=6.2 Hz, 4H), 2.04 (s, 6H).

Each of the following compounds was prepared by a method similar to that of Example 1-22, by using the corresponding raw materials:

TABLE 1

| No. | Compound structure | LCMS, HNMR |
|---|---|---|
| 23 | 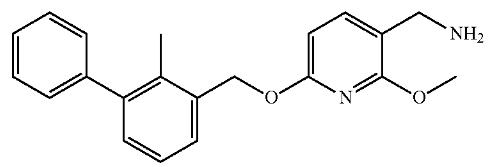 | MS (ESI): m/z = 318.1 [M + H]+. ¹H NMR (400 MHz, DMSO-d$_6$) δ 7.47 (d, J = 8.0 Hz, 1H), 7.44-7.37 (m, 3H), 7.37-7.29 (m, 1H), 7.29-7.24 (m, 2H), 7.22 (t, J = 7.6 Hz, 1H), 7.17-7.16 (m, 1H), 7.16-7.09 (m, 1H), 6.98 (s, 1H), 6.38 (d, J = 7.9 Hz, 1H), 5.36 (s, 2H), 3.85 (s, 3H), 3.58 (s, 2H), 2.17 (s, 3H) |
| 24 | 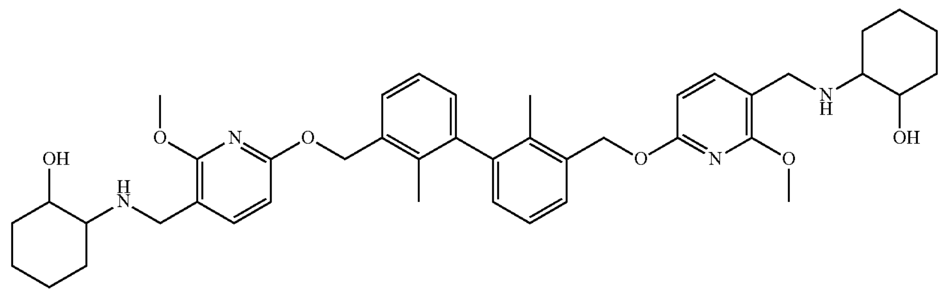 [SMILES: COc1nc(OCc2cccc(-c3cccc(COc4ccc(CNC5CCCCC5O)c(OC)n4)c3C)c2C)ccc1CNC1CCCCC1O] | MS (ESI): m/z = 711.4 [M + H]+. ¹H NMR (400 MHz, CD$_3$OD) δ 8.40 (m, 3H), 7.67 (dd, J = 8.0, 5.3 Hz, 2H), 7.42 (d, J = 7.6 Hz, 2H), 7.21 (m, 2H), 7.03 (d, J = 7.5 Hz, 2H), 6.45 (d, J = 8.0 Hz, 2H), 5.47 (d, J = 3.8 Hz, 4H), 4.14 (m, 4H), 4.06-3.98 (m, 6H), 3.18-3.04 (m, 2H), 2.91-2.67 (m, 1H), 2.29-2.14 (m, 1H), 2.04 (s, 6H), 1.91-1.26 (m, 16H). |
| 25 | 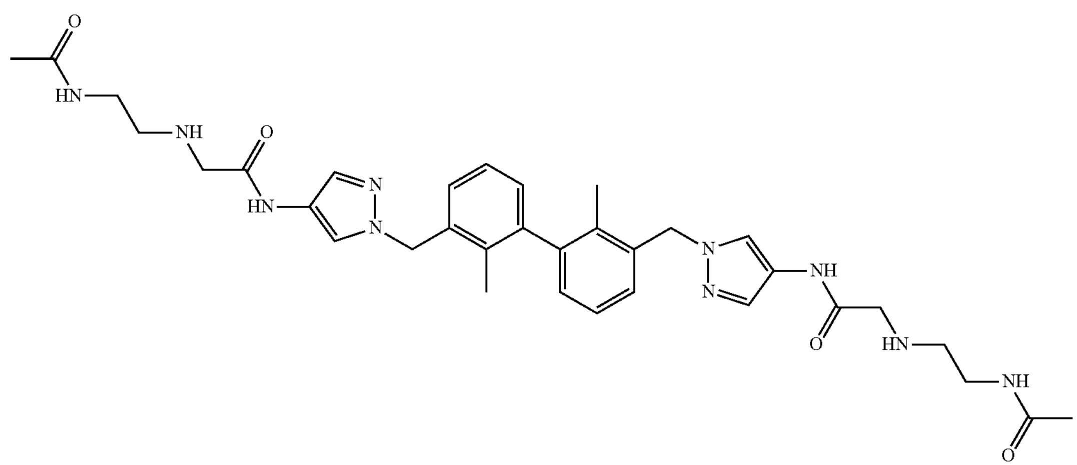 [SMILES: CC(=O)NCCNCC(=O)Nc1cnn(Cc2cccc(-c3cccc(Cn4cc(NC(=O)CNCCNC(C)=O)cn4)c3C)c2C)c1] | MS: [M + H]+ m/z 657.2. ¹H NMR (400 MHz, DMSO-d$_6$) δ 9.95 (s, 2H), 8.18 (s, 2H), 7.91-7.87 (m, 4H), 7.54 (s, 2H), 7.17 (m, 2H), 6.97 (d, J = 6.8 Hz, 2H), 6.83 (d, J = 7.6 Hz, 2H), 5.32 (s, 4H), 3.27 (s, 4H), 3.14-3.10 (m, 4H), 2.59-2.57 (m, 4H), 1.89 (s, 6H), 1.77 (s, 6H) |

TABLE 1-continued

| No. | Compound structure | LCMS, HNMR |
|---|---|---|
| 26 | 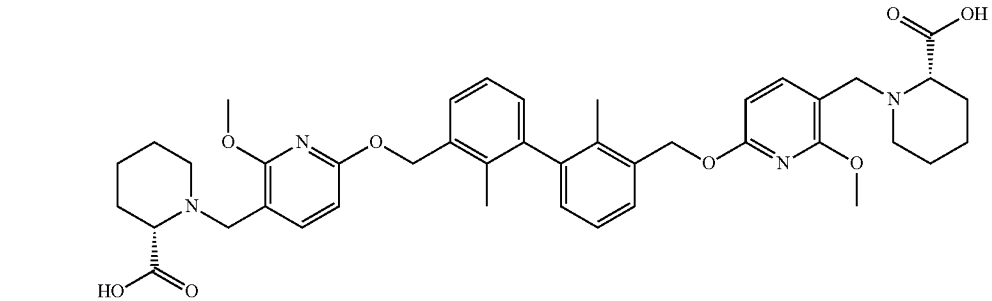 | MS (ESI): m/z = 739.3[M + H]⁺. ¹H NMR (400 MHz, CD₃OD) δ 8.18 (s, 2H), 7.79 (d, J = 8.1 Hz, 2H), 7.46 (d, J = 7.4 Hz, 2H), 7.25 (m, 2H), 7.12-7.01 (m, 2H), 6.52 (d, J = 8.1 Hz, 2H), 5.52 (s, 4H), 4.34 (m, 4H), 4.03 (s, 6H), 3.46 (m, 4H), 2.97 (m, 2H), 2.25 (m, 2H), 2.07 (s, 6H), 1.92-1.46 (m, 10H) |
| 27 | 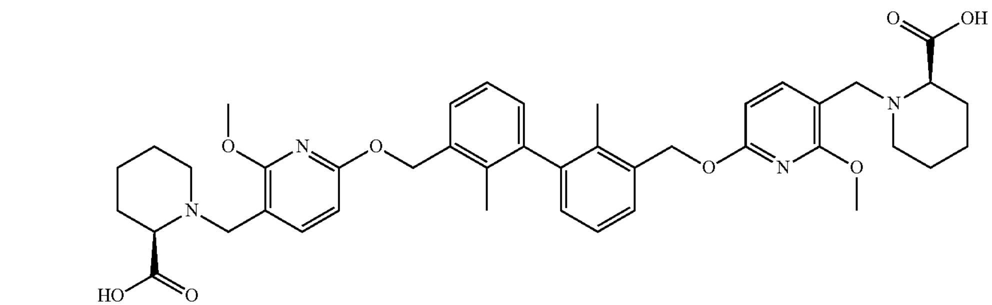 [SMILES: COc1nc(OCc2cccc(-c3cccc(COc4ccc(CN5CCCC[C@@H]5C(=O)O)c(OC)n4)c3C)c2C)ccc1CN1CCCC[C@@H]1C(=O)O] | MS (ESI): m/z = 739.3[M + H]⁺. ¹H NMR (400 MHz, CD₃OD) δ 8.18 (s, 2H), 7.79 (d, J = 8.1 Hz, 2H), 7.46 (d, J = 7.4 Hz, 2H), 7.25 (m, 2H), 7.12-7.01 (m, 2H), 6.52 (d, J = 8.1 Hz, 2H), 5.52 (s, 4H), 4.34 (m, 4H), 4.03 (s, 6H), 3.46 (m, 4H), 2.97 (m, 2H), 2.25 (m, 2H), 2.07 (s, 6H), 1.92-1.46 (m, 10H) |
| 28 | 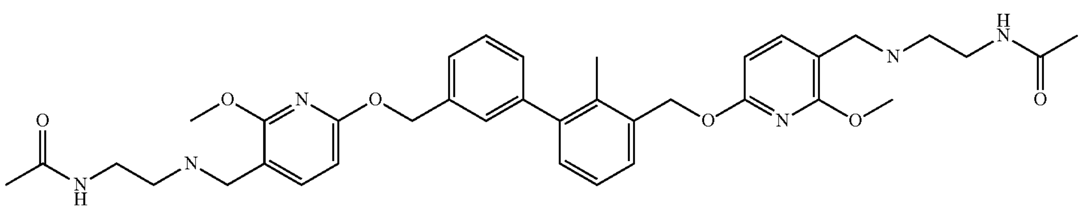 | MS-ESI: m/z 285.1 [M/2 + H]⁺. ¹H NMR (400 MHz, CD₃OD) δ 8.49 (s, 2H), 7.64 (dd, J = 8.1, 5.8 Hz, 2H), 7.41 (m, 3H), 7.33 (s, 1H), 7.22-7.17 (m, 2H), 7.13 (d, J = 6.6 Hz, 1H), 6.45 (d, J = 2.9 Hz, 1H), 6.43 (d, J = 2.9 Hz, 1H), 5.46 (d, J = 4.3 Hz, 4H), 4.05 (d, J = 8.1 Hz, 4H), 4.01 (s, 3H), 3.96 (s, 3H), 3.44 (m,4H), 3.05 (m, 4H), 2.20 (s, 3H), 1.94 (d, J = 3.5 Hz, 6H) |

TABLE 1-continued

| No. | Compound structure | LCMS, HNMR |
|---|---|---|
| 29 | 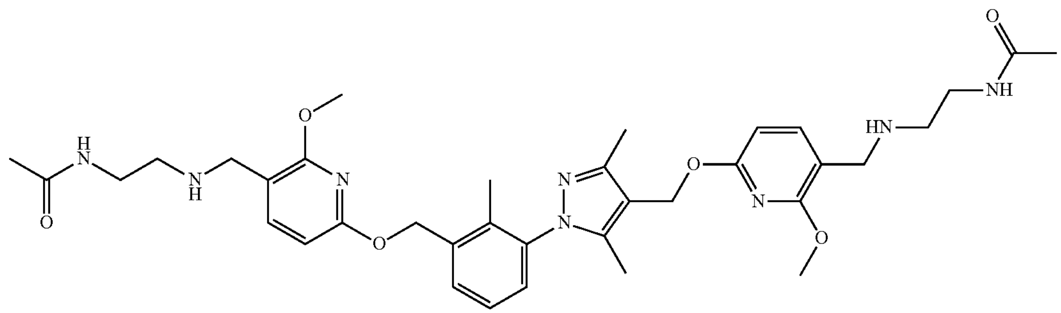 [SMILES: COc1nc(OCc2cccc(-n3nc(C)c(COc4ccc(CNCCNC(C)=O)c(OC)n4)c3C)c2C)ccc1CNCCNC(C)=O] | MS-ESI: m/z 345.2 [M/2 + H]+. ¹H NMR (400 MHz, CD₃OD) δ 7.59 (d, J = 7.5 Hz, 1H), 7.52 (dd, J = 7.9, 1.6 Hz, 2H), 7.33 (m, 1H), 7.21 (d, J = 7.7 Hz, 1H), 6.33 (m, 2H), 5.45 (s, 2H), 5.28 (s, 2H), 3.99 (s, 3H), 3.93 (s, 3H), 3.65 (d, J = 7.2 Hz, 3H), 3.29 (m, 4H), 2.65 (m, 4H), 2.28 (s, 3H), 2.07 (s, 3H), 1.98 (s, 3H), 1.91 (d, J = 3.3 Hz, 6H) |
| 30 | 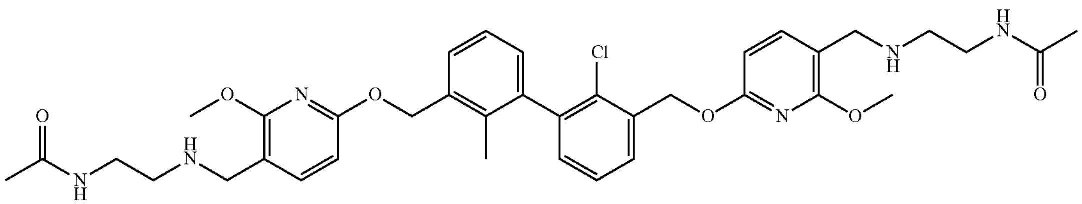 [SMILES: COc1nc(OCc2cccc(-c3cccc(COc4ccc(CNCCNC(C)=O)c(OC)n4)c3Cl)c2C)ccc1CNCCNC(C)=O] | MS-ESI: m/z 704.1[M + H]+. ¹H NMR (400 MHz, CD₃OD) δ 7.67 (m, 2H), 7.52 (d, J = 7.2 Hz, 1H), 7.45 (d, J = 7.6 Hz, 1H), 7.34 (m, 1H), 7.22 (m, 1H), 7.17 (d, J = 7.2 Hz, 1H), 7.06 (d, J = 7.2 Hz, 1H), 6.50 (d, J = 8.0 Hz, 1H), 6.44 (d, J = 8.0 Hz, 1H), 5.55 (s, 2H), 5.47 (m, 2H), 4.08 (s, 4H), 4.00 (s, 3H), 3.95 (s, 3H), 3.45 (m, 4H), 3.08 (m, 4H), 2.08 (s, 3H), 1.95 (s, 6H) |
| 31 | 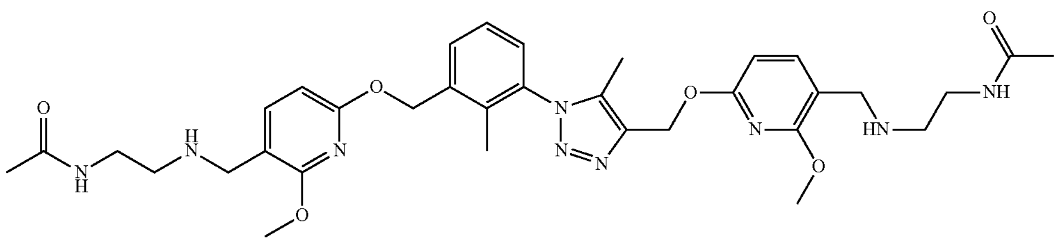 [SMILES: COc1nc(OCc2cccc(-n3nnc(COc4ccc(CNCCNC(C)=O)c(OC)n4)c3C)c2C)ccc1CNCCNC(C)=O] | MS-ESI: m/z 676.1[M + H]+. ¹H NMR (400 MHz, CD₃OD) δ 7.71-7.66 (m, 3H), 7.42 (m, 1H), 7.28 (d, J = 8.0 Hz, 1H), 6.47 (d, J = 8.0 Hz, 1H), 6.43 (d, J = 8.0 Hz, 1H), 5.56 (s, 2H), 5.53 (s, 2H), 4.11 (s, 2H), 4.09 (s, 2H), 4.06 (s, 3H), 4.00 (s, 3H), 3.47 (m, 4H), 3.10 (m, 4H), 2.19 (s, 3H), 1.99 (s, 3H), 1.95 (s, 3H), 1.94 (s, 3H) |
| 32 | 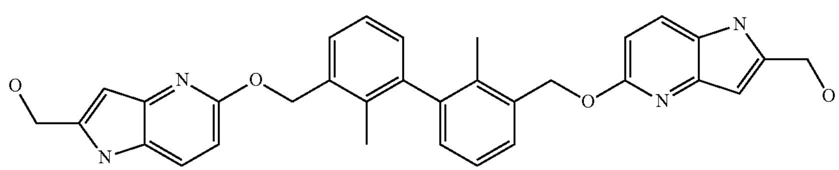 [SMILES: Cc1c(COc2ccc3[nH]c(CO)cc3n2)cccc1-c1cccc(COc2ccc3[nH]c(CO)cc3n2)c1C] | MS (ESI): m/z = 535.0[M + H]+. ¹H NMR (400 MHz, DMSO-d₆) δ 11.06 (brs, 2H), 7.61 (d, J = 8.8 Hz, 2H), 7.44 (d, J = 7.2 Hz, 2H), 7.22 (m, 2H), 7.04 (d, J = 7.6 Hz, 2H), 6.54 (d, J = 8.8 Hz, 2H), 6.23 (s, 2H), 5.36 (brs, 4H), 5.27 (m, 2H), 4.58 (d, J = 5.2 Hz, 4H), 2.00 (s, 6H) |

TABLE 1-continued

| No. | Compound structure | LCMS, HNMR |
|---|---|---|
| 33 | 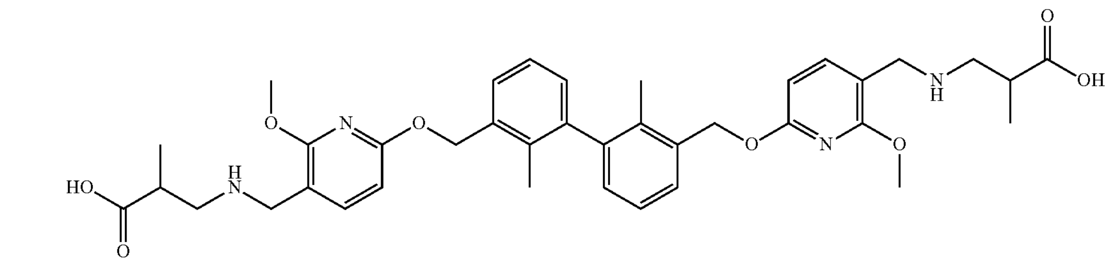 [SMILES: COc1nc(OCc2cccc(-c3cccc(COc4ccc(CNCC(C)C(=O)O)c(OC)n4)c3C)c2C)ccc1CNCC(C)C(=O)O] | MS (ESI): m/z = 687.1[M + H]+. 1H NMR (400 MHz, CD3OD) δ 7.63 (d, J = 8.0 Hz, 2H), 7.41 (d, J = 7.7 Hz, 2H), 7.20 (m, 2H), 7.03 (d, J = 7.6 Hz, 2H), 6.43 (d, J = 7.9 Hz, 2H), 5.45 (m, 4H), 4.08 (s, 4H), 4.02 (s, 6H), 2.98 (m, 4H), 2.54 (d, J = 7.4 Hz, 2H), 2.03 (s, 6H), 1.18 (d, J = 7.3 Hz, 6H) |
| 34 | 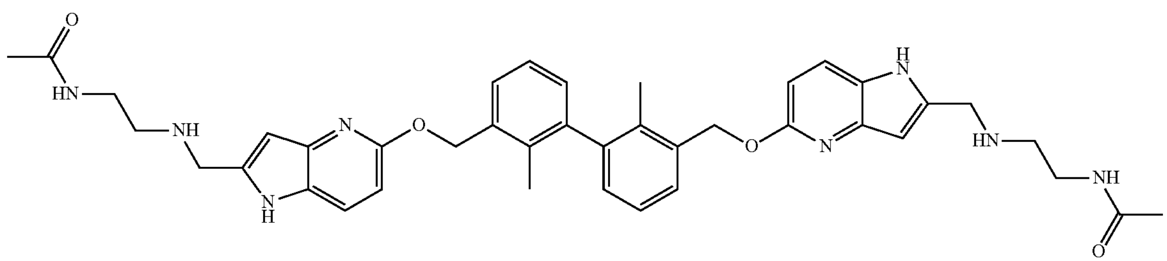 [SMILES: CC(=O)NCCNCc1cc2nc(OCc3cccc(-c4cccc(COc5ccc6[nH]c(CNCCNC(C)=O)cc6n5)c4C)c3C)ccc2[nH]1] | MS (ESI): m/z = 703.2[M + H]+. 1H NMR (400 MHz, CDCl3) δ 7.65 (d, J = 8.8 Hz, 2H), 7.45 (d, J = 7.2 Hz, 2H), 7.23 (m, 2H), 7.06 (d, J = 6.4 Hz, 2H), 6.62 (d, J = 8.8 Hz, 2H), 6.39 (s, 2H), 5.38 (s, 4H), 3.92 (s, 4H), 3.31-3.29 (m, 4H), 2.72 (m, 4H), 2.06 (s, 6H), 1.91 (s, 6H) |
| 35 | 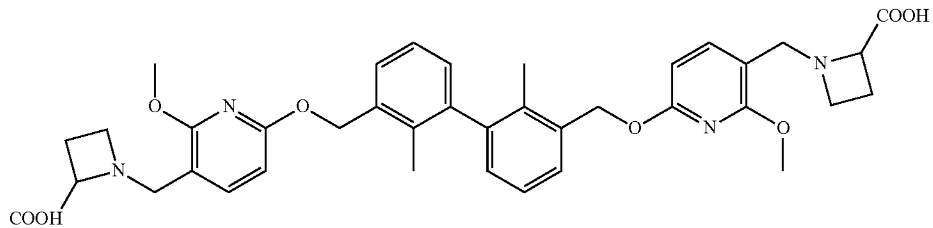 [SMILES: COc1nc(OCc2cccc(-c3cccc(COc4ccc(CN5CCC5C(=O)O)c(OC)n4)c3C)c2C)ccc1CN1CCC1C(=O)O] | MS (ESI): m/z = 683.1[M + H]+. 1H NMR (400 MHz, CD3OD) δ 8.38 (s, 1H), 7.65 (d, J = 8.1 Hz, 2H), 7.41 (d, J = 7.3 Hz, 2H), 7.21 (m, 2H), 7.04 (d, J = 6.6 Hz, 2H), 6.42 (d, J = 8.0 Hz, 2H), 5.45 (s, 4H), 4.60 (m, 2H), 4.24 (m, 4H), 3.99 (m, 6H), 3.93 (m, 2H), 3.89-3.79 (m, 2H), 2.67-2.57 (m, 2H), 2.46-2.35 (m, 2H), 2.03 (s, 6H). |

TABLE 1-continued

| No. | Compound structure | LCMS, HNMR |
|---|---|---|
| 36 | 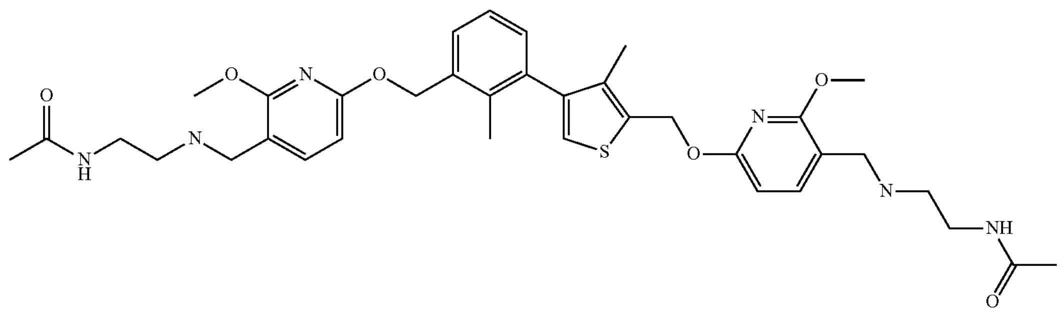 [SMILES: COc1nc(OCc2cccc(-c3csc(COc4ccc(CNCCNC(C)=O)c(OC)n4)c3C)c2C)ccc1CNCCNC(C)=O] | MS (ESI): m/z = 691.2[M + H]⁺. ¹H NMR (400 MHz, CD₃OD) δ 7.51 (d, J = 7.9 Hz, 2H), 7.40 (d, J = 7.0 Hz, 1H), 7.17 (s, 1H), 7.08-7.02 (m, 2H), 6.36-6.27 (m, 2H), 5.52 (s, 2H), 5.40 (s, 2H), 4.01 (s, 3H), 3.93 (s, 3H), 3.65 (s, 2H), 3.63 (s, 2H), 3.32-3.22 (m, 4H), 2.68-2.60 (m, 4H), 2.10 (s, 3H), 1.97 (s, 3H), 1.91 (s, 3H), 1.90 (s, 3H) |
| 37 | 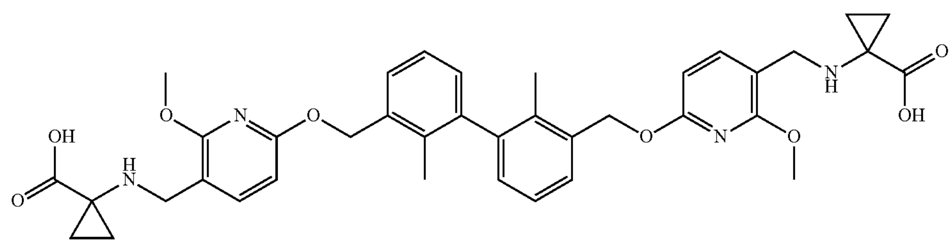 [SMILES: COc1nc(OCc2cccc(-c3cccc(COc4ccc(CNC5(C(=O)O)CC5)c(OC)n4)c3C)c2C)ccc1CNC1(C(=O)O)CC1] | MS (ESI): m/z = 683.1[M + H]⁺. ¹H NMR (400 MHz, CD₃OD) δ 8.50 (s, 1H), 7.72 (d, J = 8.4 Hz, 2H), 7.45 (d, J = 6.4 Hz, 2H), 7.23 (m, 2H), 7.03 (d, J = 7.5 Hz, 2H), 6.47 (d, J = 8.4 Hz, 2H), 5.50 (s, 4H), 4.29 (s, 3H), 4.03 (s, 6H), 2.07 (s, 6H), 1.40-1.18 (m, 5H), 0.92 (m, 4H) |
| 38 | 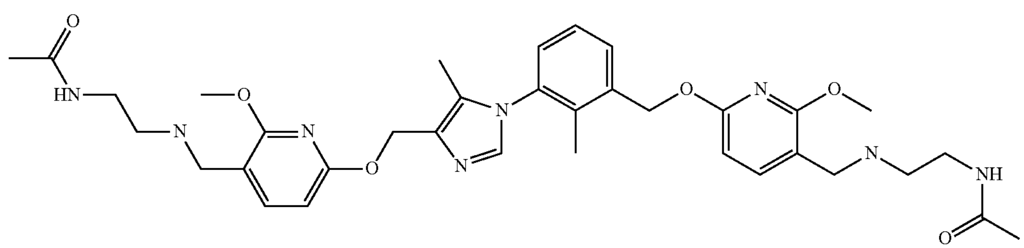 [SMILES: COc1nc(OCc2cccc(-n3cnc(COc4ccc(CNCCNC(C)=O)c(OC)n4)c3C)c2C)ccc1CNCCNC(C)=O] | MS (ESI): m/z = 675.1[M + H]⁺. ¹H NMR (400 MHz, CD₃OD) δ 8.48 (s, 2H), 7.70-7.60 (m, 4H), 7.37 (m, 1H), 7.27-7.21 (m, 1H), 6.46 (d, J = 8.0 Hz, 1H), 6.41 (d, J = 8.0 Hz, 1H), 5.51 (s, 2H), 5.40-5.31 (m, 2H), 4.11 (s, 2H), 4.10 (s, 2H), 4.06 (s, 3H), 4.01 (s, 3H), 3.53-3.40 (m, 4H), 3.10 (m, 4H), 2.04 (s, 3H), 2.03 (s, 3H), 1.96 (s, 3H), 1.95 (s, 3H) |

TABLE 1-continued

| No. | Compound structure | LCMS, HNMR |
|---|---|---|
| 39 | 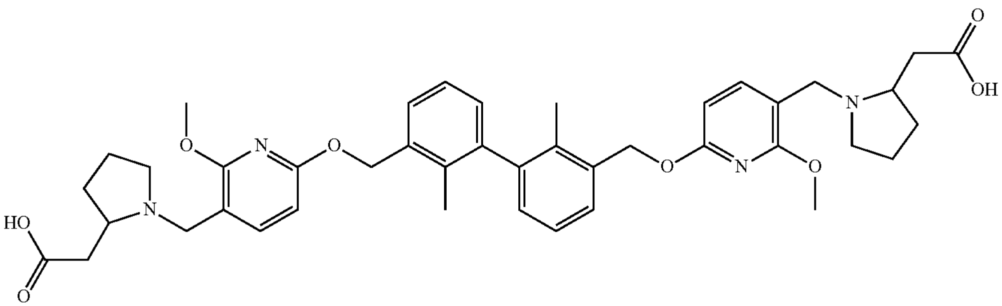 [SMILES: COc1nc(OCc2cccc(-c3cccc(COc4ccc(CN5CCCC5CC(=O)O)c(OC)n4)c3C)c2C)ccc1CN1CCCC1CC(=O)O] | MS (ESI): m/z = 739.1[M + H]⁺. ¹H NMR (400 MHz, CD₃OD) δ 7.69 (d, J = 8.1 Hz, 2H), 7.42 (d, J = 7.0 Hz, 2H), 7.21 (m, 2H), 7.04 (d, J = 6.7 Hz, 2H), 6.45 (d, J = 8.0 Hz, 2H), 5.53-5.36 (m, 4H), 4.43 (m, 2H), 4.07 (m, 2H), 3.75-3.60 (m, 2H), 3.47-3.34 (m, 2H), 3.16 (m, 2H), 2.65 (m, 2H), 2.51 (m, 2H), 2.33 (m, 2H), 2.10-1.87 (m, 10H), 1.89-1.69 (m, 2H) |
| 40 | 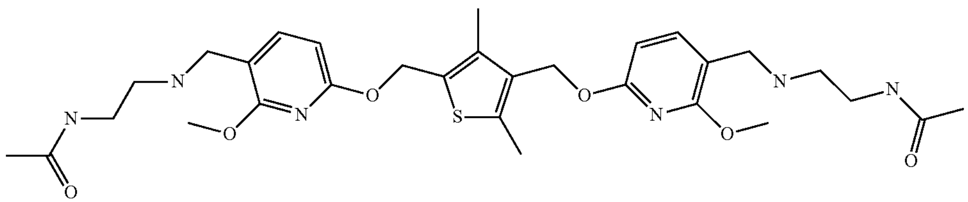 [SMILES: COc1nc(OCc2sc(C)c(COc3ccc(CNCCNC(C)=O)c(OC)n3)c2C)ccc1CNCCNC(C)=O] | MS (ESI): m/z = 615.0[M + H]⁺. ¹H NMR (400 MHz, CD₃OD) δ 7.54 (d, J = 8.0 Hz,1H), 7.53 (d, J = 8.0 Hz, 1H), 6.31 (d, J = 8.0 Hz, 1H), 6.30 (d, J = 8.0 Hz, 1H), 5.46 (s, 2H), 5.25 (s, 2H), 4.04 (s, 3H), 4.01(s, 3H), 3.70 (s, 2H), 3.69 (s, 2H), 3.31-3.36 (m, 4H), 2.70 (m, 2H), 2.69 (m, 2H), 2.45 (s, 3H), 2.25 (s, 3H), 1.95 (s, 3H), 1.94 (s, 3H) |
| 41 | 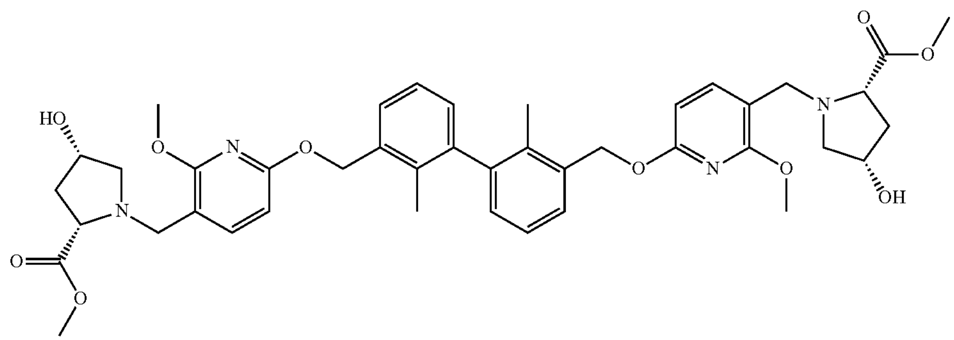 [SMILES: COC(=O)[C@@H]1C[C@H](O)CN1Cc1ccc(OCc2cccc(-c3cccc(COc4ccc(CN5C[C@@H](O)C[C@H]5C(=O)OC)c(OC)n4)c3C)c2C)nc1OC] | MS (ESI): m/z = 771.1[M + H]⁺. ¹H NMR (400 MHz, CD₃OD) δ 8.30 (s, 2H), 7.59 (d, J = 8.0 Hz, 2H), 7.41 (d, J = 7.3 Hz, 2H), 7.21 (m, 2H), 7.03 (d, J = 7.4 Hz, 2H), 6.39 (d, J = 8.0 Hz, 2H), 5.44 (s, 4H), 4.28 (s, 2H), 3.93 (s, 6H), 3.86 (s, 4H), 3.63 (s, 6H), 3.54 (m, 2H), 3.11 (m, 2H), 2.79 (m, 2H), 2.53 (m, 2H), 2.04 (s, 6H), 1.88 (m, 2H) |
| 42 | 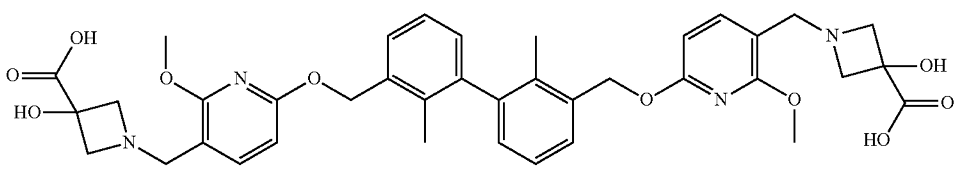 [SMILES: COc1nc(OCc2cccc(-c3cccc(COc4ccc(CN5CC(O)(C(=O)O)C5)c(OC)n4)c3C)c2C)ccc1CN1CC(O)(C(=O)O)C1] | MS (ESI): m/z = 715.0[M + H] ⁺ ¹H NMR (400 MHz, CD₃OD) δ 8.22 (s, 2H), 7.69 (d, J = 8.1 Hz, 2H), 7.42 (d, J = 7.3 Hz, 2H), 7.21 (m, 2H), 7.04 (d, J = 7.5 Hz, 2H), 6.46 (d, J = 8.0 Hz, 2H), 5.55-5.36 (m, 4H), 4.53-4.23 (m, 8H), 4.21-3.82 (m, 10H), 1.99 (s, 6H) |

TABLE 1-continued

| No. | Compound structure | LCMS, HNMR |
|---|---|---|
| 43 | 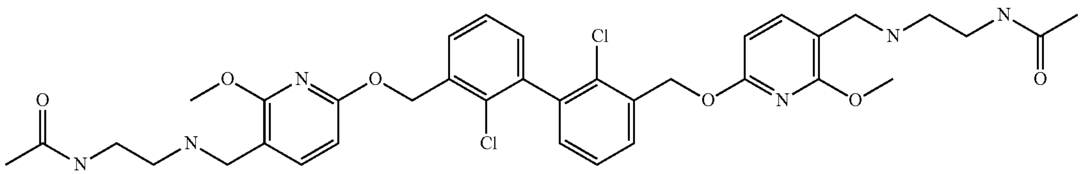 [SMILES: COc1nc(OCc2cccc(-c3cccc(COc4ccc(CNCCNC(C)=O)c(OC)n4)c3Cl)c2Cl)ccc1CNCCNC(C)=O] | MS (ESI): m/z = 725.0[M + H]⁺. ¹H NMR (400 MHz, CD₃OD) δ 7.71 (d, J = 8.1 Hz, 2H), 7.56 (dd, J = 7.7, 1.4 Hz, 2H), 7.37 (m, 2H), 7.22 (dd, J = 7.6, 1.5 Hz, 2H), 6.53 (d, J = 8.0 Hz, 2H), 5.58 (m, 4H), 4.13 (s, 4H), 3.97 (s, 6H), 3.48 (m, 4H), 3.12 (m, 4H), 1.96 (s, 6H) |
| 44 | 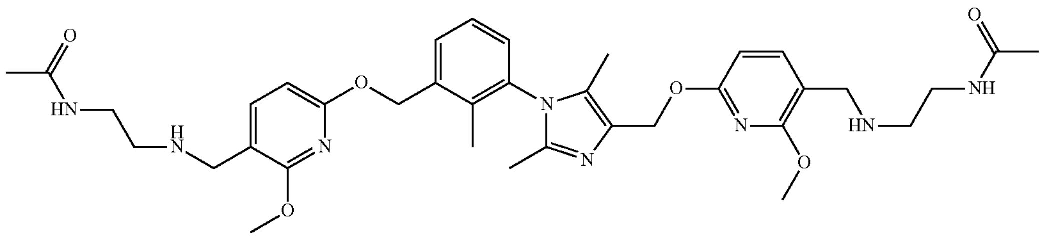 [SMILES: COc1nc(OCc2cccc(-n3c(C)nc(COc4ccc(CNCCNC(C)=O)c(OC)n4)c3C)c2C)ccc1CNCCNC(C)=O] | MS-ESI: m/z 689[M + H]+. ¹H NMR (400 MHz, CD3OD) δ 7.69-7.62 (m, 3H), 7.40 (m, 1H), 7.22 (d, J = 7.6 Hz, 1H), 6.47 (d, J = 8.0 Hz, 1H), 6.41 (d, J = 8.0 Hz, 1H), 5.52 (s, 2H), 5.31 (d, J = 3.2 Hz, 2H), 4.12 (m, 4H), 4.05 (s, 3H), 4.00 (s, 3H), 3.47 (m, 4H), 3.12 (m, 4H), 2.80(m, 1H), 2.07 (s, 3H), 1.99 (s, 3H), 1.96 (s, 3H), 1.95 (s, 6H) |
| 45 | 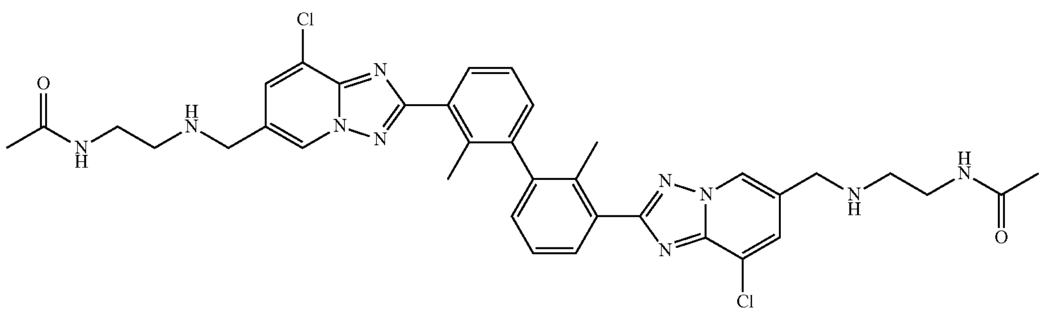 [SMILES: CC(=O)NCCNCc1cc(Cl)c2nc(-c3cccc(-c4cccc(-c5nc6c(Cl)cc(CNCCNC(C)=O)cn6n5)c4C)c3C)nn2c1] | MS (ESI): m/z = 713.0[M + H]⁺. ¹H NMR (400 MHz, CD₃OD) δ 8.77 (s, 2H), 7.89 (s, 1H), 7.87 (s, 3H), 7.42 (m, 2H), 7.31 (s, 1H), 7.29 (s, 1H), 3.91 (s, 4H), 3.33 (m, 4H), 2.76 (m, 4H), 2.29 (s, 6H), 1.93 (s, 6H) |

TABLE 1-continued

| No. | Compound structure | LCMS, HNMR |
|---|---|---|
| 46 | 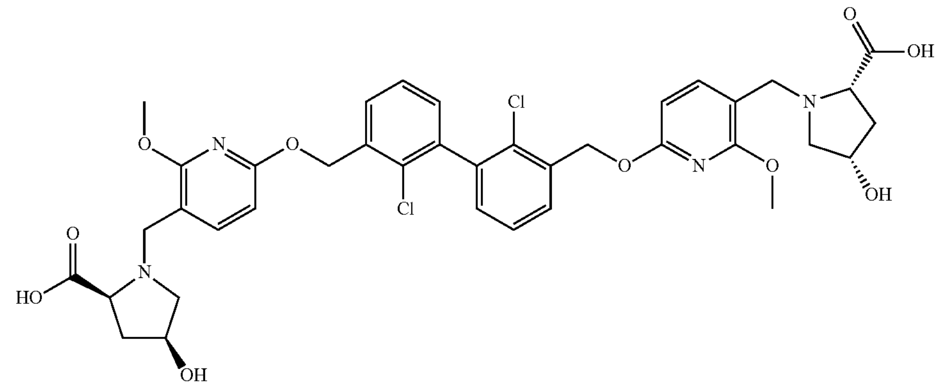 [SMILES: COc1nc(OCc2cccc(-c3cccc(COc4ccc(CN5C[C@@H](O)C[C@H]5C(=O)O)c(OC)n4)c3Cl)c2Cl)ccc1CN1C[C@@H](O)C[C@H]1C(=O)O] | MS (ESI): m/z = 783.0[M + H]⁺. ¹H NMR (400 MHz, CD₃OD) δ 7.70 (d, J = 8.1 Hz, 2H), 7.56 (d, J = 7.7 Hz, 2H), 7.37 (m, 2H), 7.22 (m, 2H), 6.51 (d, J = 8.0 Hz, 2H), 5.63-5.49 (m, 4H), 4.44-4.39 (m, 2H), 4.30 (m, 4H), 3.98 (s, 6H), 3.95-3.88 (m, 2H), 3.39 (m, 2H), 3.25-3.17 (m, 2H), 2.62-2.52 (m, 2H), 2.24-2.16 (m, 2H) |
| 47 | 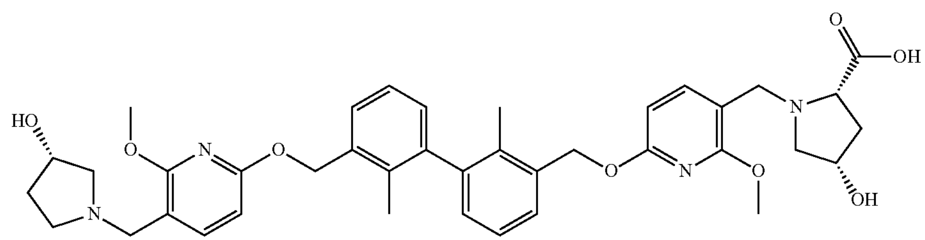 [SMILES: COc1nc(OCc2cccc(-c3cccc(COc4ccc(CN5C[C@@H](O)C[C@H]5C(=O)O)c(OC)n4)c3C)c2C)ccc1CN1CC[C@H](O)C1] | MS (ESI): m/z = 699.1[M + H]⁺. ¹H NMR (400 MHz, CD₃OD) δ 8.45 (s, 2H), 7.69 (dd, J = 14.6, 8.1 Hz, 2H), 7.42 (d, J = 7.4 Hz, 2H), 7.22 (m, 2H), 7.04 (d, J = 7.5 Hz, 2H), 6.45 (m, 2H), 5.58-5.37 (m, 4H), 4.52 (s, 1H), 4.42 (s, 1H), 4.35-4.19 (m, 4H), 4.03 (m, 6H), 3.95 (m, 1H), 3.60-3.35 (m, 4H), 3.23 (m, 2H), 2.58 (s, 1H), 2.23 (s, 2H), 2.04 (m, 7H) |
| 48 | 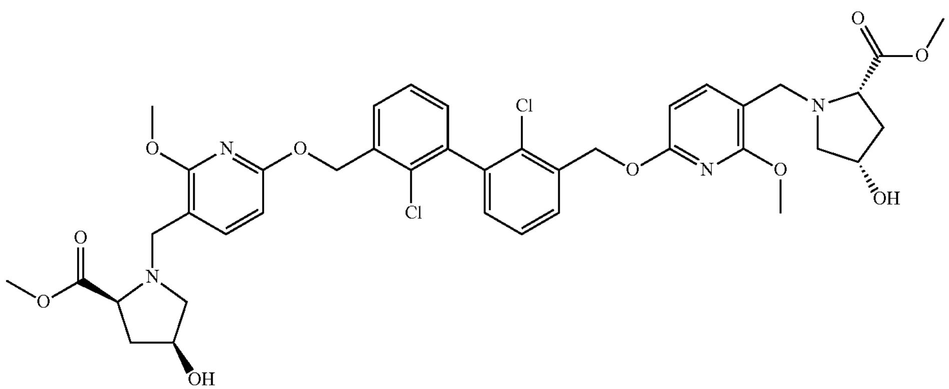 | MS (ESI): m/z = 811.0[M + H]⁺. ¹H NMR (400 MHz, CD₃OD) δ 7.58 (d, J = 8.0 Hz, 2H), 7.55 (d, J = 6.9 Hz, 2H), 7.35 (m, 2H), 7.19 (dd, J = 7.6, 1.6 Hz, 2H), 6.42 (d, J = 7.9 Hz, 2H), 5.60-5.46 (m, 4H), 4.23-4.20 (m, 2H), 3.82 (d, J = 0.4 Hz, 6H), 3.66-3.64 (m, 4H), 3.58 (d, J = 1.1 Hz, 6H), 3.18 (m, 2H), 2.94 (d, J = 10.2 Hz, 2H), 2.60-2.54 (m, 2H), 2.50-2.42 (m, 2H), 1.79-1.72 (m, 2H) |

TABLE 1-continued

| No. | Compound structure | LCMS, HNMR |
|---|---|---|
| 49 | 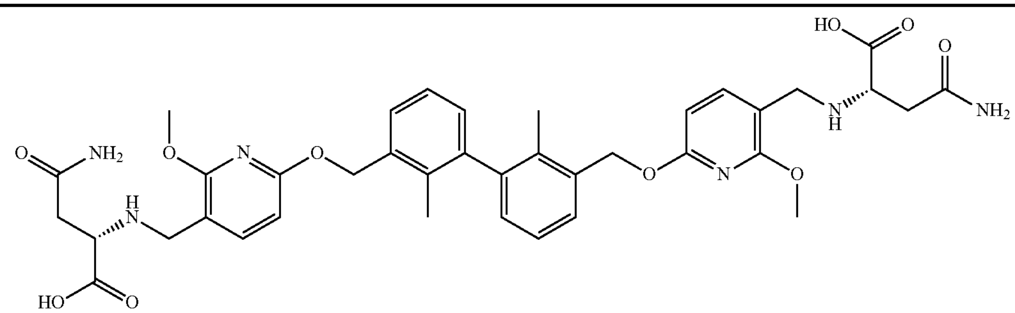 | MS (ESI): m/z = 745.0[M + H]⁺. ¹H NMR (400 MHz, DMSO-d₆) δ 8.25 (s, 1H), 7.70-7.62 (m, 4H), 7.41 (d, J = 7.6 Hz, 2H), 7.22 (m, 2H), 7.03-7.01 (m, 3H), 6.42 (d, J = 8.4 Hz, 2H), 5.34 (s, 4H), 3.85 (s, 6H), 2.58-2.55 (m, 2H), 2.40-2.32 (m, 2H), 1.96 (s, 6H) |
| 50 | 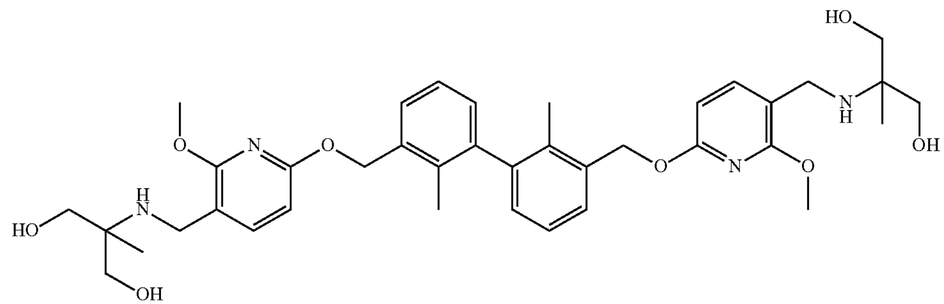 [SMILES: COc1nc(OCc2cccc(-c3cccc(COc4ccc(CNC(C)(CO)CO)c(OC)n4)c3C)c2C)ccc1CNC(C)(CO)CO] | MS (ESI): m/z = 691.1[M + H]⁺. ¹H NMR (400 MHz, DMSO-d₆) δ 7.76 (d, J = 8.0 Hz, 2H), 7.41 (d, J = 7.6 Hz, 2H), 7.20 (m, 2H), 7.02 (d, J = 7.6 Hz, 2H), 6.44 (d, J = 8.4 Hz, 2H), 5.47 (s, 4H), 4.18 (s, 4H), 4.01 (s, 6H), 3.73-3.60 (m, 8H), 2.04 (s, 6H), 1.31 (s, 6H) |
| 51 | 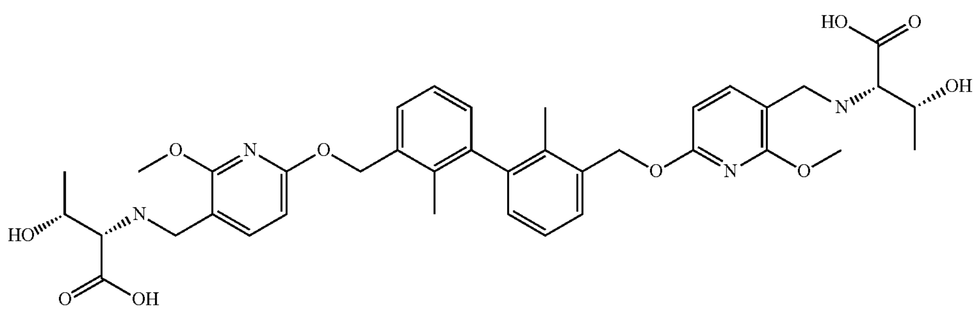 [SMILES: COc1nc(OCc2cccc(-c3cccc(COc4ccc(CN[C@H](C(=O)O)[C@@H](C)O)c(OC)n4)c3C)c2C)ccc1CN[C@H](C(=O)O)[C@@H](C)O] | MS (ESI): m/z = 719.0[M + H]⁺. ¹H NMR (400 MHz, DMSO-d₆) δ 7.70 (d, J = 8.0 Hz, 2H), 7.45 (d, J = 7.7 Hz, 2H), 7.26 (m, 2H), 7.06 (d, J = 6.7 Hz, 2H), 6.46 (d, J = 8.0 Hz, 2H), 5.42 (s, 4H), 3.89 (s, 6H), 3.86-3.83 (m, 4H), 3.76 (m, 4H), 2.92 (m, 2H), 2.00 (s, 6H), 1.12 (d, J = 6.3 Hz, 6H) |

TABLE 1-continued

| No. | Compound structure | LCMS, HNMR |
|---|---|---|
| 52 | 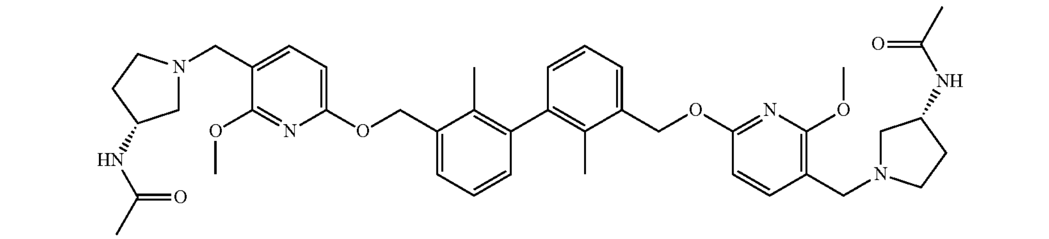 [SMILES: COc1nc(OCc2cccc(-c3cccc(COc4ccc(CN5CC[C@@H](NC(C)=O)C5)c(OC)n4)c3C)c2C)ccc1CN1CC[C@@H](NC(C)=O)C1] | MS (ESI): m/z = 369.1 [M + H]⁺. ¹H NMR (400 MHz, DMSO-d₆) δ 8.28 (s, 2H), 7.99 (d, J = 7.1 Hz, 2H), 7.60 (d, J = 8.0 Hz, 2H), 7.45 (d, J = 7.3 Hz, 2H), 7.26 (m, 2H), 7.06 (d, J = 7.3 Hz, 2H), 6.44 (d, J = 8 Hz, 2H), 5.41 (s, 4H), 4.12-4.01 (m, 2H), 3.87 (s, 6H), 3.46 (m, 4H), 2.63-2.51 (m, 4H), 2.38 (m, 2H), 2.29 (m, 2H), 2.07-1.99 (m, 2H), 2.01 (s, 6H), 1.76 (s, 6H), 1.55-1.47 (m, 2H) |
| 53 | 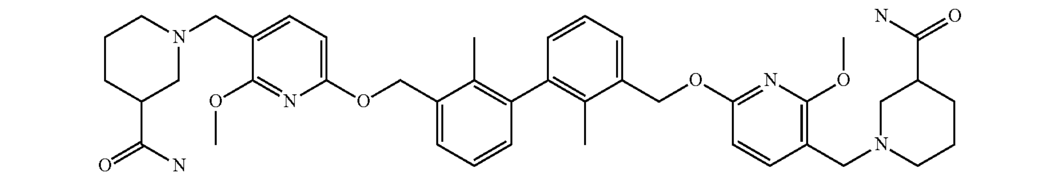 [SMILES: COc1nc(OCc2cccc(-c3cccc(COc4ccc(CN5CCCC(C(N)=O)C5)c(OC)n4)c3C)c2C)ccc1CN1CCCC(C(N)=O)C1] | MS (ESI): m/z = 369.1 [M + H]⁺. ¹H NMR (400 MHz, DMSO-d₆) δ 7.56 (d, J = 8.0 Hz, 2H), 7.45 (d, J = 7.6 Hz, 2H), 7.32 (s, 2H), 7.26 (t, J = 7.6 Hz, 2H), 7.06 (d, J = 7.5 Hz, 2H), 6.76 (s, 2H), 6.44 (d, J = 7.9 Hz, 2H), 5.41 (s, 4H), 3.86 (s, 6H), 3.37-3.28 (m, 4H), 2.67 (m, 4H), 2.32-2.25 (m, J = 10.2, 5.1 Hz, 2H), 2.09-2.03 (m, 2H), 2.01 (s, 6H), 1.95 (m, 2H), 1.74-1.52 (m, 4H), 1.48-1.25 (m, 4H) |
| 54 | 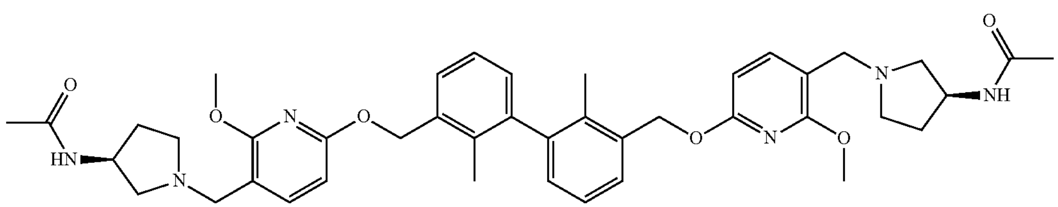 [SMILES: COc1nc(OCc2cccc(-c3cccc(COc4ccc(CN5CC[C@H](NC(C)=O)C5)c(OC)n4)c3C)c2C)ccc1CN1CC[C@H](NC(C)=O)C1] | MS (ESI): m/z = 737.1[M + H]⁺. ¹H NMR (400 MHz, CD₃OD) δ 7.54 (d, J = 8.0 Hz, 2H), 7.40 (d, J = 7.2 Hz, 2H), 7.20 (m, 2H), 7.03 (d, J = 6.8 Hz, 2H), 6.36 (d, J = 8.0 Hz, 2H), 5.42 (brs, 4H), 4.29-4.23 (m, 2H), 3.91 (s, 6H), 3.59-3.51 (m, 4H), 2.84-2.82 (m, 2H), 2.73-2.67 (m, 2H), 2.56-2.52 (m, 2H), 2.42-2.38 (m, 2H), 2.24-2.15 (m, 2H), 2.03 (s, 6H), 1.87 (s, 6H), 1.64-1.56 (m, 2H) |
| 55 | 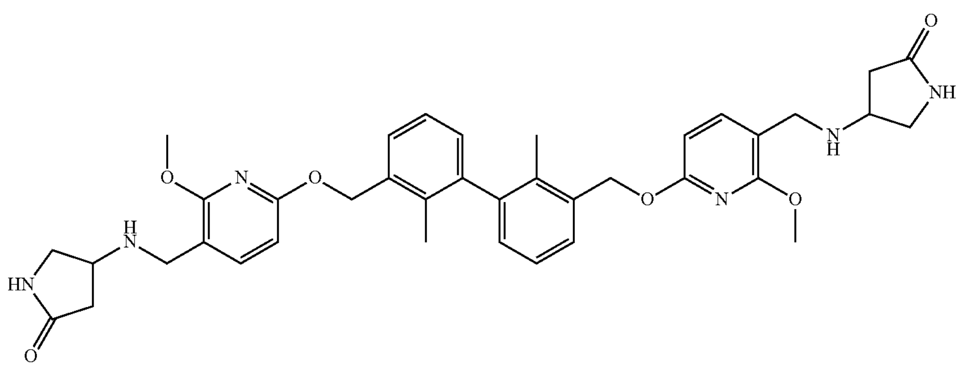 [SMILES: COc1nc(OCc2cccc(-c3cccc(COc4ccc(CNC5CNC(=O)C5)c(OC)n4)c3C)c2C)ccc1CNC1CNC(=O)C1] | MS (ESI): m/z = 681.0[M + H]⁺. ¹H NMR (400 MHz, CD₃OD) δ 7.53 (d, J = 8.0 Hz, 2H), 7.40 (d, J = 7.2 Hz, 2H), 7.19 (m, 2H), 7.02 (d, J = 7.2 Hz, 2H), 6.36 (d, J = 8.0 Hz, 2H), 5.42 (s, 4H), 3.94 (s, 6H), 3.67-3.60 (m, 4H), 3.57-3.52 (m, 4H), 3.20-3.14 (m, 2H), 2.56-2.49 (m, 2H), 2.21-2.15 (m, 2H), 2.03 (s, 6H) |

TABLE 1-continued

| No. | Compound structure | LCMS, HNMR |
|---|---|---|
| 56 | 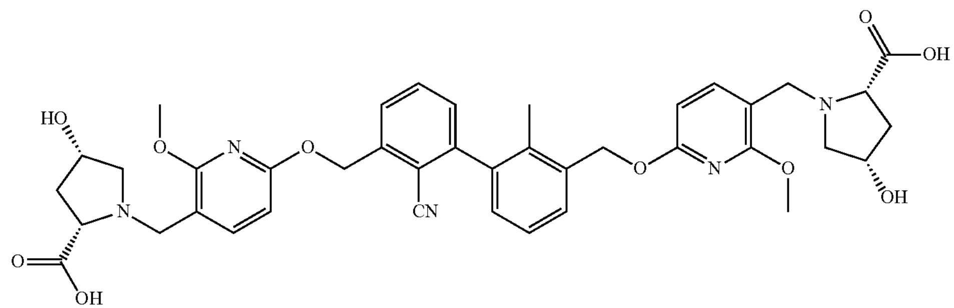 [SMILES: COc1nc(OCc2cccc(-c3cccc(COc4ccc(CN5C[C@@H](O)C[C@H]5C(=O)O)c(OC)n4)c3C#N)c2C)ccc1CN1C[C@@H](O)C[C@H]1C(=O)O] | MS (ESI): m/z = 754.0[M + H]⁺. ¹H NMR (400 MHz, CD₃OD) δ 8.37 (s, 2H), 7.70 (m, 4H), 7.52 (d, J = 7.7 Hz, 1H), 7.42-7.30 (m, 1H), 7.28 (m, 1H), 7.16 (d, J = 7.4 Hz, 1H), 6.48 (m, 2H), 5.73-5.57 (m, 2H), 5.49 (m, 2H), 4.50-4.30 (m, 4H), 4.26 (m, 2H), 4.01 (d, J = 6.2 Hz, 6H), 3.93 (m, 2H), 3.39 (m, 2H), 3.23-3.11 (m, 2H), 2.68-2.47 (m, 2H), 2.21 (m, 2H), 2.16 (s, 3H) |
| 57 | 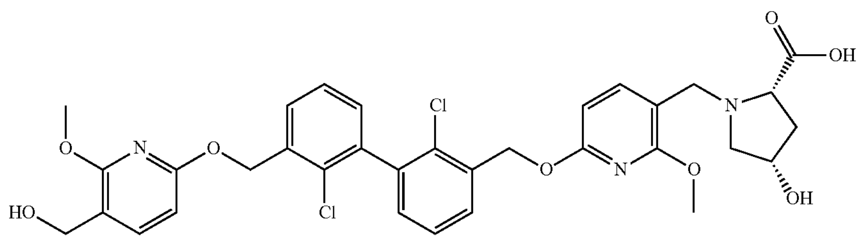 [SMILES: COc1nc(OCc2cccc(-c3cccc(COc4ccc(CN5C[C@@H](O)C[C@H]5C(=O)O)c(OC)n4)c3Cl)c2Cl)ccc1CO] | MS (ESI): m/z = 651.9[M + H]⁺. ¹H NMR (400 MHz, CD₃OD) δ 7.70 (d, J = 8.0 Hz, 1H), 7.61 (m, 1H), 7.55 (m, 2H), 7.35 (m, 2H), 7.24-7.16 (m, 2H), 6.54-6.41 (m, 2H), 5.63-5.45 (m, 4H), 4.48 (s, 2H), 4.41 (s, 1H), 4.39-4.22 (m, 2H), 4.04-3.90 (m, 4H), 3.85 (s, 3H), 3.40 (m, 1H), 3.22 (m, 1H), 2.63-2.53 (m, 1H), 2.22 (m, 1H) |
| 58 | 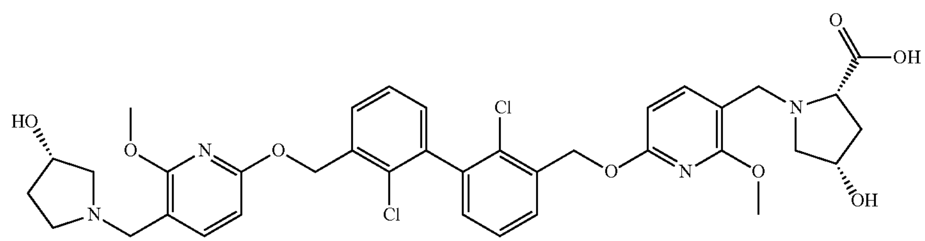 | MS (ESI): m/z = 738.9[M + H]⁺. ¹H NMR (400 MHz, CD₃OD) δ 7.72-7.67 (m, 2H), 7.56 (d, J = 7.9 Hz, 2H), 7.37 (m, 2H), 7.22 (d, J = 7.3 Hz, 2H), 6.53-6.48 (m, 2H), 5.64-5.49 (m, 4H), 4.56-4.43 (m, 2H), 4.37-4.20 (m, 3H), 4.13-4.03 (m, 2H), 3.98 (s, 3H), 3.93 (s, 3H), 3.91-3.85 (m, 1H), 3.45-3.10 (m, 4H), 3.05-2.95 (m, 1H), 2.61-2.51 (m, 1H), 2.24-2.14 (m, 2H), 1.97-1.87 (m, 1H) |
| 59 | 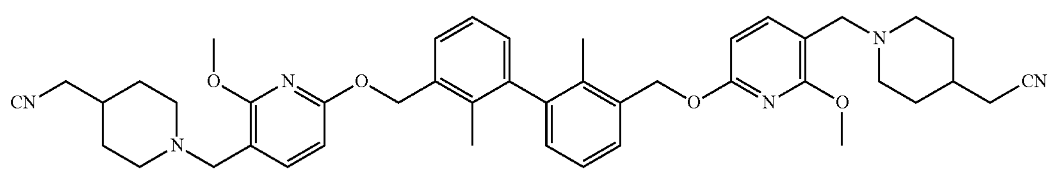 | MS (ESI): m/z = 729.1 [M + H]⁺. ¹H NMR (400 MHz, CD₃OD) δ 8.45 (s, 2H), 7.66 (d, J = 8.1 Hz, 2H), 7.42 (dd, J = 7.7, 1.4 Hz, 2H), 7.21 (m, 2H), 7.04 (dd, J = 7.6, 1.4 Hz, 2H), 6.47 (d, J = 8.1 Hz, 2H), 5.47 (s, 4H), 4.04 (s, 4H), 3.99 (s, 6H), 3.36 (m, 4H), 2.84 (m, 4H), 2.50 (m, 4H), 2.04 (s, 6H), 2.00-1.88 (m, 6H), 1.63-1.51 (m, 4H) |

TABLE 1-continued

| No. | Compound structure | LCMS, HNMR |
|---|---|---|
| 60 | 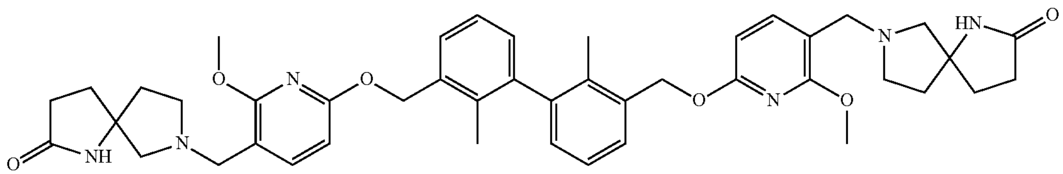 [SMILES: COc1nc(OCc2cccc(-c3cccc(COc4ccc(CN5CCC6(CCC(=O)N6)C5)c(OC)n4)c3C)c2C)ccc1CN1CCC2(CCC(=O)N2)C1] | MS (ESI): m/z = 761.1 [M + H]⁺. ¹H NMR (400 MHz, CD₃OD) δ 7.55 (d, J = 8.0 Hz, 2H), 7.41 (d, J = 7.6 Hz, 2H), 7.20 (m, 2H), 7.03 (d, J = 7.6 Hz, 2H), 6.37 (d, J = 8.0 Hz, 2H), 5.42 (s, 4H), 3.92 (s, 6H), 3.55 (s, 4H), 2.74 (m, 2H), 2.67-2.54 (m, 6H), 2.31 (m, 4H), 2.20-1.90 (m, 14H) |
| 61 | 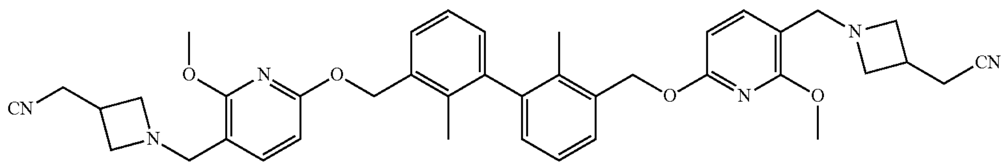 | MS (ESI): m/z = 673.0 [M + H]⁺. ¹H NMR (400 MHz, CD₃OD) δ 7.51 (d, J = 8.0 Hz, 2H), 7.39 (d, J = 7.6 Hz, 2H), 7.19 (m, 2H), 7.02 (d, J = 7.6 Hz, 2H), 6.37 (d, J = 8.0 Hz, 2H), 5.42 (s, 4H), 3.93 (s, 6H), 3.70 (s, 4H), 3.63 (m, 4H), 3.25 (m, 4H), 2.89-2.78 (m, 2H), 2.71 (m, 4H), 2.02 (s, 6H) |
| 62 | 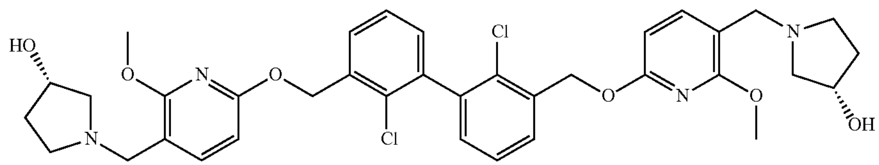 [SMILES: COc1nc(OCc2cccc(-c3cccc(COc4ccc(CN5CC[C@H](O)C5)c(OC)n4)c3Cl)c2Cl)ccc1CN1CC[C@H](O)C1] | MS (ESI): m/z = 694.9 [M + H]⁺. ¹H NMR (400 MHz, CD₃OD) δ 8.46 (s, 2H), 7.73 (d, J = 8.1 Hz, 2H), 7.57 (d, J = 6.7 Hz, 2H), 7.38 (m, 2H), 7.23 (dd, J = 7.6, 1.3 Hz, 2H), 6.55 (d, J = 8.1 Hz, 2H), 5.63-5.42 (m, 4H), 4.51 (m, 2H), 4.31-4.19 (m, 4H), 3.96 (s, 6H), 3.47 (m, 2H), 3.35 (m, 4H), 3.20 (m, 2H), 2.29-2.15 (m, 2H), 2.08-1.92 (m, 2H). |
| 63 | 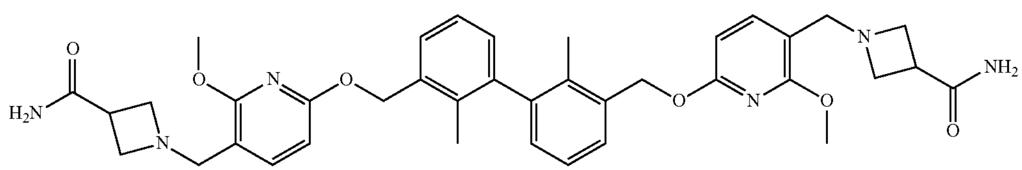 [SMILES: COc1nc(OCc2cccc(-c3cccc(COc4ccc(CN5CC(C(N)=O)C5)c(OC)n4)c3C)c2C)ccc1CN1CC(C(N)=O)C1] | MS (ESI): m/z = 681.0 [M + H]⁺. ¹H NMR (400 MHz, CD₃OD) δ 8.41 (s, 1H), 7.64 (d, J = 8.1 Hz, 2H), 7.41 (dd, J = 7.6, 1.4 Hz, 2H), 7.21 (m, 2H), 7.04 (dd, J = 7.6, 1.4 Hz, 2H), 6.44 (d, J = 8.1 Hz, 2H), 5.46 (s, 4H), 4.16 (s, 4H), 4.13-4.02 (m, 8H), 4.00 (s, 6H), 3.57-3.49 (m, 2H), 2.04 (s, 6H) |
| 64 | 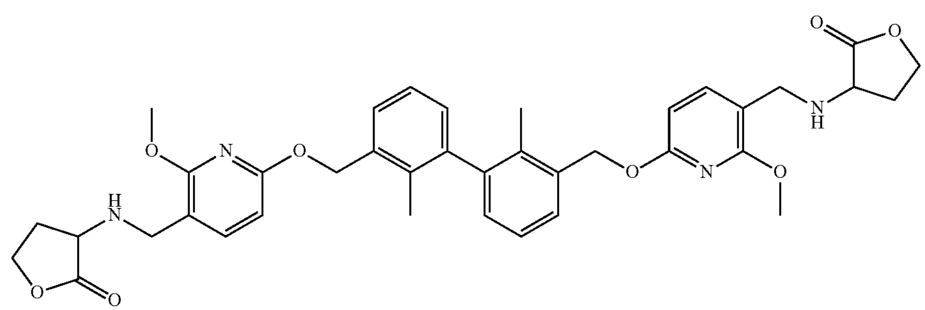 [SMILES: COc1nc(OCc2cccc(-c3cccc(COc4ccc(CNC5CCOC5=O)c(OC)n4)c3C)c2C)ccc1CNC1CCOC1=O] | MS (ESI): m/z = 704.9[M + 23]⁺. ¹H NMR (400 MHz, CD₃OD) δ 7.57 (d, J = 8.0 Hz, 2H), 7.41 (d, J = 7.5 Hz, 2H), 7.20 (m, 2H), 7.03 (d, J = 7.6 Hz, 2H), 6.39 (dd, J = 12.4, 8.1 Hz, 2H), 5.43 (brs, 4H), 4.39 (m, 2H), 4.27-4.15 (m, 2H), 3.93 (s, 6H), 3.83 (m, 4H), 3.65 (m, 2H), 2.53 (m, 2H), 2.14-2.06 (m, 2H), 2.03 (s, 6H) |

TABLE 1-continued

| No. | Compound structure | LCMS, HNMR |
|---|---|---|
| 65 | (structure) | MS (ESI): m/z = 733.1 [M + H]⁺. ¹H NMR (400 MHz, CD₃OD) δ 8.43 (s, 1H), 7.63 (d, J = 8.1 Hz, 2H), 7.41 (dd, J = 7.6, 1.4 Hz, 2H), 7.21 (m, 2H), 7.04 (dd, J = 7.6, 1.4 Hz, 2H), 6.42 (d, J = 8.0 Hz, 2H), 5.45 (s, 4H), 4.12-4.05 (m, 2H), 3.96 (s, 5H), 3.88 (s, 3H), 3.33-3.30 (m, 2H), 3.13 (dd, J = 11.1, 6.3 Hz, 2H), 2.88 (m, 2H), 2.73-2.57 (m, 6H), 2.44-2.34 (m, 2H), 2.04 (s, 6H) |
| 66 | (structure) | MS (ESI): m/z = 747.0 [M + H]⁺. ¹H NMR (400 MHz, DMSO-d₆) δ 7.68 (d, J = 8.0 Hz, 2H), 7.60-7.56 (m, 1H), 7.51 (d, J = 7.1 Hz, 1H), 7.34-7.26 (m, 3H), 7.20 (d, J = 6.9 Hz, 1H), 6.46 (d, J = 8.0 Hz, 2H), 5.47 (s, 2H), 5.43 (s, 2H), 4.19 (d, J = 2.5 Hz, 2H), 3.91 (s, 4H), 3.87 (s, 4H), 3.75 (d, J = 8 Hz, 1H), 3.72 (d, J = 8 Hz, 1H), 3.39-3.33 (m, 2H), 2.99-2.88 (m, 2H), 2.74-2.63 (m, 2H), 2.38-2.28 (m, 2H), 2.14 (s, 3H), 1.87-1.77 (m, 2H). |
| 67 | (structure) | MS (ESI): m/z = 719.0 [M + H]⁺. ¹H NMR (400 MHz, CD₃OD) δ 7.63 (d, J = 8.1 Hz, 2H), 7.41 (d, J = 7.2 Hz, 2H), 7.21 (m, 2H), 7.03 (d, J = 6.9 Hz, 2H), 6.43 (d, J = 8.0 Hz, 2H), 5.46 (brs, 4H), 4.13 (m, 4H), 4.00 (s, 6H), 3.87-3.67 (m, 4H), 3.60 (m, 2H), 2.19-2.05 (m, 2H), 2.3 (s, 6H), 2.01-1.88 (m, 2H) |

TABLE 1-continued

| No. | Compound structure | LCMS, HNMR |
|---|---|---|
| 68 | 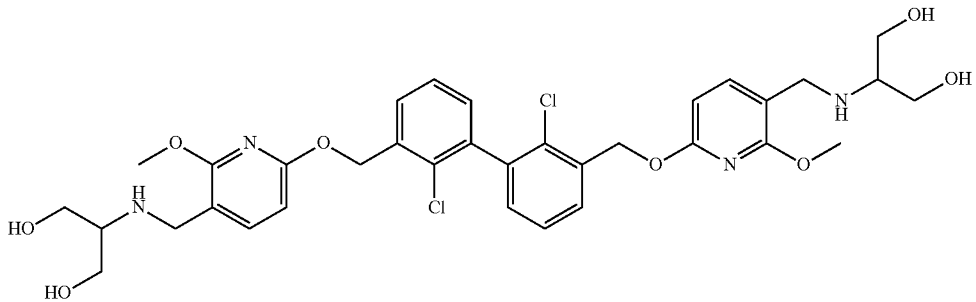 [SMILES: COc1nc(OCc2cccc(-c3cccc(COc4ccc(CNC(CO)CO)c(OC)n4)c3Cl)c2Cl)ccc1CNC(CO)CO] | MS (ESI): m/z = 703.6 [M + H]$^+$. $^1$H NMR (400 MHz, DMSO-d$_6$) δ 8.23 (d, J = 8.1 Hz, 2H), 7.70 (dd, J = 7.9, 2.7 Hz, 2H), 7.62 7.62 (d, J = 7.7 Hz, 2H), 7.46 (m, 2H), 7.31 (d, J = 7.4 Hz, 2H), 6.49 (dd, J = 7.9, 1.3 Hz, 2H), 5.51 (m, 4H), 3.83 (s, 6H), 3.68 (m, 4H), 3.46-3.31 (m, 8H), 2.59-2.53 (m, 2H), 2.14 (m, 1H) |
| 69 | 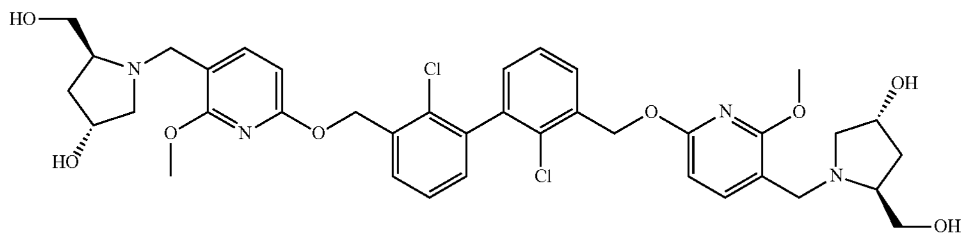 [SMILES: COc1nc(OCc2cccc(-c3cccc(COc4ccc(CN5C[C@H](O)C[C@H]5CO)c(OC)n4)c3Cl)c2Cl)ccc1CN1C[C@H](O)C[C@H]1CO] | MS (ESI): m/z = 378.0 [M + H]$^+$. $^1$H NMR (400 MHz, DMSO-d$_6$) δ 8.17 (s, 1H), 7.62 (m, 4H), 7.45 (m, 2H), 7.31 (d, J = 6.3 Hz, 2H), 6.48 (d, J = 7.9 Hz, 2H), 5.49 (dd, J = 12.1, 6.7 Hz, 4H), 4.11-4.03 (m, 2H), 3.86 (s, 2H), 3.81 (s, 6H), 3.43 (m, 4H), 3.29 (m, 2H), 3.02 (m, 2H), 2.85-2.80 (m, 2H), 2.14 (m, 2H), 1.78-1.64 (m, 4H) |
| 70 | 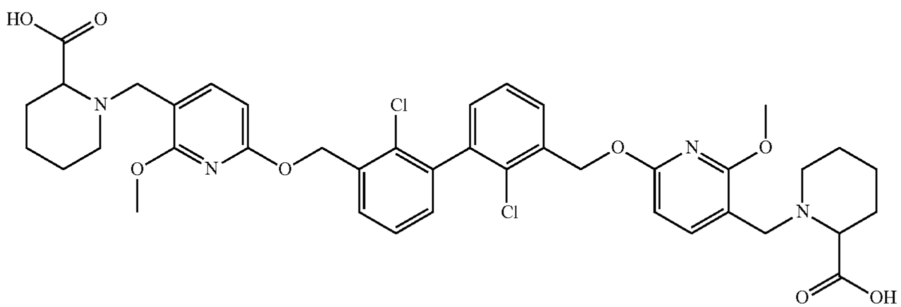 [SMILES: COc1nc(OCc2cccc(-c3cccc(COc4ccc(CN5CCCCC5C(=O)O)c(OC)n4)c3Cl)c2Cl)ccc1CN1CCCCC1C(=O)O] | MS (ESI): m/z = 778.9 [M + H]$^+$. $^1$H NMR (400 MHz, DMSO-d$_6$) δ 7.70 (d, J = 8.0 Hz, 2H), 7.62 (d, J = 7.9 Hz, 2H), 7.46 (m, 2H), 7.32 (d, J = 7.5 Hz, 2H), 6.53 (d, J = 8.0 Hz, 2H), 5.50 (m, 4H), 3.81 (s, 6H), 3.66 (m, 4H), 3.12-3.09 (m, 2H), 2.97-2.84 (m, 2H), 2.32-2.26 (m, 2H), 1.79 (s, 2H), 1.73-1.64 (m, 2H), 1.50 (s, 6H), 1.39-1.35 (m, 2H) |
| 71 | 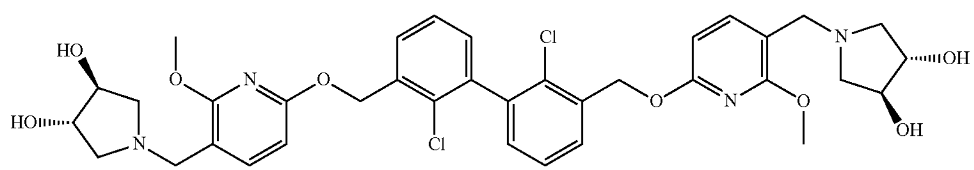 [SMILES: COc1nc(OCc2cccc(-c3cccc(COc4ccc(CN5C[C@H](O)[C@@H](O)C5)c(OC)n4)c3Cl)c2Cl)ccc1CN1C[C@H](O)[C@@H](O)C1] | MS (ESI): m/z = 726.9 [M + H]$^+$. $^1$H NMR (400 MHz, CD$_3$OD) δ 8.49 (s, 2H), 7.72 (d, J = 8.1 Hz, 2H), 7.57 (d, J = 7.7 Hz, 2H), 7.37 (m, 2H), 7.22 (d, J = 7.6, 1.5 Hz, 2H), 6.53 (d, J = 8.1 Hz, 2H), 5.57 (brs, 4H), 4.18 (m, 8H), 3.94 (s, 6H), 3.49 (m, 4H), 3.15 (m, 4H) |

TABLE 1-continued

| No. | Compound structure | LCMS, HNMR |
|---|---|---|
| 72 | 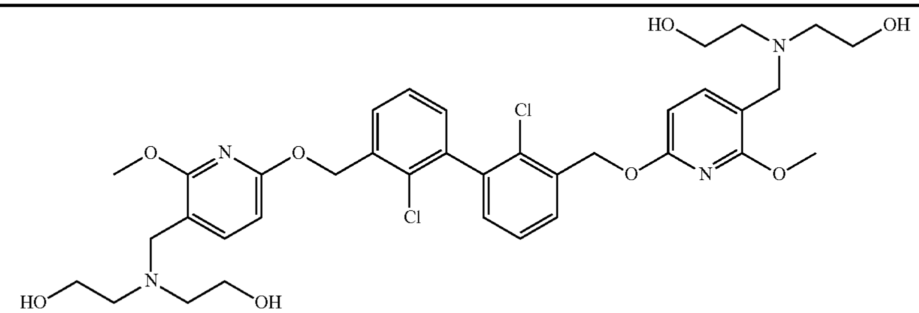 | MS (ESI): m/z = 730.9 [M + H]⁺. ¹H NMR (400 MHz, CD₃OD) δ 7.66 (d, J = 8.0 Hz, 2H), 7.55 (dd, J = 7.7, 1.7 Hz, 2H), 7.36 (m, 2H), 7.20 (dd, J = 7.6, 1.7 Hz, 2H), 6.45 (d, J = 8.0 Hz, 2H), 5.58-5.48 (m, 4H), 3.86 (s, 6H), 3.74 (s, 4H), 3.64 (m, 8H), 2.82-2.69 (m, 8H) |
| 73 | 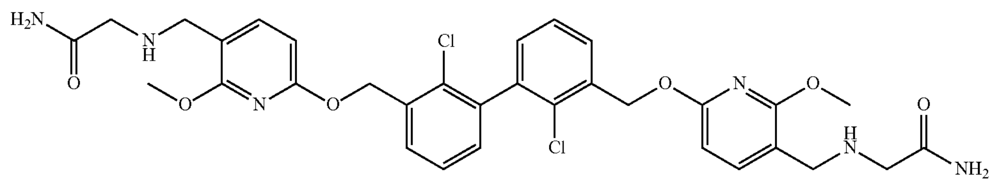 [SMILES: COc1nc(OCc2cccc(-c3cccc(COc4ccc(CNCC(N)=O)c(OC)n4)c3Cl)c2Cl)ccc1CNCC(N)=O] | MS (ESI): m/z = 668.9 [M + H]⁺. ¹H NMR (400 MHz, DMSO-d₆) δ 7.66 (d, J = 7.9 Hz, 2H), 7.61 (dd, J = 7.7, 1.5 Hz, 2H), 7.45 (m, 2H), 7.31 (dd, J = 7.6, 1.5 Hz, 2H), 7.07 (s, 2H), 6.48 (d, J = 7.9 Hz, 2H), 5.50 (m, 4H), 3.82 (s, 6H), 3.54 (s, 4H), 3.02 (m, 4H) |
| 74 | 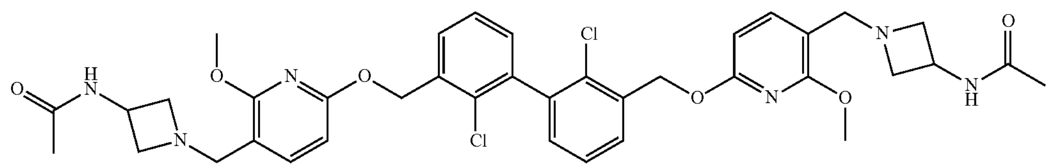 [SMILES: COc1nc(OCc2cccc(-c3cccc(COc4ccc(CN5CC(NC(C)=O)C5)c(OC)n4)c3Cl)c2Cl)ccc1CN1CC(NC(C)=O)C1] | MS (ESI): m/z = 748.9 [M + H]⁺. ¹H NMR (400 MHz, CD₃OD) δ 8.47 (s, 2H), 7.63 (d, J = 8.0 Hz, 2H), 7.55 (dd, J = 7.7, 1.6 Hz, 2H), 7.36 (m, 2H), 7.21 (dd, J = 7.6, 1.7 Hz, 2H), 6.49 (d, J = 8.0 Hz, 2H), 5.55 (m, 4H), 4.50-4.41 (m, 2H), 4.07-3.97 (m, 8H), 3.91 (s, 6H), 3.71 (m, 4H), 1.93 (s, 6H) |
| 75 | 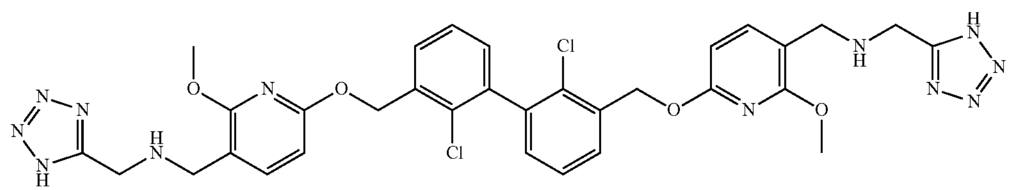 [SMILES: COc1nc(OCc2cccc(-c3cccc(COc4ccc(CNCc5nnn[nH]5)c(OC)n4)c3Cl)c2Cl)ccc1CNCc1nnn[nH]1] | MS (ESI): m/z = 718.9 [M + H]⁺. ¹H NMR (400 MHz, DMSO-d₆) δ 7.73 (d, J = 8.0 Hz, 2H), 7.58 (d, J = 7.6 Hz, 2H), 7.42 (m, 2H), 7.28 (d, J = 7.2 Hz, 2H), 6.52 (d, J = 8.4 Hz, 2H), 5.54-5.45 (m, 4H), 4.12 (s, 4H), 3.94 (s, 4H), 3.82 (s, 6H) |
| 76 | 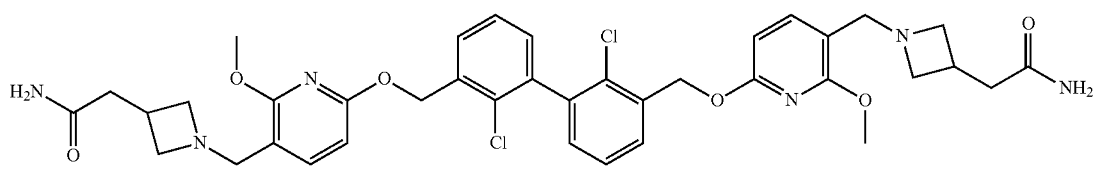 [SMILES: COc1nc(OCc2cccc(-c3cccc(COc4ccc(CN5CC(CC(N)=O)C5)c(OC)n4)c3Cl)c2Cl)ccc1CN1CC(CC(N)=O)C1] | MS (ESI): m/z = 748.9 [M + H]⁺. ¹H NMR (400 MHz, CD₃OD) δ 7.61 (d, J = 8.0 Hz, 2H), 7.55 (d, J = 6.2 Hz, 2H), 7.36 (m, 2H), 7.21 (dd, J = 7.6, 1.6 Hz, 2H), 6.48 (d, J = 8.0 Hz, 2H), 5.55 (brs, 4H), 3.94 (m, 4H), 3.91 (s, 6H), 3.87 (m, 4H), 3.60-3.50 (m, 4H), 3.05-2.89 (m, 2H), 2.52 (m, 5H) |

TABLE 1-continued

| No. | Compound structure | LCMS, HNMR |
|---|---|---|
| 77 | 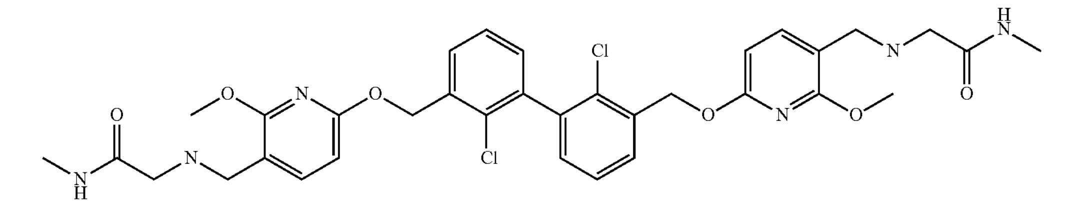 | MS-ESI: m/z 696.9[M + H]⁺. ¹H NMR (400 MHz, DMSO-d₆) δ 7.74 (d, J = 4.8 Hz, 2H), 7.63 (d, J = 7.9 Hz, 2H), 7.57 (dd, J = 7.7, 1.4 Hz, 2H), 7.41 (m, 2H), 7.27 (dd, J = 7.6, 1.6 Hz, 2H), 6.45 (d, J = 7.9 Hz, 2H), 5.46 (m, 4H), 3.79 (s, 6H), 3.49 (s, 4H), 3.00 (brs, 4H), 2.56 (d, J = 4.7 Hz, 6H) |
| 78 | 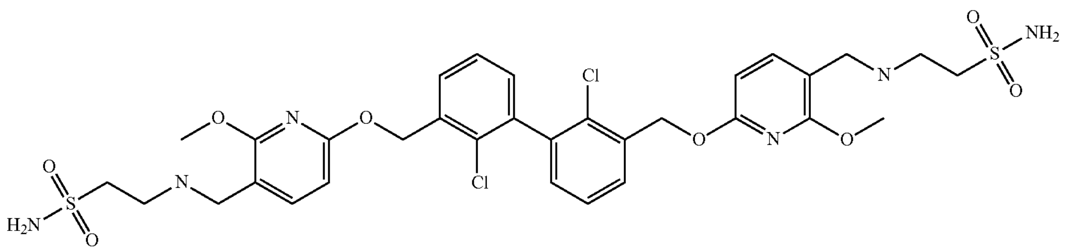 [SMILES: COc1nc(OCc2cccc(-c3cccc(COc4ccc(CNCCS(N)(=O)=O)c(OC)n4)c3Cl)c2Cl)ccc1CNCCS(N)(=O)=O] | MS-ESI: m/z 769.0[M + H]⁺. ¹H NMR (400 MHz, DMSO-d₆) δ 7.62 (d, J = 8.0 Hz, 2H), 7.57 (dd, J = 1.2, 7.6 Hz, 2H), 7.41 (m, 2H), 7.27 (dd, J = 1.2, 7.6 Hz, 2H), 6.78 (s, 3H), 6.46 (d, J = 7.6 Hz, 1H), 5.47 (m, 2H), 3.79 (s, 6H), 3.57 (s, 3H), 3.10 (m, 4H), 2.85 (m, 4H), 1.18-1.08 (m, 4H) |
| 79 | 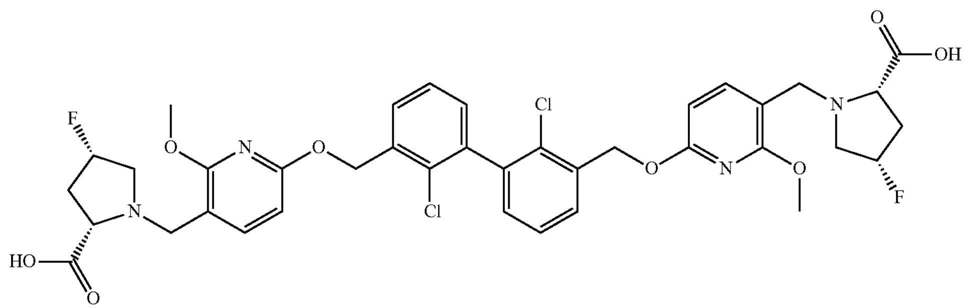 [SMILES: COc1nc(OCc2cccc(-c3cccc(COc4ccc(CN5C[C@@H](F)C[C@H]5C(=O)O)c(OC)n4)c3Cl)c2Cl)ccc1CN1C[C@@H](F)C[C@H]1C(=O)O] | MS (ESI): m/z = 786.9 [M + H]⁺. ¹H NMR (400 MHz, CD₃OD) δ 7.73 (m, 2H), 7.57 (d, J = 7.7 Hz, 2H), 7.38 (m, 2H), 7.22 (dd, J = 7.6, 1.5 Hz, 2H), 6.56-6.46 (m, 2H), 5.57 (m, 4H), 5.36 (d, J = 3.6 Hz, 1H), 5.23 (d, J = 3.4 Hz, 1H), 4.43-4.27 (m, 4H), 4.08-3.93 (m, 8H), 3.92-3.76 (m, 2H), 3.44 (m, 1H), 3.35 (m, 1H), 2.82-2.60 (m, 2H), 2.55-2.40 (m, 2H) |
| 80 | 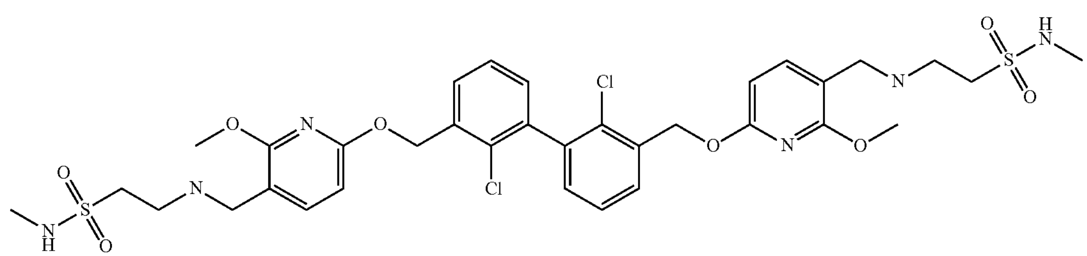 | MS (ESI): m/z = 796.8 [M + H]⁺. ¹H NMR (400 MHz, DMSO-d₆) δ 8.37 (s, 2H), 7.66-7.58 (m, 4H), 7.45 (m, 2H), 7.30 (dd, J = 7.6, 1.6 Hz, 2H), 6.86 (s, 2H), 6.49 (d, J = 7.9 Hz, 2H), 5.50 (m, 4H), 3.82 (s, 6H), 3.57 (brs, 4H), 3.14 (m, 4H), 2.80 (m, 4H), 2.55 (m, 4H) |

TABLE 1-continued

| No. | Compound structure | LCMS, HNMR |
|---|---|---|
| 81 | 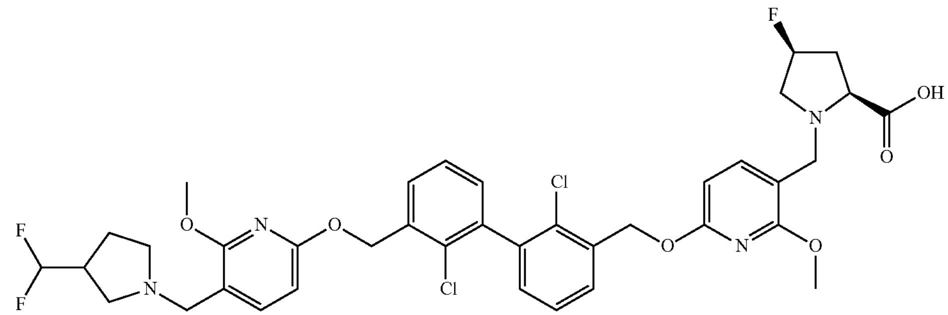 [SMILES: COc1nc(OCc2cccc(-c3cccc(COc4ccc(CN5C[C@@H](F)C[C@H]5C(=O)O)c(OC)n4)c3Cl)c2Cl)ccc1CN1CCC(C(F)F)C1] | MS (ESI): m/z = 775.2 [M + H]⁺. ¹H NMR (400 MHz, DMSO-d₆) δ 7.68-7.61 (m, 4H), 7.45 (m, 2H), 7.31 (d, J = 7.7 Hz, 2H), 6.50 (m, 2H), 6.11-5.81 (m, 2H), 5.50 (m, 4H), 5.19 (s, 1H), 5.05 (s, 1H), 3.90-3.78 (m, 6H), 3.61-3.41 (m, 4H), 3.20-3.01 (m, 3H), 2.63-2.53 (m, 2H), 2.49-2.39 (m, 1H), 2.09-1.84 (m, 3H), 1.67-1.62 (m, 1H) |
| 82 | 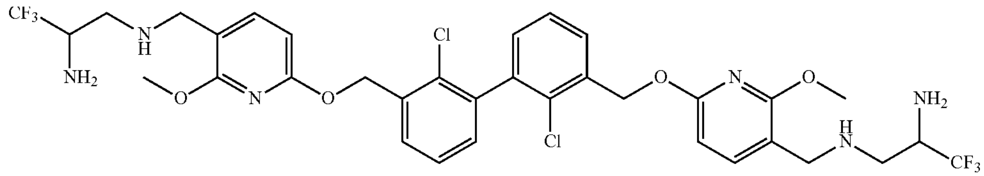 [SMILES: COc1nc(OCc2cccc(-c3cccc(COc4ccc(CNCC(N)C(F)(F)F)c(OC)n4)c3Cl)c2Cl)ccc1CNCC(N)C(F)(F)F] | MS (ESI): m/z = 777.2 [M + H]⁺. ¹H NMR (400 MHz, DMSO-d₆) δ 7.22-1.64 (m, 2H), 7.61 (d, J = 7.4 Hz, 2H), 7.45 (m, 2H), 7.30 (d, J = 8 Hz, 2H), 6.49 (dd, J = 7.9, 1.8 Hz, 2H), 5.50 (m, 4H), 3.86-3.79 (m, 6H), 3.71 (s, 2H), 3.59 (m, 4H), 3.07 (s, 2H), 2.83 (m, 1H), 2.68 (m, 2H), 2.57 (m, 1H) |

Test Example 1 Effect of the Compound of the Invention on PD-L1 Activity at the Molecular Level PD-1/PD-L1 homogeneous time-resolved fluorescence (HTRF) detection technology was used to detect the binding ability of the compound to PD-L1.

PD1/PD-L1 binding assay kit (Cisbio, Cat #63ADK000CPDEC) was used, which includes two proteins, Tag 1-PD-L1 and Tag 2-PD-1, and two antibodies, Anti-Tag1-Eu$^{3+}$ and Anti-Tag2-XL 665. Assay principle: Anti-tag1-Eu$^{3+}$ is the HTRF donor, and Anti-Tag2-XL 665 is the HTRF acceptor. When Tag 1-PD-L1 and Tag 2-PD-1 interact, the added HTRF donor and the acceptor are close to each other. After the donor receives the excitation energy, it transfers part of the energy to the acceptor, thus producing 665 nm emission signal. When the compound is added to block the PD1/PD-L1 interaction, only 620 nm emission light was detected. The inhibitory effect of the compound was determined by analyzing the ratio of 665 nm/620 nm. Tag 1-PD-L1 was diluted with Diluent buffer (cat #62DLBDDF) to a working concentration of 10 nM, Tag 2-PD-1 was diluted with Diluent buffer to a working concentration of 500 nM, and Anti-Tag1-Eu$^{3+}$ was diluted with detection buffer (cat #62DB1FDG) by 1:100, Anti-Tag2-XL 665 was diluted with detection buffer by 1:20, and the test compound was diluted with Diluent buffer to a final concentration of 2×. In a 384-well plate, 2 μL of compound was added to each well, and then 4 μL of Tag 1-PD-L1, 4 μL of Tag 2-PD-1 were added and incubated at room temperature for 15 minutes. 5 μL Anti-Tag1-Eu$^{3+}$ and 5 μL Anti-Tag2-XL 665 were added and incubated overnight at room temperature, and detected with BioTek Synergy™ Neo2 Multifunctional Microplate Reader to obtain the ratio of 665 nm/620 nm. The IC50 curve was fitted by GraphPad Prism 5.02.

TABLE 1

IC$_{50}$ values of some compounds of the present invention

| Compound no. | PD-L1 IC$_{50}$ (nM) |
| --- | --- |
| 1 | D |
| 2 | D |
| 3 | D |
| 5 | D |
| 6 | B |
| 7 | D |
| 8 | D |
| 9 | A |
| 10 | D |
| 11 | D |
| 12 | D |
| 13 | D |
| 15 | C |
| 16 | D |
| 17 | D |
| 18 | D |
| 19 | C |
| 20 | B |
| 22 | B |
| 23 | C |
| 24 | B |
| 25 | D |
| 26 | A |
| 27 | A |
| 28 | B |
| 29 | D |
| 30 | A |
| 31 | D |
| 32 | D |
| 33 | B |
| 34 | B |
| 35 | A |
| 36 | A |
| 37 | A |
| 38 | D |
| 39 | B |
| 40 | D |
| 41 | B |
| 42 | A |
| 43 | A |
| 44 | D |
| 45 | A |
| 46 | A |
| 47 | A |
| 48 | C |
| 49 | A |
| 50 | A |
| 51 | A |
| 52 | B |
| 53 | C |
| 54 | B |
| 55 | B |
| 56 | A |
| 57 | B |
| 58 | A |
| 59 | B |
| 60 | A |
| 61 | B |
| 62 | A |
| 63 | A |
| 64 | B |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | B |
| 81 | A |
| 82 | B |

The letter A represents IC$_{50}$ less than 10 nM;
The letter B represents IC$_{50}$ from 10 nM to 100 nM;
The letter C represents IC$_{50}$ from 100 nM to 1 μM;
The letter D represents IC$_{50}$ greater than 1 μM.

The results showed that the compounds of the present invention could effectively inhibit the binding of PD-1/PD-L1 at different concentrations. Therefore, the compounds of the present invention can be used in the treatment of diseases related to the mutual binding of PD-1/PD-L1.

Test Example 2 Effect of the Compound of the Invention on PD-L1 Activity at the Cellular Level Two types of cells were used in the cytology experiments of PD1/PD-L1, PD-1 effector cells and PD-L1 aAPC cells, wherein PD-1 effector cells express human PD-1 protein, TCR and luciferase reporter gene driven by NFAT-RE, PD-L1 aAPC cells express PD-L1 protein and engineered cell surface protein, which can activate TCR independently of specific antigens. When these two cells were co-cultured, the PD-1/PD-L1 interaction could inhibit the signal transmission from TCR to NFAT-RE and interrupt the NFAT-REmediated fluorescent signal. When an inhibitor of PD-1 or PD-L1 was added, the PD-1/PD-L1 interaction was blocked, and the signal inhibition of the TCR to NFAT-RE pathway was removed, and the fluorescence signal was enhanced. The blocking effect of the inhibitors was assayed according to the strength of fluorescence signal.

On the first day of the experiment, the recovered PD-L1 aAPC cells were digested. After centrifugation, the concentration was diluted to $2.5*10^5$/mL with medium (90% Ham's F-12/10% FBS). 40 µL cells ($1*10^4$) were plated in each well of 384-well plates and cultured overnight in an incubator. On the second day, the test compound was diluted with assay buffer (99% RPMI1640/1% FBS) to 2* of final concentration. PD-1 cells were centrifuged and diluted to a concentration of $6.25*10^5$/mL with detection buffer. Remove the culture medium from the overnight cultured 384-well plate. Transfer 20 µL of the diluted compound and 20 µL of PD-1 cells to each well. After incubated in the cell incubator for 6 hours, 20 µL of Bio-Glo reagent was added to each well (Promega, cat #G7940). After 10 minutes, the fluorescence signal was read by a multi-functional microplate reader. Negative control (only cells and no compounds) and a blank control (only detection buffers) were set for each plate. Based on the fluorescence value, Prism5 was used to analyze the inhibitory activity of each compound.

The results showed that the compounds of the present invention exhibited inhibitory activity on PD-1 cells at the cellular level, and the inhibitory activity was equivalent to or better than known PD-1 inhibitors in the art.

All literatures cited in the present application are incorporated herein as reference, the same as individually cited ones. Additionally, it should be understood that after reading the above teachings, those skilled in the art can make various changes and modifications to the present invention. These equivalents shall also fall within the scope defined by the appended claims.

The invention claimed is:

1. A compound selected from the following group, or a stereoisomer, a racemate, or a pharmaceutically acceptable salt thereof,

| No. | Structure of compound |
|---|---|
| 6 |  |
| 9 |  |
| 17 |  |
| 20 |  |

| No. | Structure of compound |
|---|---|
| 22 | 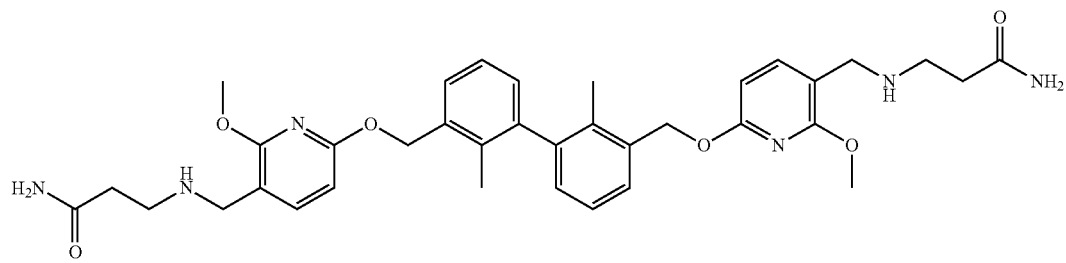 [SMILES: COc1nc(OCc2cccc(-c3cccc(COc4ccc(CNCCC(N)=O)c(OC)n4)c3C)c2C)ccc1CNCCC(N)=O] |
| 24 | 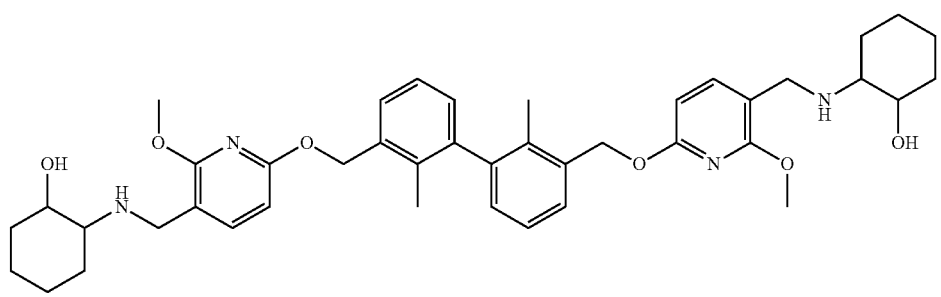 [SMILES: COc1nc(OCc2cccc(-c3cccc(COc4ccc(CNC5CCCCC5O)c(OC)n4)c3C)c2C)ccc1CNC1CCCCC1O] |
| 26 | 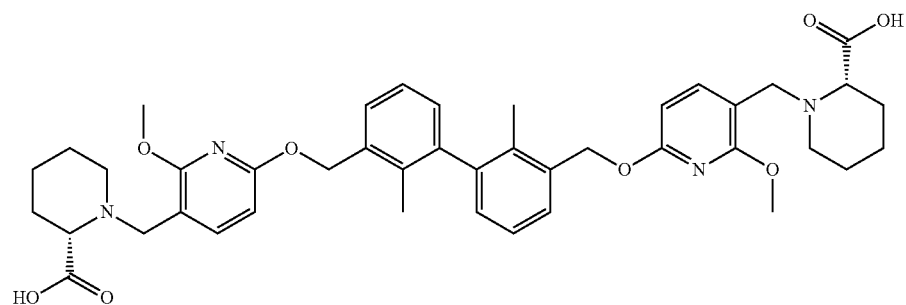 |
| 27 | 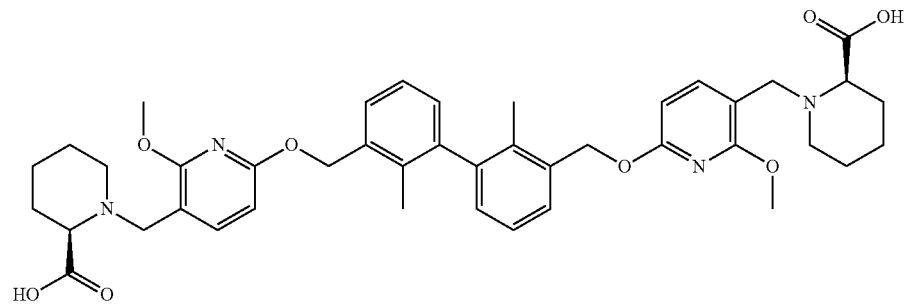 [SMILES: COc1nc(OCc2cccc(-c3cccc(COc4ccc(CN5CCCC[C@@H]5C(=O)O)c(OC)n4)c3C)c2C)ccc1CN1CCCC[C@@H]1C(=O)O] |
| 28 | 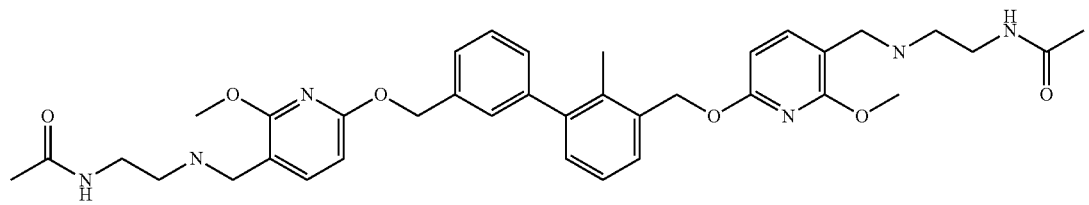 [SMILES: COc1nc(OCc2cccc(-c3cccc(COc4ccc(CNCCNC(C)=O)c(OC)n4)c3C)c2)ccc1CNCCNC(C)=O] |

| No. | Structure of compound |
|---|---|
| 30 | |
| 33 | |
| 35 | |
| 37 | |
| 39 | |
| 41 | |

-continued
| No. | Structure of compound |
|---|---|
| 42 | 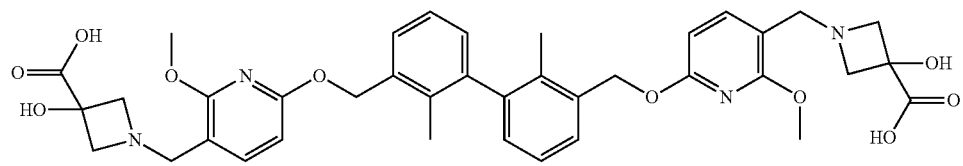 [SMILES: COc1nc(OCc2cccc(-c3cccc(COc4ccc(CN5CC(O)(C(=O)O)C5)c(OC)n4)c3C)c2C)ccc1CN1CC(O)(C(=O)O)C1] |
| 43 | 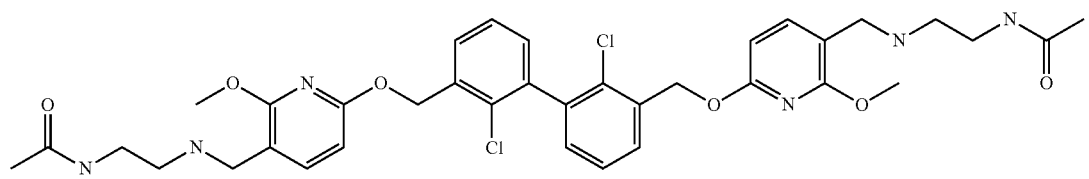 [SMILES: COc1nc(OCc2cccc(-c3cccc(COc4ccc(CNCCNC(C)=O)c(OC)n4)c3Cl)c2Cl)ccc1CNCCNC(C)=O] |
| 46 | 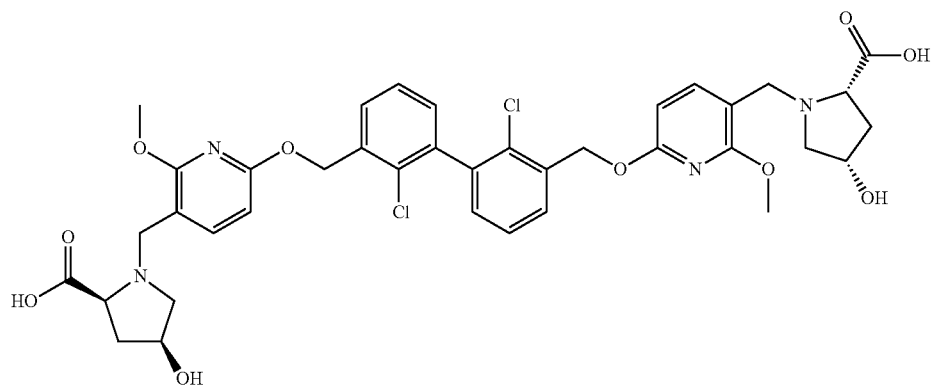 [SMILES: COc1nc(OCc2cccc(-c3cccc(COc4ccc(CN5C[C@@H](O)C[C@H]5C(=O)O)c(OC)n4)c3Cl)c2Cl)ccc1CN1C[C@@H](O)C[C@H]1C(=O)O] |
| 47 | 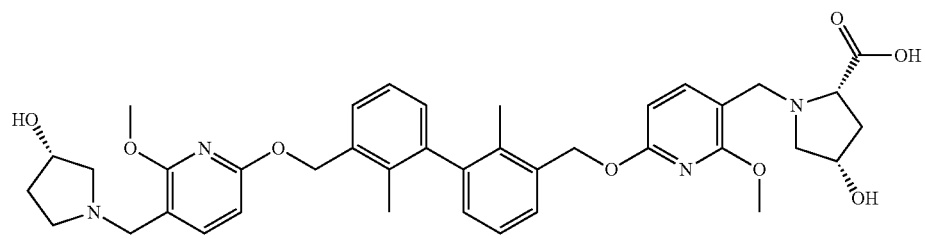 [SMILES: COc1nc(OCc2cccc(-c3cccc(COc4ccc(CN5C[C@@H](O)C[C@H]5C(=O)O)c(OC)n4)c3C)c2C)ccc1CN1CC[C@H](O)C1] |
| 48 | 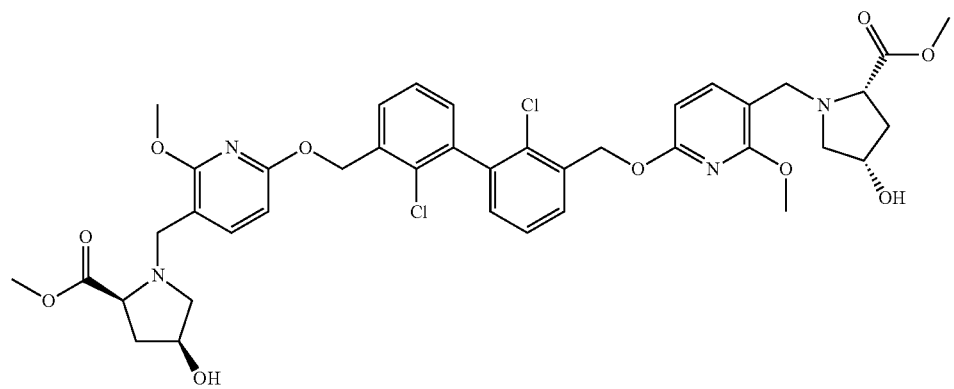 |

-continued
| No. | Structure of compound |
|---|---|
| 49 | 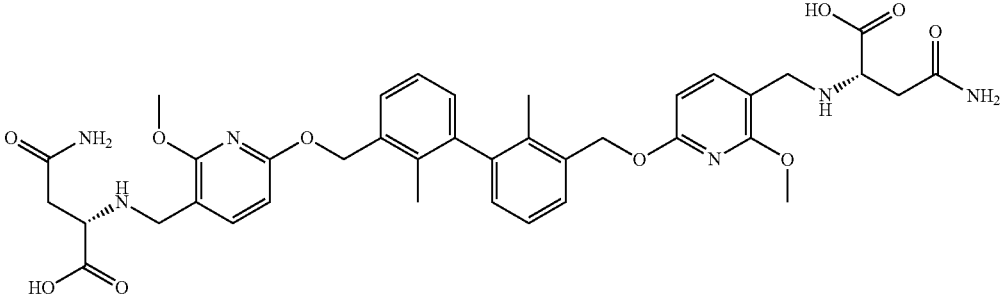 [SMILES: COc1nc(OCc2cccc(-c3cccc(COc4ccc(CN[C@@H](CC(N)=O)C(=O)O)c(OC)n4)c3C)c2C)ccc1CN[C@@H](CC(N)=O)C(=O)O] |
| 50 | 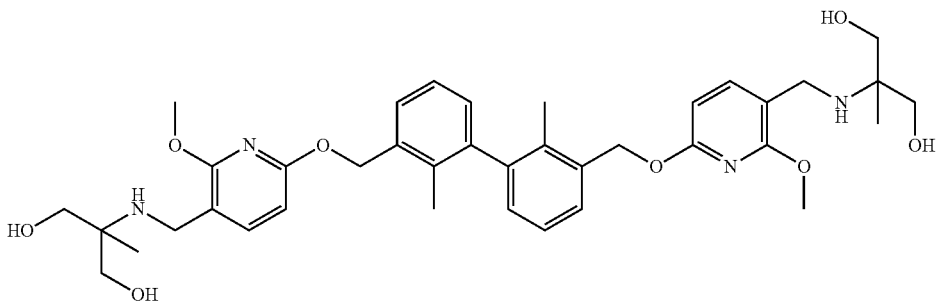 [SMILES: COc1nc(OCc2cccc(-c3cccc(COc4ccc(CNC(C)(CO)CO)c(OC)n4)c3C)c2C)ccc1CNC(C)(CO)CO] |
| 51 | 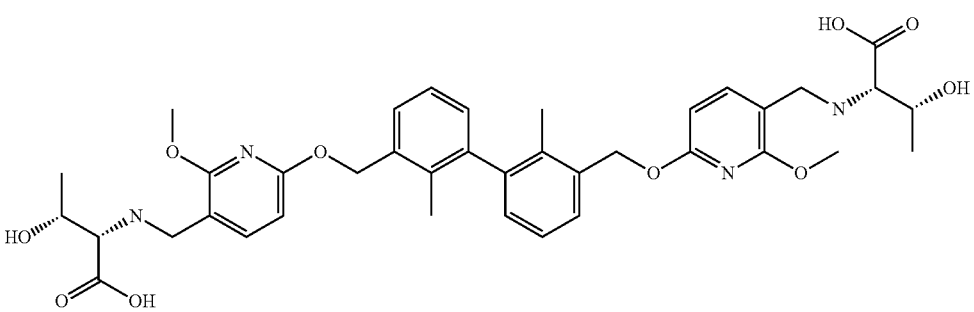 [SMILES: COc1nc(OCc2cccc(-c3cccc(COc4ccc(CN[C@H](C(=O)O)[C@@H](C)O)c(OC)n4)c3C)c2C)ccc1CN[C@H](C(=O)O)[C@@H](C)O] |
| 52 | 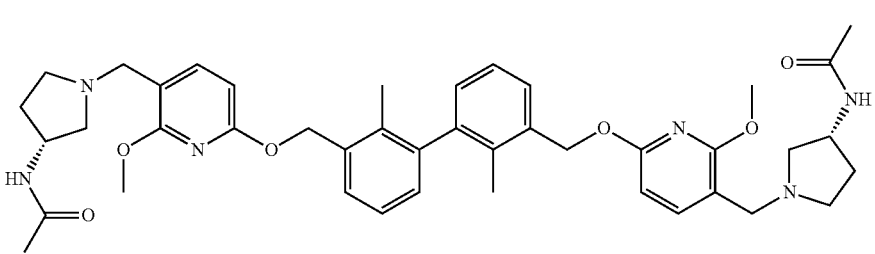 [SMILES: COc1nc(OCc2cccc(-c3cccc(COc4ccc(CN5CC[C@@H](NC(C)=O)C5)c(OC)n4)c3C)c2C)ccc1CN1CC[C@@H](NC(C)=O)C1] |
| 53 | 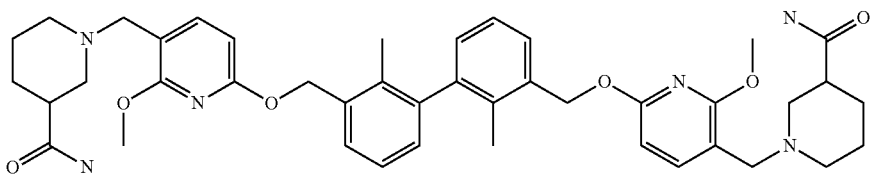 [SMILES: COc1nc(OCc2cccc(-c3cccc(COc4ccc(CN5CCCC(C(N)=O)C5)c(OC)n4)c3C)c2C)ccc1CN1CCCC(C(N)=O)C1] |
| 54 | 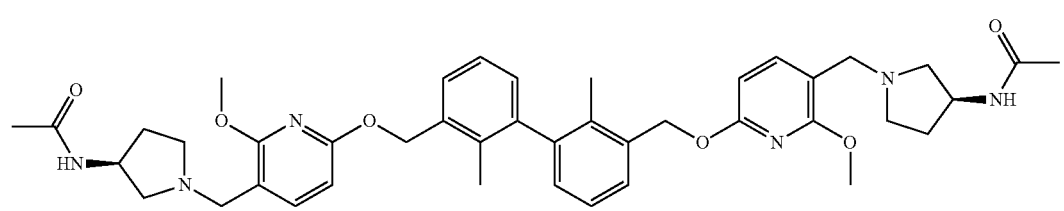 [SMILES: COc1nc(OCc2cccc(-c3cccc(COc4ccc(CN5CC[C@H](NC(C)=O)C5)c(OC)n4)c3C)c2C)ccc1CN1CC[C@H](NC(C)=O)C1] |

-continued

| No. | Structure of compound |
|---|---|
| 55 | |
| 56 | |
| 57 | |
| 58 | |
| 59 | |
| 60 | |

-continued

| No. | Structure of compound |
|---|---|
| 61 | |
| 62 | |
| 63 | |
| 64 | |
| 65 | |
| 66 | |

-continued
| No. | Structure of compound |
|---|---|
| 67 | 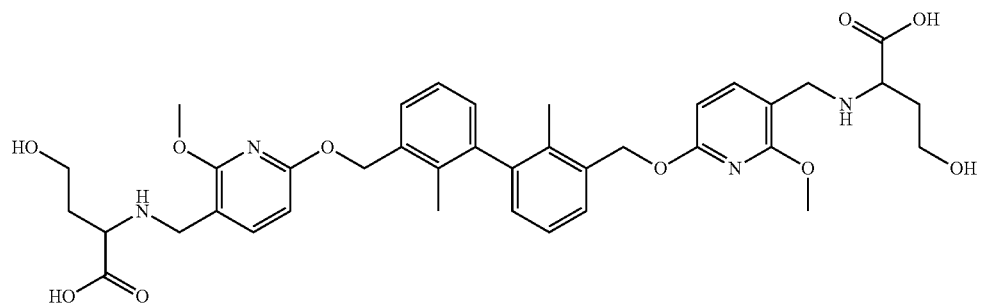 [SMILES: COc1nc(OCc2cccc(-c3cccc(COc4ccc(CNC(CCO)C(=O)O)c(OC)n4)c3C)c2C)ccc1CNC(CCO)C(=O)O] |
| 68 | 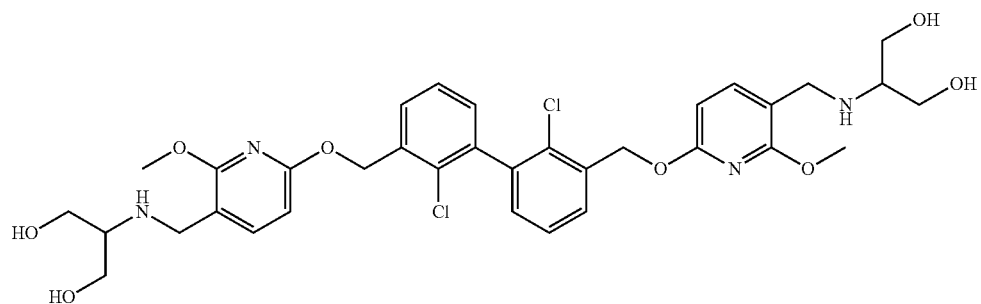 [SMILES: COc1nc(OCc2cccc(-c3cccc(COc4ccc(CNC(CO)CO)c(OC)n4)c3Cl)c2Cl)ccc1CNC(CO)CO] |
| 69 | 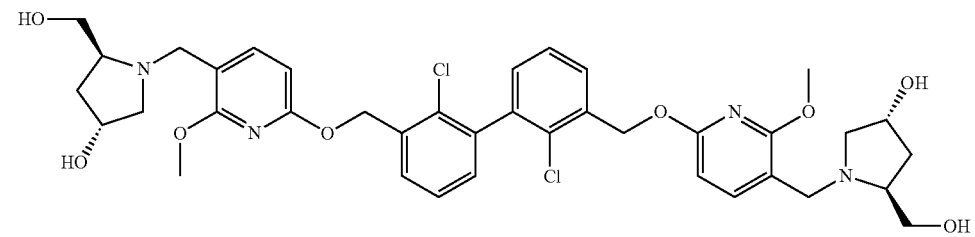 [SMILES: COc1nc(OCc2cccc(-c3cccc(COc4ccc(CN5C[C@H](O)C[C@H]5CO)c(OC)n4)c3Cl)c2Cl)ccc1CN1C[C@H](O)C[C@H]1CO] |
| 70 | 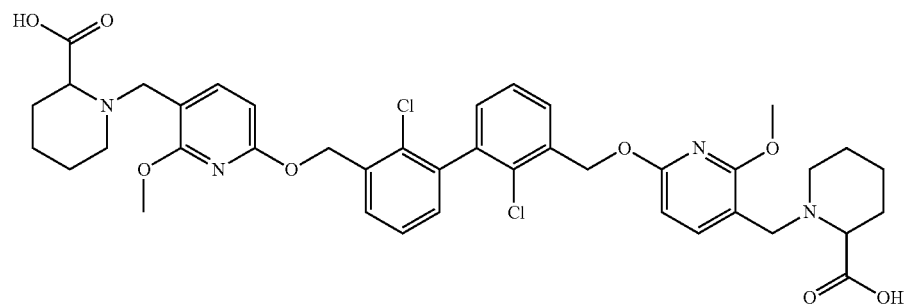 [SMILES: COc1nc(OCc2cccc(-c3cccc(COc4ccc(CN5CCCCC5C(=O)O)c(OC)n4)c3Cl)c2Cl)ccc1CN1CCCCC1C(=O)O] |
| 71 | 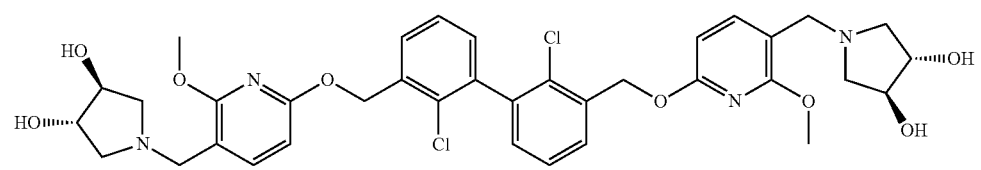 [SMILES: COc1nc(OCc2cccc(-c3cccc(COc4ccc(CN5C[C@H](O)[C@@H](O)C5)c(OC)n4)c3Cl)c2Cl)ccc1CN1C[C@H](O)[C@@H](O)C1] |

-continued

| No. | Structure of compound |
|---|---|
| 72 | |
| 73 | |
| 74 | |
| 75 | |
| 76 | |
| 77 | |
| 78 | |

| No. | Structure of compound |
|---|---|
| 79 | |
| 80 | |
| 81 | |
| 82 | |

2. A compound selected from the following group, or a stereoisomer, a racemate, or a pharmaceutically acceptable salt thereof,

| No. | Structure of compound |
|---|---|
| 6 | |

-continued
| No. | Structure of compound |
|---|---|
| 9 | 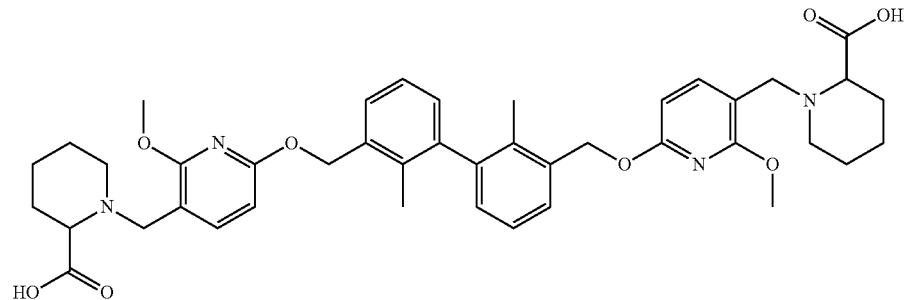 [SMILES: COc1nc(OCc2cccc(-c3cccc(COc4ccc(CN5CCCCC5C(=O)O)c(OC)n4)c3C)c2C)ccc1CN1CCCCC1C(=O)O] |
| 20 | 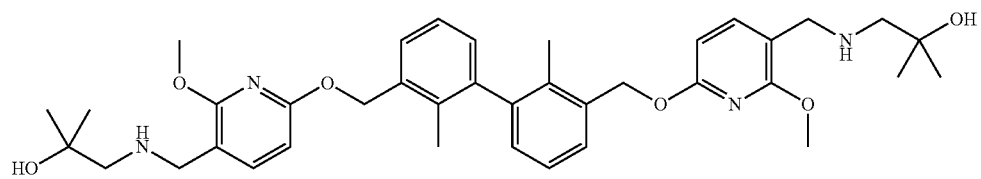 [SMILES: COc1nc(OCc2cccc(-c3cccc(COc4ccc(CNCC(C)(C)O)c(OC)n4)c3C)c2C)ccc1CNCC(C)(C)O] |
| 22 | 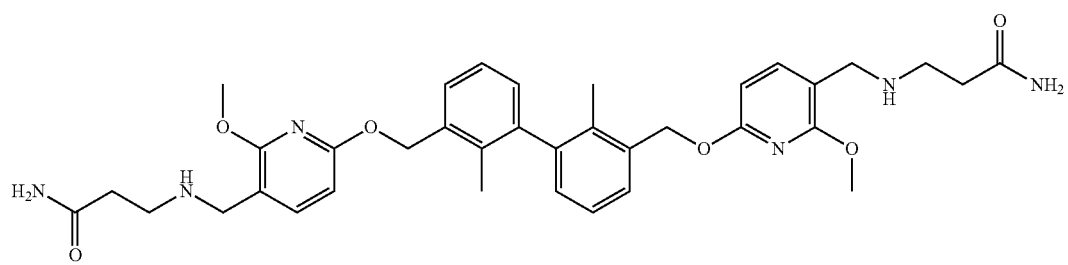 [SMILES: COc1nc(OCc2cccc(-c3cccc(COc4ccc(CNCCC(N)=O)c(OC)n4)c3C)c2C)ccc1CNCCC(N)=O] |
| 24 | 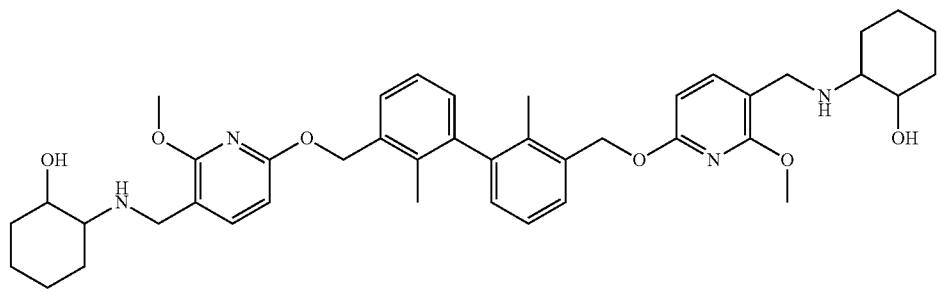 [SMILES: COc1nc(OCc2cccc(-c3cccc(COc4ccc(CNC5CCCCC5O)c(OC)n4)c3C)c2C)ccc1CNC1CCCCC1O] |
| 26 | 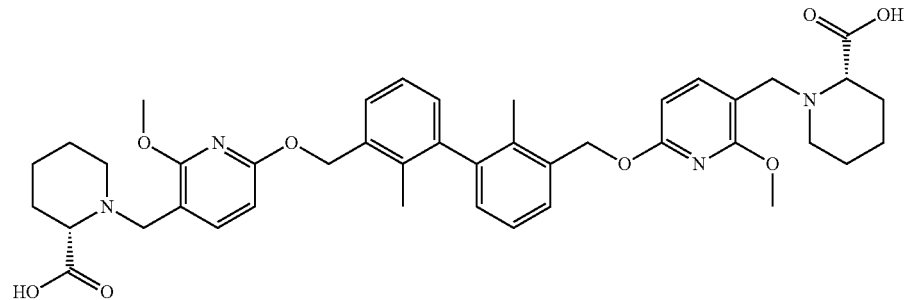 [SMILES: COc1nc(OCc2cccc(-c3cccc(COc4ccc(CN5CCCC[C@H]5C(=O)O)c(OC)n4)c3C)c2C)ccc1CN1CCCC[C@H]1C(=O)O] |

-continued
| No. | Structure of compound |
|---|---|
| 27 | 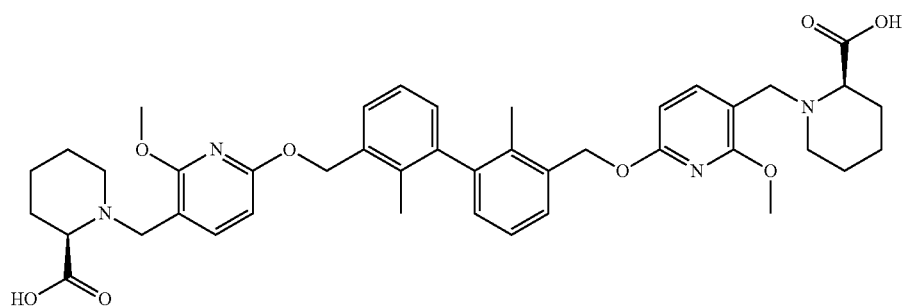 [SMILES: COc1nc(OCc2cccc(-c3cccc(COc4ccc(CN5CCCC[C@@H]5C(=O)O)c(OC)n4)c3C)c2C)ccc1CN1CCCC[C@@H]1C(=O)O] |
| 28 | 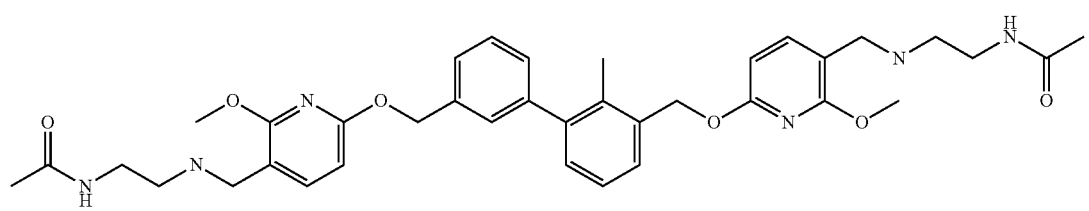 [SMILES: COc1nc(OCc2cccc(-c3cccc(COc4ccc(CNCCNC(C)=O)c(OC)n4)c3C)c2)ccc1CNCCNC(C)=O] |
| 30 | 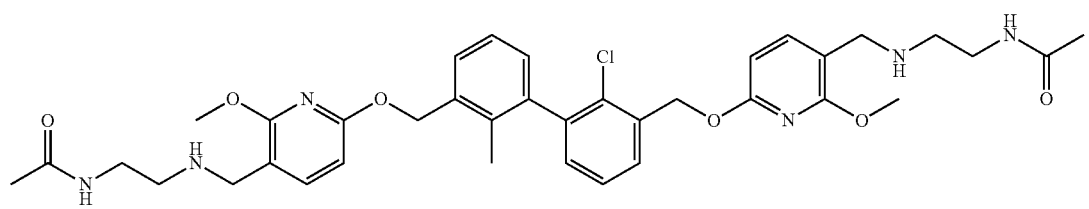 [SMILES: COc1nc(OCc2cccc(-c3cccc(COc4ccc(CNCCNC(C)=O)c(OC)n4)c3Cl)c2C)ccc1CNCCNC(C)=O] |
| 33 | 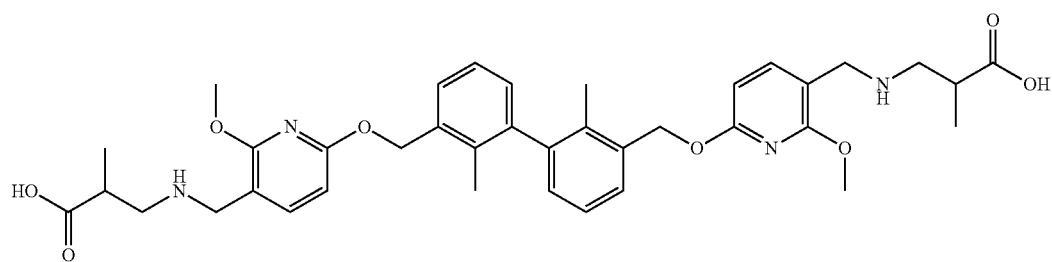 [SMILES: COc1nc(OCc2cccc(-c3cccc(COc4ccc(CNCC(C)C(=O)O)c(OC)n4)c3C)c2C)ccc1CNCC(C)C(=O)O] |
| 35 | 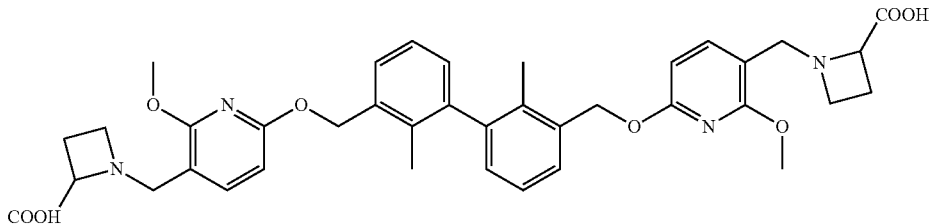 [SMILES: COc1nc(OCc2cccc(-c3cccc(COc4ccc(CN5CCC5C(=O)O)c(OC)n4)c3C)c2C)ccc1CN1CCC1C(=O)O] |
| 37 | 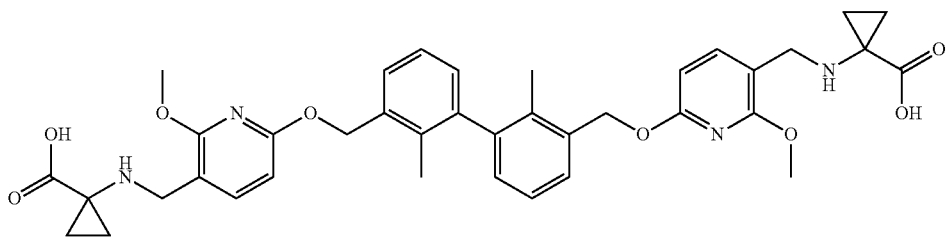 [SMILES: COc1nc(OCc2cccc(-c3cccc(COc4ccc(CNC5(C(=O)O)CC5)c(OC)n4)c3C)c2C)ccc1CNC1(C(=O)O)CC1] |

| No. | Structure of compound |
|---|---|
| 39 | 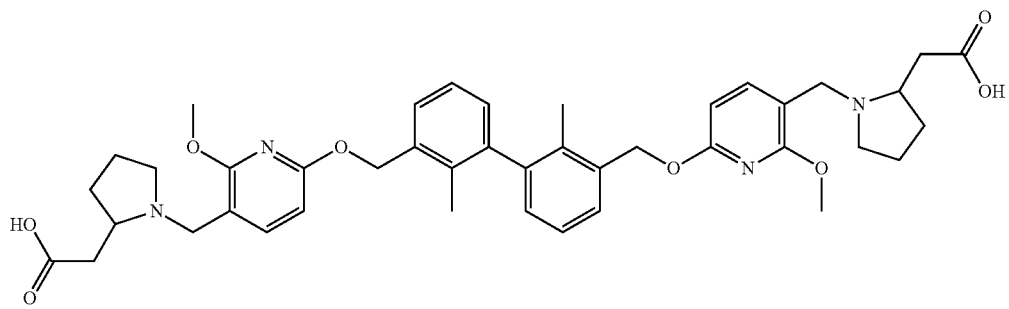 [SMILES: COc1nc(OCc2cccc(-c3cccc(COc4ccc(CN5CCCC5CC(=O)O)c(OC)n4)c3C)c2C)ccc1CN1CCCC1CC(=O)O] |
| 41 | 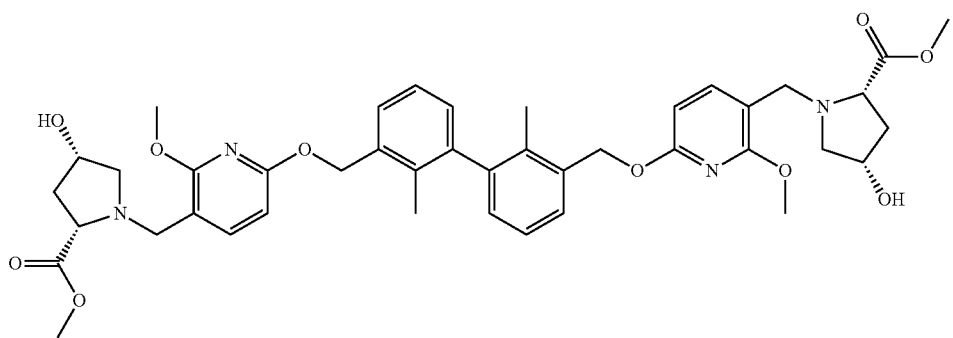 [SMILES: COC(=O)[C@@H]1C[C@H](O)CN1Cc1ccc(OCc2cccc(-c3cccc(COc4ccc(CN5C[C@@H](O)C[C@H]5C(=O)OC)c(OC)n4)c3C)c2C)nc1OC] |
| 42 | 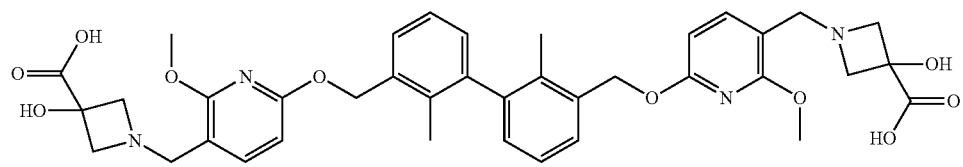 [SMILES: COc1nc(OCc2cccc(-c3cccc(COc4ccc(CN5CC(O)(C(=O)O)C5)c(OC)n4)c3C)c2C)ccc1CN1CC(O)(C(=O)O)C1] |
| 43 | 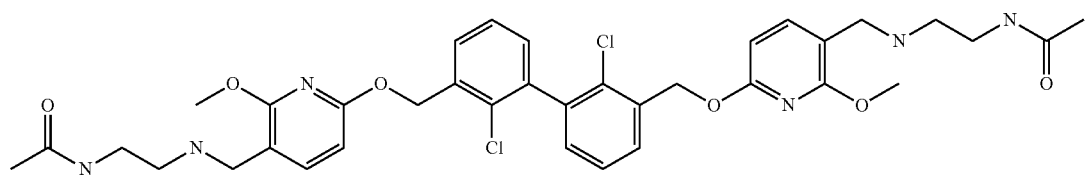 [SMILES: COc1nc(OCc2cccc(-c3cccc(COc4ccc(CNCCNC(C)=O)c(OC)n4)c3Cl)c2Cl)ccc1CNCCNC(C)=O] |
| 46 | 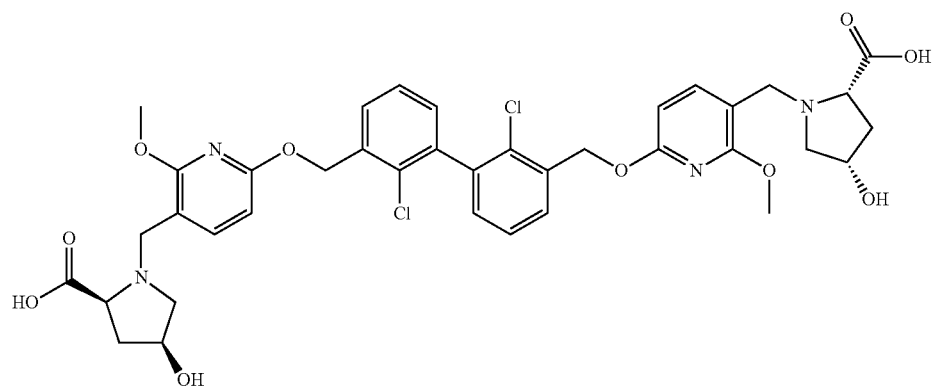 [SMILES: COc1nc(OCc2cccc(-c3cccc(COc4ccc(CN5C[C@@H](O)C[C@H]5C(=O)O)c(OC)n4)c3Cl)c2Cl)ccc1CN1C[C@@H](O)C[C@H]1C(=O)O] |

-continued
| No. | Structure of compound |
|---|---|
| 47 | 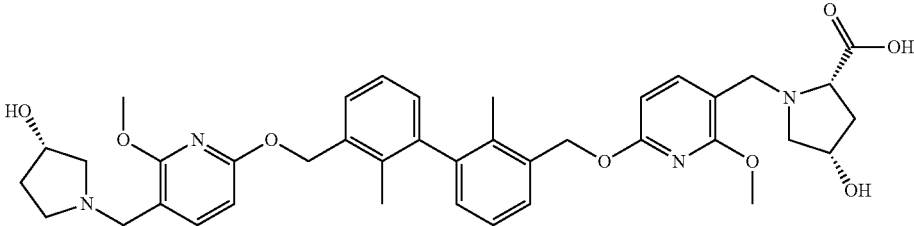 [SMILES: COc1nc(OCc2cccc(-c3cccc(COc4ccc(CN5C[C@@H](O)C[C@H]5C(=O)O)c(OC)n4)c3C)c2C)ccc1CN1CC[C@H](O)C1] |
| 49 | 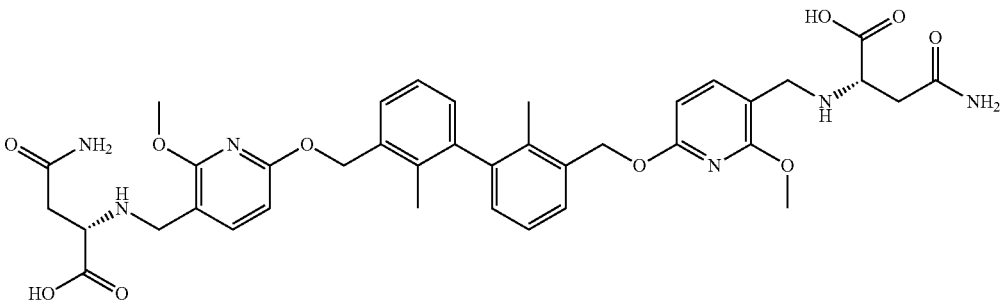 [SMILES: COc1nc(OCc2cccc(-c3cccc(COc4ccc(CN[C@@H](CC(N)=O)C(=O)O)c(OC)n4)c3C)c2C)ccc1CN[C@@H](CC(N)=O)C(=O)O] |
| 50 | 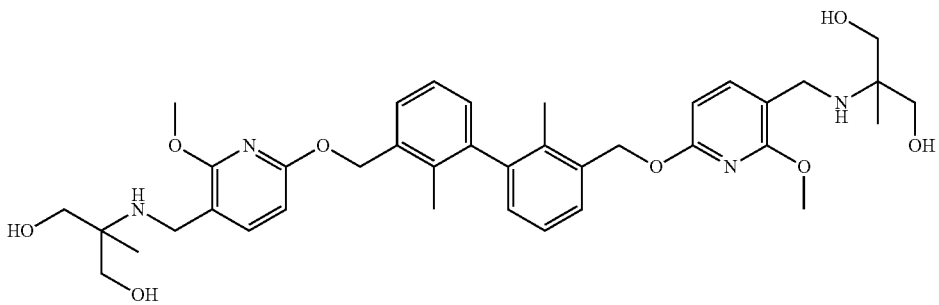 [SMILES: COc1nc(OCc2cccc(-c3cccc(COc4ccc(CNC(C)(CO)CO)c(OC)n4)c3C)c2C)ccc1CNC(C)(CO)CO] |
| 51 | 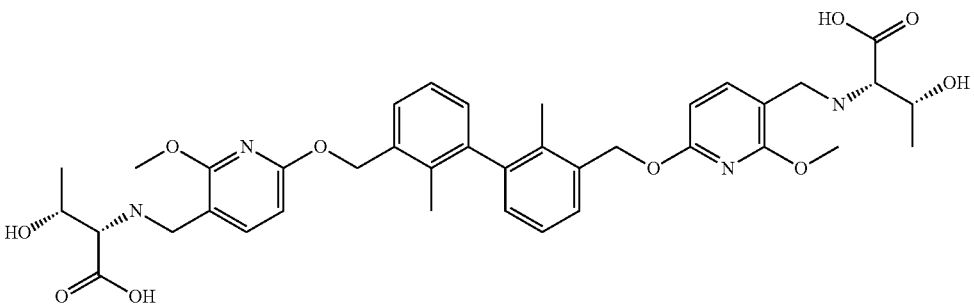 [SMILES: COc1nc(OCc2cccc(-c3cccc(COc4ccc(CN[C@H](C(=O)O)[C@@H](C)O)c(OC)n4)c3C)c2C)ccc1CN[C@H](C(=O)O)[C@@H](C)O] |
| 52 | 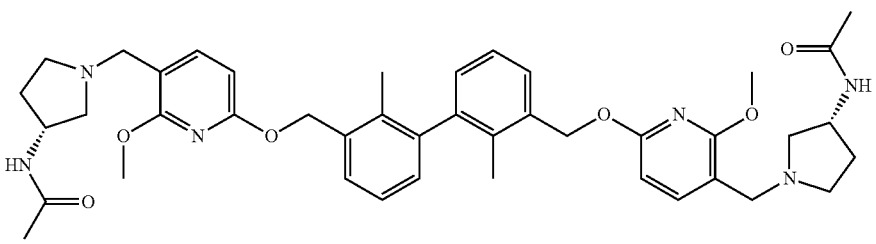 [SMILES: COc1nc(OCc2cccc(-c3cccc(COc4ccc(CN5CC[C@@H](NC(C)=O)C5)c(OC)n4)c3C)c2C)ccc1CN1CC[C@@H](NC(C)=O)C1] |
| 54 | 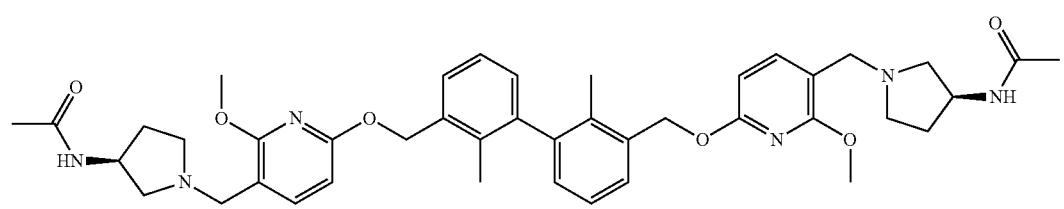 [SMILES: COc1nc(OCc2cccc(-c3cccc(COc4ccc(CN5CC[C@H](NC(C)=O)C5)c(OC)n4)c3C)c2C)ccc1CN1CC[C@H](NC(C)=O)C1] |

-continued
| No. | Structure of compound |
|---|---|
| 55 | 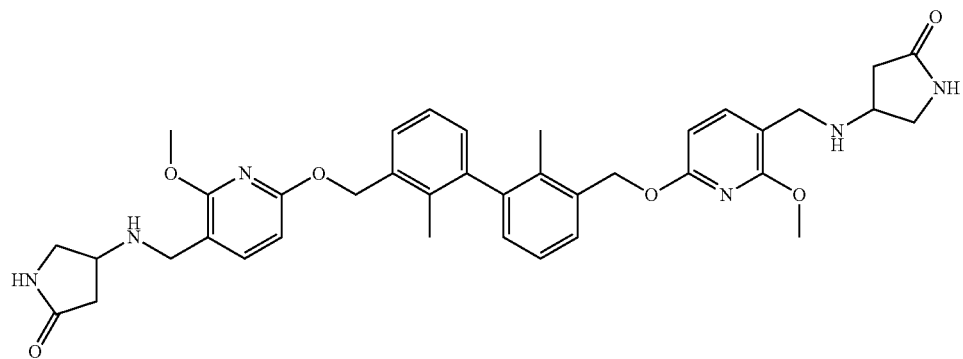 [SMILES: COc1nc(OCc2cccc(-c3cccc(COc4ccc(CNC5CNC(=O)C5)c(OC)n4)c3C)c2C)ccc1CNC1CNC(=O)C1] |
| 56 | 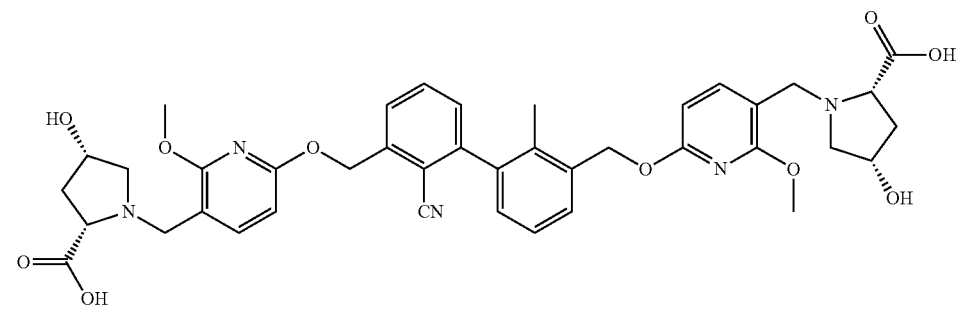 [SMILES: COc1nc(OCc2cccc(-c3cccc(COc4ccc(CN5C[C@@H](O)C[C@H]5C(=O)O)c(OC)n4)c3C#N)c2C)ccc1CN1C[C@@H](O)C[C@H]1C(=O)O] |
| 57 | 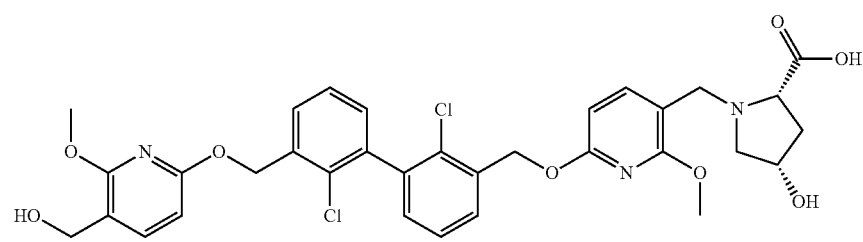 [SMILES: COc1nc(OCc2cccc(-c3cccc(COc4ccc(CN5C[C@@H](O)C[C@H]5C(=O)O)c(OC)n4)c3Cl)c2Cl)ccc1CO] |
| 58 | 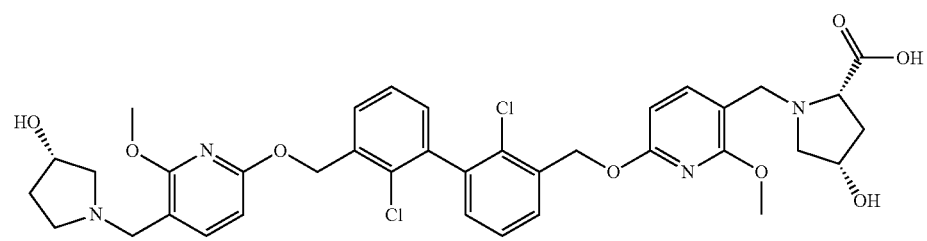 [SMILES: COc1nc(OCc2cccc(-c3cccc(COc4ccc(CN5C[C@@H](O)C[C@H]5C(=O)O)c(OC)n4)c3Cl)c2Cl)ccc1CN1CC[C@H](O)C1] |
| 59 | 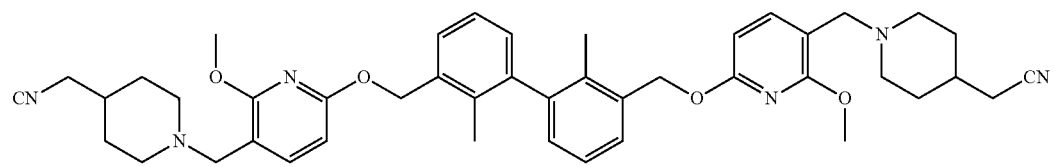 |
| 60 | 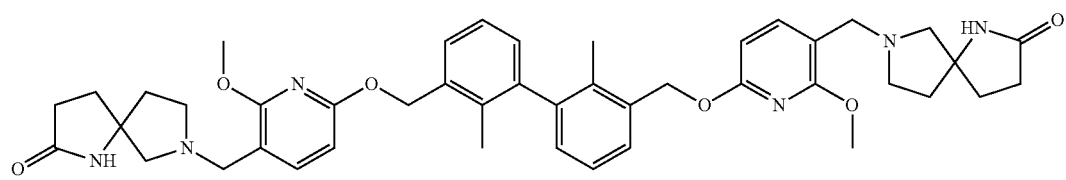 [SMILES: COc1nc(OCc2cccc(-c3cccc(COc4ccc(CN5CCC6(CCC(=O)N6)C5)c(OC)n4)c3C)c2C)ccc1CN1CCC2(CCC(=O)N2)C1] |

-continued
| No. | Structure of compound |
|---|---|
| 61 | 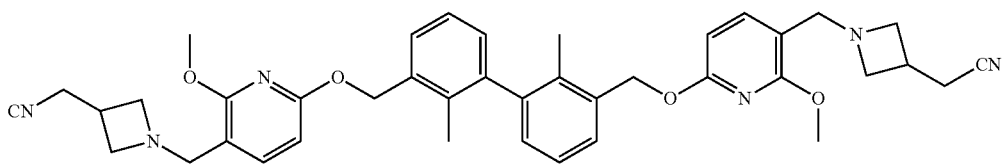 |
| 62 | 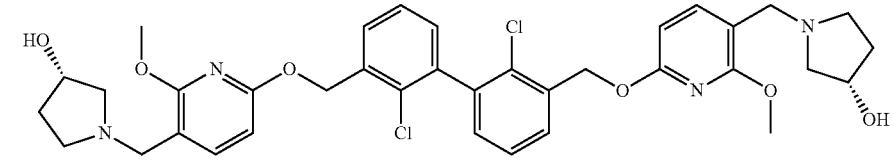 [SMILES: COc1nc(OCc2cccc(-c3cccc(COc4ccc(CN5CC[C@H](O)C5)c(OC)n4)c3Cl)c2Cl)ccc1CN1CC[C@H](O)C1] |
| 63 | 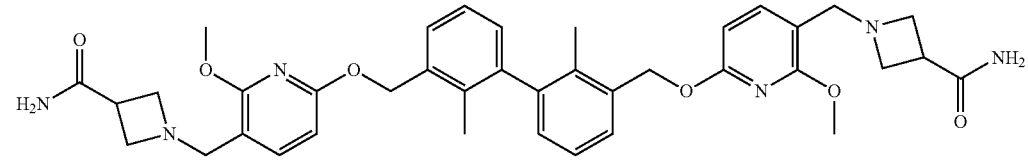 [SMILES: COc1nc(OCc2cccc(-c3cccc(COc4ccc(CN5CC(C(N)=O)C5)c(OC)n4)c3C)c2C)ccc1CN1CC(C(N)=O)C1] |
| 64 | 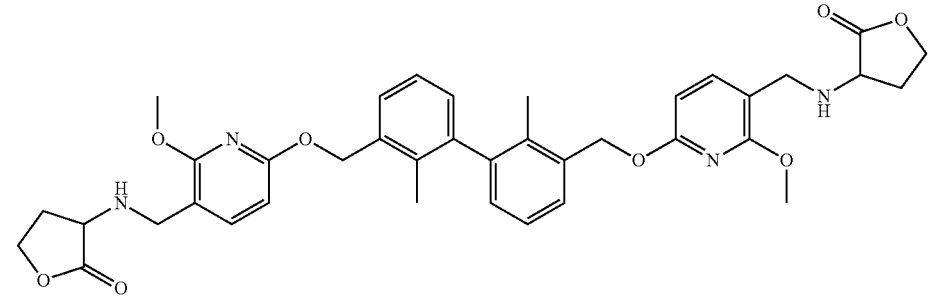 [SMILES: COc1nc(OCc2cccc(-c3cccc(COc4ccc(CNC5CCOC5=O)c(OC)n4)c3C)c2C)ccc1CNC1CCOC1=O] |
| 65 | 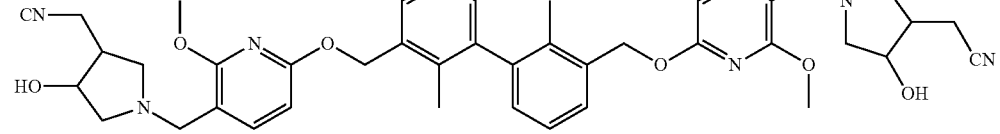 |
| 66 | 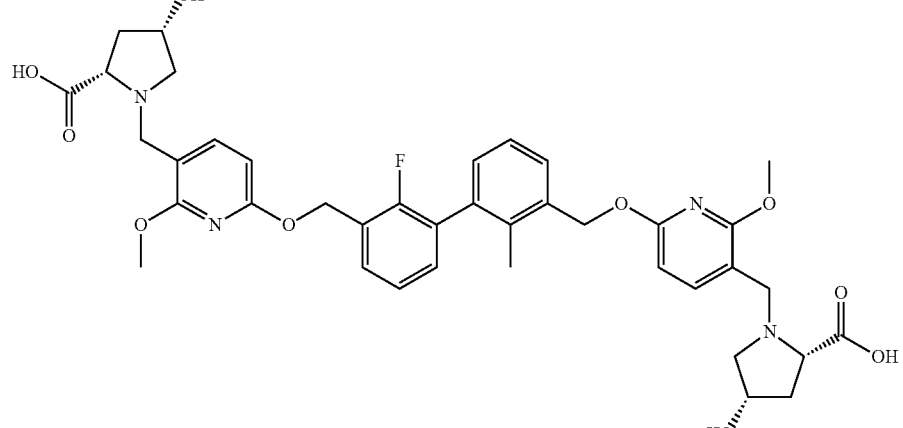 |

| No. | Structure of compound |
|---|---|
| 67 | 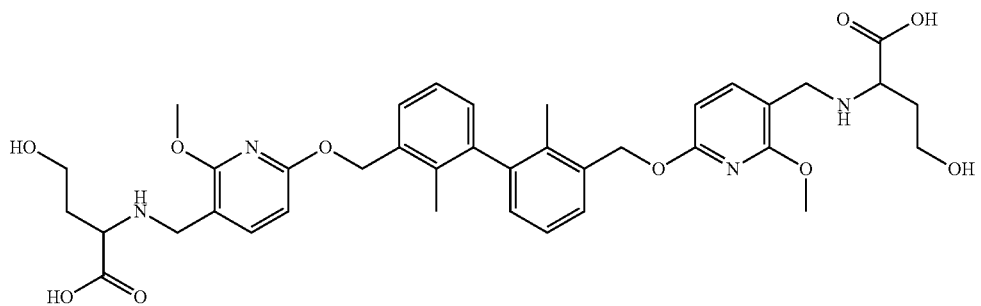 [SMILES: COc1nc(OCc2cccc(-c3cccc(COc4ccc(CNC(CCO)C(=O)O)c(OC)n4)c3C)c2C)ccc1CNC(CCO)C(=O)O] |
| 68 | 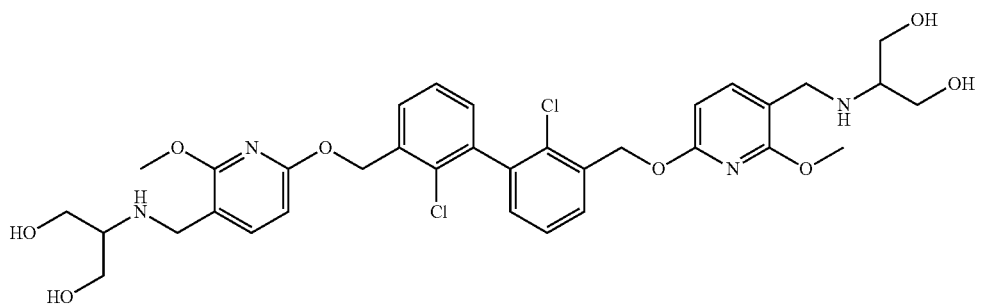 [SMILES: COc1nc(OCc2cccc(-c3cccc(COc4ccc(CNC(CO)CO)c(OC)n4)c3Cl)c2Cl)ccc1CNC(CO)CO] |
| 69 | 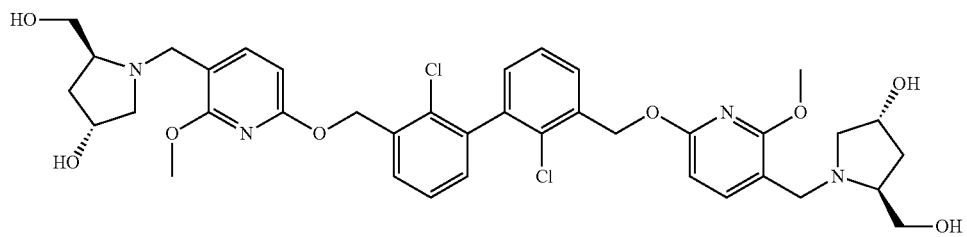 [SMILES: COc1nc(OCc2cccc(-c3cccc(COc4ccc(CN5C[C@H](O)C[C@H]5CO)c(OC)n4)c3Cl)c2Cl)ccc1CN1C[C@H](O)C[C@H]1CO] |
| 70 | 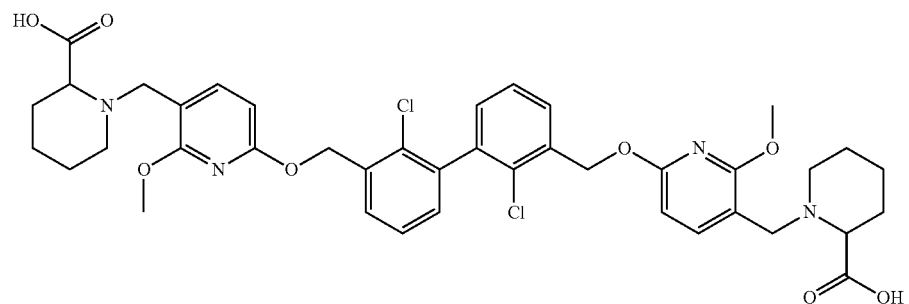 [SMILES: COc1nc(OCc2cccc(-c3cccc(COc4ccc(CN5CCCCC5C(=O)O)c(OC)n4)c3Cl)c2Cl)ccc1CN1CCCCC1C(=O)O] |
| 71 | 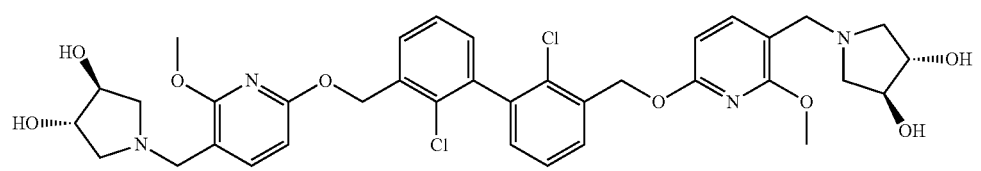 [SMILES: COc1nc(OCc2cccc(-c3cccc(COc4ccc(CN5C[C@H](O)[C@@H](O)C5)c(OC)n4)c3Cl)c2Cl)ccc1CN1C[C@H](O)[C@@H](O)C1] |

| No. | Structure of compound |
|---|---|
| 72 | 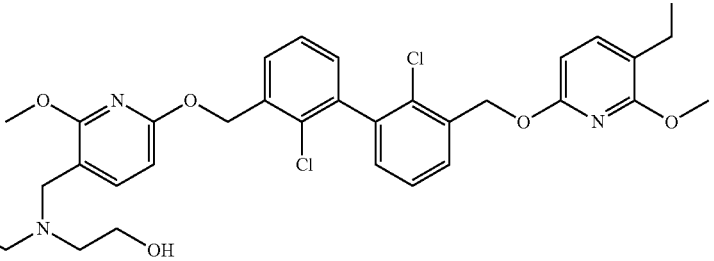 |
| 73 | 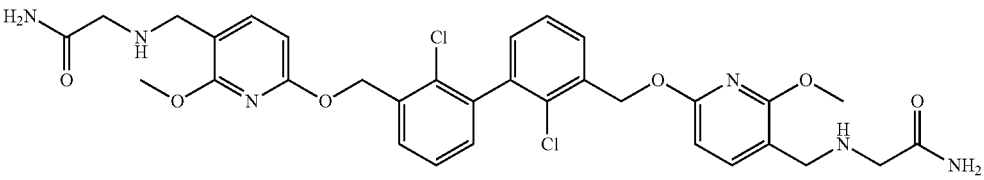 [SMILES: COc1nc(OCc2cccc(-c3cccc(COc4ccc(CNCC(N)=O)c(OC)n4)c3Cl)c2Cl)ccc1CNCC(N)=O] |
| 74 | 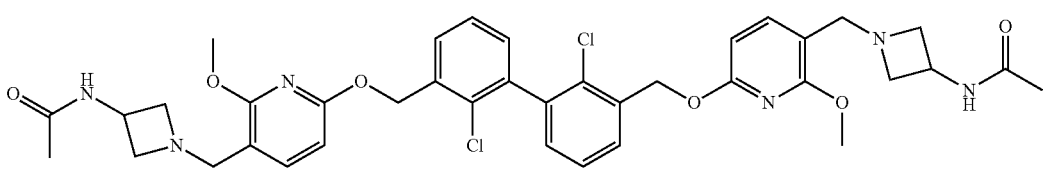 [SMILES: COc1nc(OCc2cccc(-c3cccc(COc4ccc(CN5CC(NC(C)=O)C5)c(OC)n4)c3Cl)c2Cl)ccc1CN1CC(NC(C)=O)C1] |
| 75 | 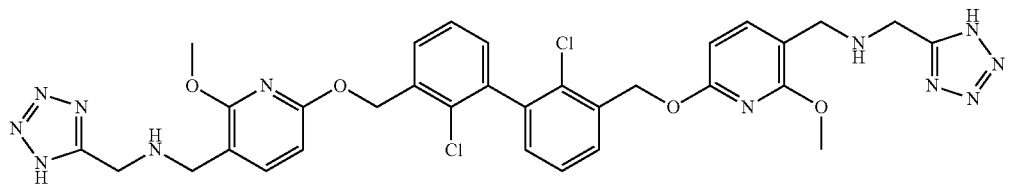 [SMILES: COc1nc(OCc2cccc(-c3cccc(COc4ccc(CNCc5nnn[nH]5)c(OC)n4)c3Cl)c2Cl)ccc1CNCc1nnn[nH]1] |
| 76 | 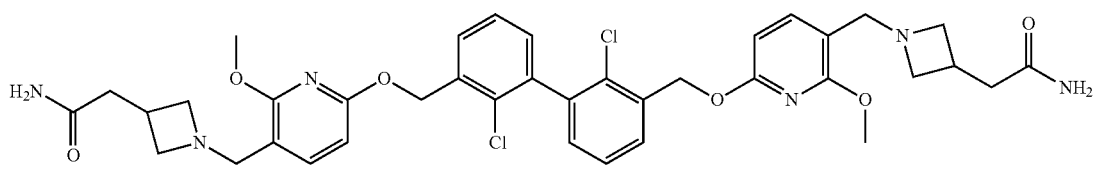 [SMILES: COc1nc(OCc2cccc(-c3cccc(COc4ccc(CN5CC(CC(N)=O)C5)c(OC)n4)c3Cl)c2Cl)ccc1CN1CC(CC(N)=O)C1] |
| 77 | 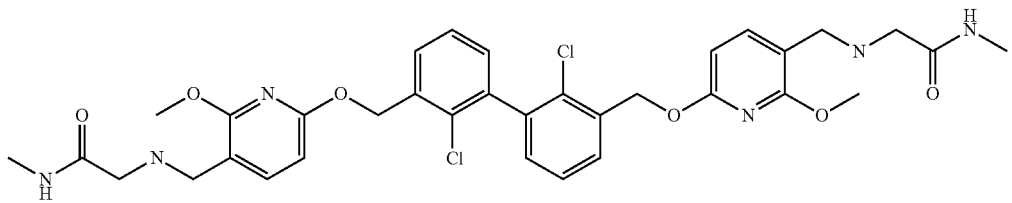 |
| 78 | 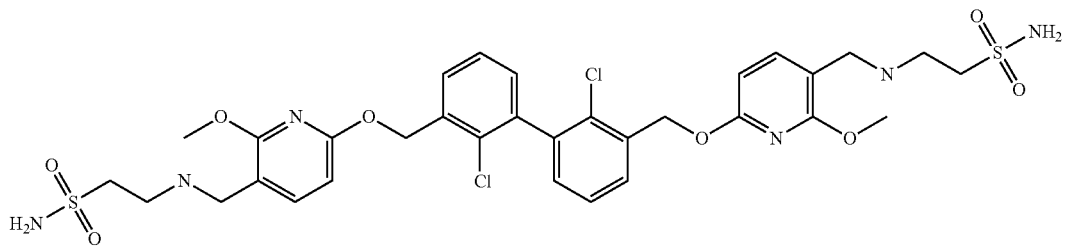 [SMILES: COc1nc(OCc2cccc(-c3cccc(COc4ccc(CNCCS(N)(=O)=O)c(OC)n4)c3Cl)c2Cl)ccc1CNCCS(N)(=O)=O] |

-continued

| No. | Structure of compound |
|---|---|
| 79 | |
| 80 | |
| 81 | |
| 82 | |

3. A compound selected from the following group, or a stereoisomer, a racemate, or a pharmaceutically acceptable salt thereof,

| No. | Structure of compound |
|---|---|
| 9 | |

| No. | Structure of compound |
|---|---|
| 26 | 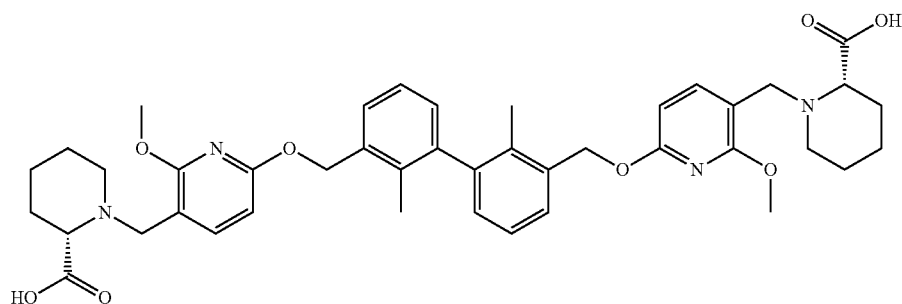 [SMILES: COc1nc(OCc2cccc(-c3cccc(COc4ccc(CN5CCCC[C@H]5C(=O)O)c(OC)n4)c3C)c2C)ccc1CN1CCCC[C@H]1C(=O)O] |
| 27 | 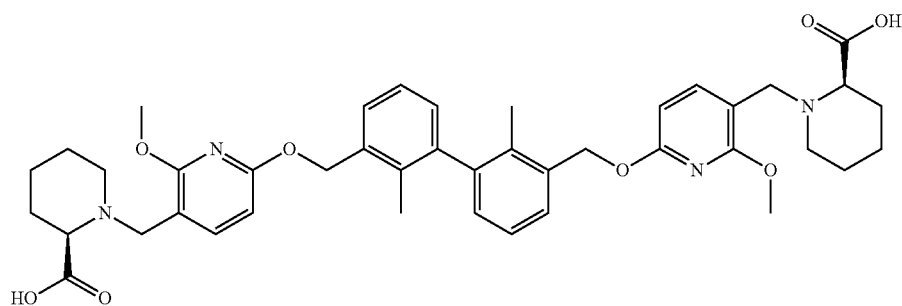 [SMILES: COc1nc(OCc2cccc(-c3cccc(COc4ccc(CN5CCCC[C@@H]5C(=O)O)c(OC)n4)c3C)c2C)ccc1CN1CCCC[C@@H]1C(=O)O] |
| 30 | 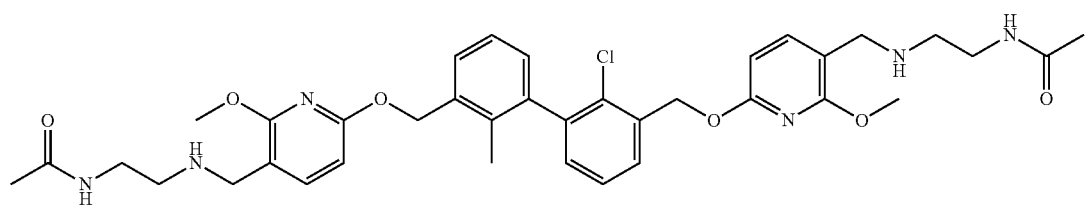 [SMILES: COc1nc(OCc2cccc(-c3cccc(COc4ccc(CNCCNC(C)=O)c(OC)n4)c3Cl)c2C)ccc1CNCCNC(C)=O] |
| 35 | 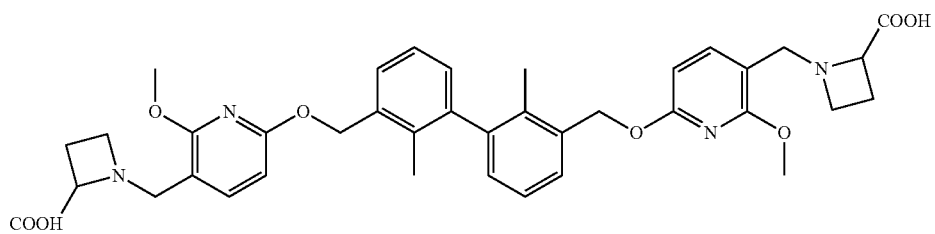 [SMILES: COc1nc(OCc2cccc(-c3cccc(COc4ccc(CN5CCC5C(=O)O)c(OC)n4)c3C)c2C)ccc1CN1CCC1C(=O)O] |
| 36 | 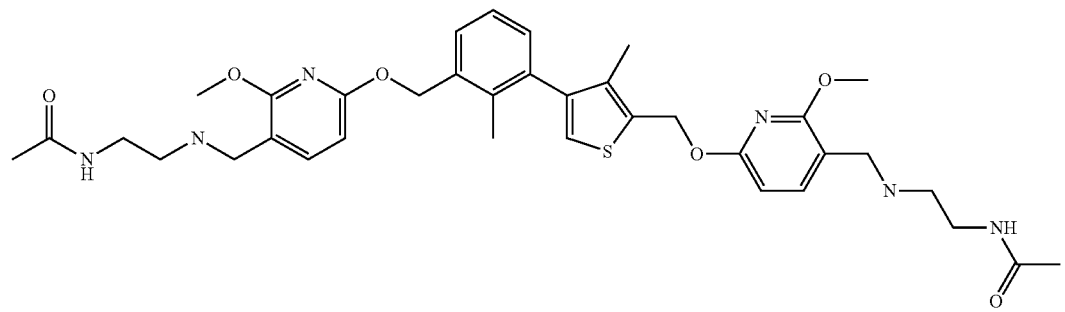 [SMILES: COc1nc(OCc2cccc(-c3csc(COc4ccc(CNCCNC(C)=O)c(OC)n4)c3C)c2C)ccc1CNCCNC(C)=O] |

| No. | Structure of compound |
|---|---|
| 37 | |
| 42 | |
| 43 | |
| 45 | |
| 46 | |
| 47 | |

-continued
| No. | Structure of compound |
|---|---|
| 49 | 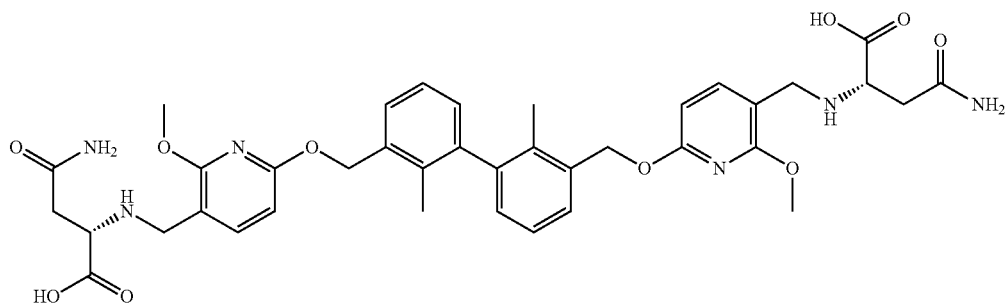 [SMILES: COc1nc(OCc2cccc(-c3cccc(COc4ccc(CN[C@@H](CC(N)=O)C(=O)O)c(OC)n4)c3C)c2C)ccc1CN[C@@H](CC(N)=O)C(=O)O] |
| 50 | 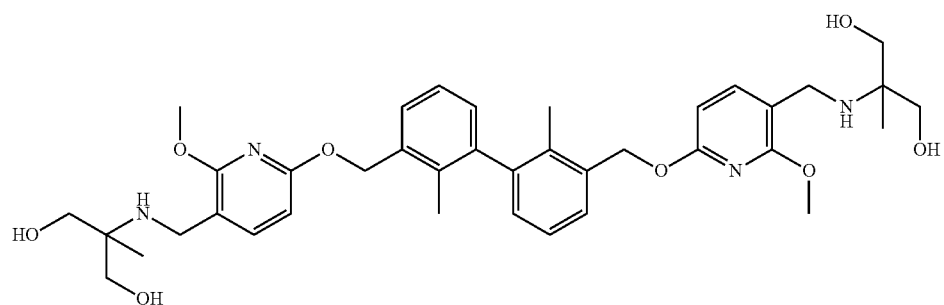 [SMILES: COc1nc(OCc2cccc(-c3cccc(COc4ccc(CNC(C)(CO)CO)c(OC)n4)c3C)c2C)ccc1CNC(C)(CO)CO] |
| 51 | 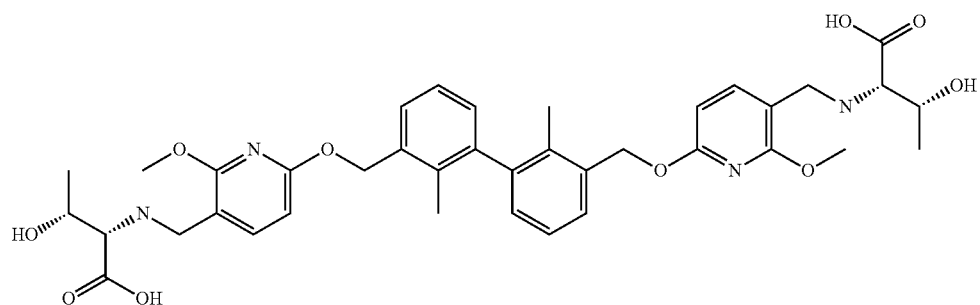 [SMILES: COc1nc(OCc2cccc(-c3cccc(COc4ccc(CN[C@H](C(=O)O)[C@@H](C)O)c(OC)n4)c3C)c2C)ccc1CN[C@H](C(=O)O)[C@@H](C)O] |
| 56 | 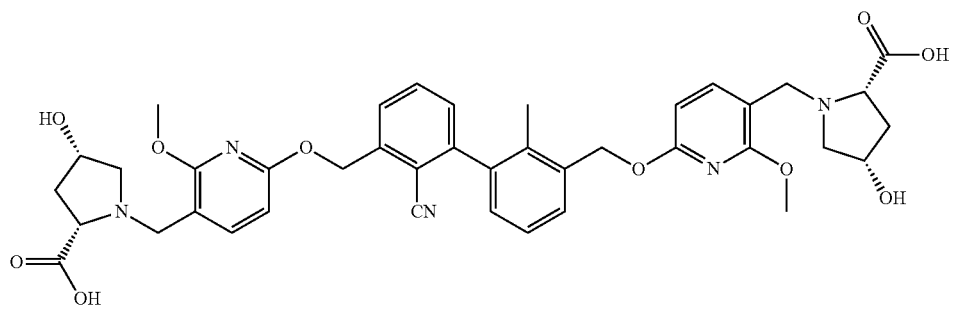 [SMILES: COc1nc(OCc2cccc(-c3cccc(COc4ccc(CN5C[C@@H](O)C[C@H]5C(=O)O)c(OC)n4)c3C#N)c2C)ccc1CN1C[C@@H](O)C[C@H]1C(=O)O] |
| 58 | 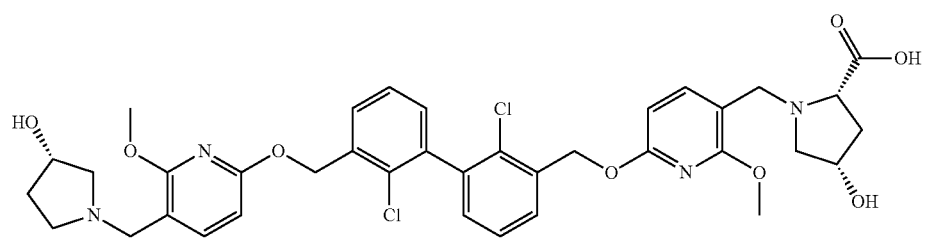 [SMILES: COc1nc(OCc2cccc(-c3cccc(COc4ccc(CN5C[C@@H](O)C[C@H]5C(=O)O)c(OC)n4)c3Cl)c2Cl)ccc1CN1CC[C@H](O)C1] |

-continued

| No. | Structure of compound |
|---|---|
| 60 | |
| 62 | |
| 63 | |
| 65 | |
| 66 | |
| 67 | |

-continued
| No. | Structure of compound |
|---|---|
| 68 | 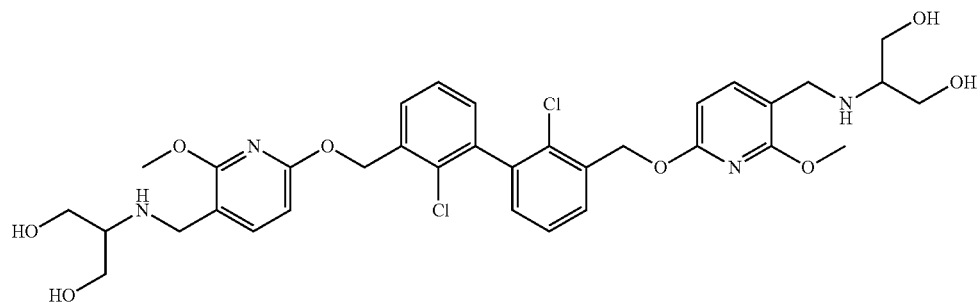 [SMILES: COc1nc(OCc2cccc(-c3cccc(COc4ccc(CNC(CO)CO)c(OC)n4)c3Cl)c2Cl)ccc1CNC(CO)CO] |
| 69 | 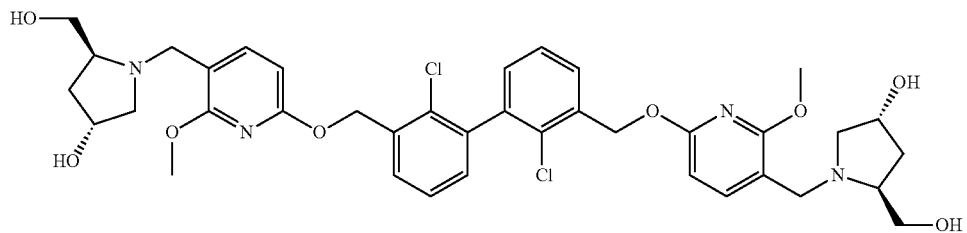 [SMILES: COc1nc(OCc2cccc(-c3cccc(COc4ccc(CN5C[C@H](O)C[C@H]5CO)c(OC)n4)c3Cl)c2Cl)ccc1CN1C[C@H](O)C[C@H]1CO] |
| 70 | 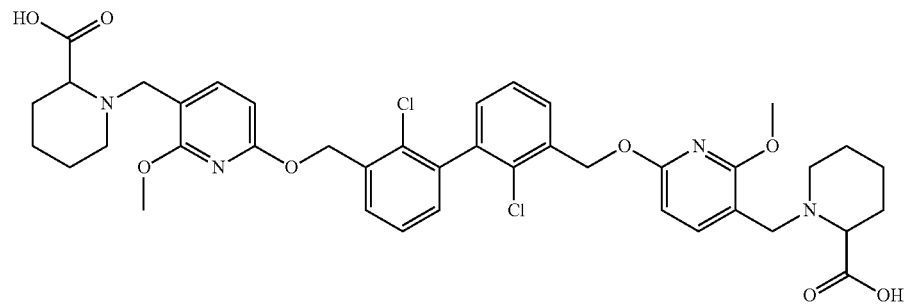 [SMILES: COc1nc(OCc2cccc(-c3cccc(COc4ccc(CN5CCCCC5C(=O)O)c(OC)n4)c3Cl)c2Cl)ccc1CN1CCCCC1C(=O)O] |
| 71 | 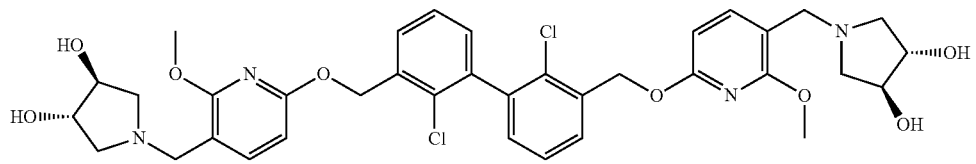 [SMILES: COc1nc(OCc2cccc(-c3cccc(COc4ccc(CN5C[C@H](O)[C@@H](O)C5)c(OC)n4)c3Cl)c2Cl)ccc1CN1C[C@H](O)[C@@H](O)C1] |
| 72 | 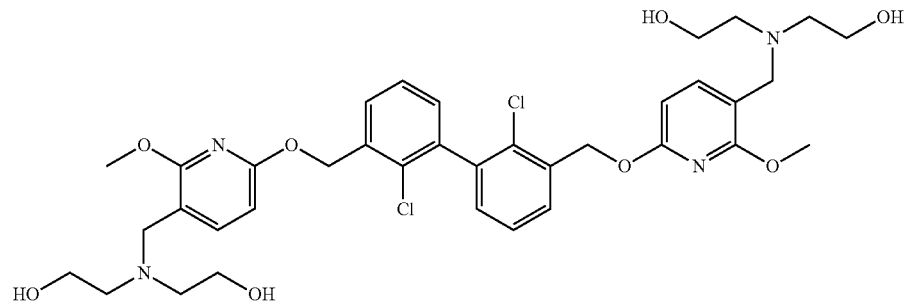 [SMILES: COc1nc(OCc2cccc(-c3cccc(COc4ccc(CN(CCO)CCO)c(OC)n4)c3Cl)c2Cl)ccc1CN(CCO)CCO] |
| 73 | 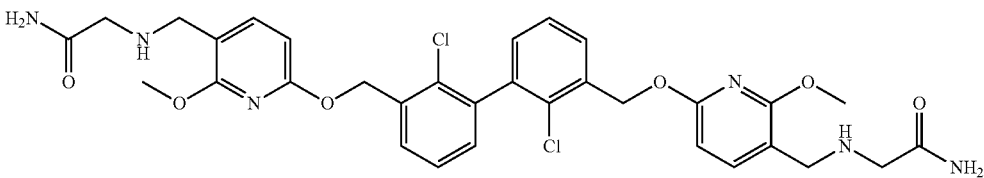 [SMILES: COc1nc(OCc2cccc(-c3cccc(COc4ccc(CNCC(N)=O)c(OC)n4)c3Cl)c2Cl)ccc1CNCC(N)=O] |

| No. | Structure of compound |
|---|---|
| 74 | |
| 75 | |
| 76 | |
| 77 | |
| 78 | |
| 79 | |

| No. | Structure of compound |
|---|---|
| 81 | 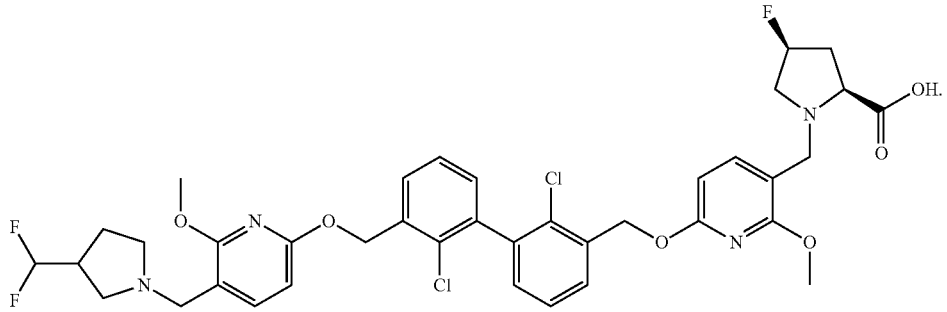 [SMILES: COc1nc(OCc2cccc(-c3cccc(COc4ccc(CN5C[C@@H](F)C[C@H]5C(=O)O)c(OC)n4)c3Cl)c2Cl)ccc1CN1CCC(C(F)F)C1] |
* * * * *